(12) United States Patent
Kusudo et al.

(10) Patent No.: US 7,698,562 B2
(45) Date of Patent: Apr. 13, 2010

(54) AUTHENTICATED PROGRAM EXECUTION METHOD

(75) Inventors: Tadao Kusudo, Osaka (JP); Takakazu Shiomi, Hirakata (JP)

(73) Assignee: Panasonic Corporation, Osaka (JP)

( * ) Notice: Subject to any disclaimer, the term of this patent is extended or adjusted under 35 U.S.C. 154(b) by 978 days.

(21) Appl. No.: 11/012,335

(22) Filed: Dec. 16, 2004

(65) Prior Publication Data
US 2005/0138397 A1 Jun. 23, 2005

Related U.S. Application Data

(60) Provisional application No. 60/530,663, filed on Dec. 19, 2003.

(30) Foreign Application Priority Data

Dec. 18, 2003 (JP) ............................. 2003-421616

(51) Int. Cl.
H04L 9/32 (2006.01)
(52) U.S. Cl. ..................................... 713/181
(58) Field of Classification Search ................. 713/181
See application file for complete search history.

(56) References Cited

U.S. PATENT DOCUMENTS

| | | | |
|---|---|---|---|
| 5,625,693 | A | 4/1997 | Rohatgi et al. |
| 6,832,323 | B1 | 12/2004 | Booth et al. |
| 7,356,815 | B2 * | 4/2008 | Sarfati et al. ............... 717/168 |
| 2001/0030959 | A1 * | 10/2001 | Ozawa et al. ............... 370/386 |
| 2002/0055355 | A1 * | 5/2002 | Ikeda ......................... 455/419 |
| 2003/0114144 | A1 | 6/2003 | Minemura |
| 2003/0217369 | A1 | 11/2003 | Heredia |

FOREIGN PATENT DOCUMENTS

| | | |
|---|---|---|
| EP | 0717353 | 6/1996 |
| EP | 0752786 | 1/1997 |
| EP | 1326396 | 7/2003 |
| JP | 2000-029833 | 1/2000 |
| WO | 01/31442 | 5/2001 |
| WO | 02/086746 | 10/2002 |

OTHER PUBLICATIONS

English Language Abstract of JP 2000-029833.
U.S. Appl. No. 11/012,300 to Terao et al.
Cablelabs, "OpenCable Application Platform Specification, OCAP 1.0 Profile," Nov. 21, 2003, downloaded from http://web.archive.org/web/*/http://www.opencable.com/specifications/ on Apr. 15, 2005.

(Continued)

Primary Examiner—Nasser G Moazzami
Assistant Examiner—Michael S McNally
(74) Attorney, Agent, or Firm—Greenblum & Bernstein, P.L.C.

(57) ABSTRACT

According to a conventional technique, in the case where a program is stored into a non-volatile memory once and then activated, authentication of the program is performed immediately before such activation. However, calculations such as decryption of encrypted values are required before the activation of the program starts, which causes the problem that responsiveness is decreased in proportion to the time required for calculations. In order to solve this problem, authentication of a program is performed immediately before such program is stored, so that no authentication is performed or only a part of the authentication is performed to verify the validity of certificates at program activation time.

6 Claims, 44 Drawing Sheets

OTHER PUBLICATIONS

DVB, "Digital Video Broadcasting (DVB) Multimedia Home Platform (MHP) Specification 1.1.1," Jun. 2003, downloaded from http://www.etsi.org/services_products/freestandard/home.htm on Apr. 15, 2005.

U.S. Appl. No. 11/012,300, entitled "Program Data File Storage Method and Authenticated Program Execution Method", to Terao et al., filed Dec. 16, 2004.

* cited by examiner

FIG.2

| Frequency band | Usage | Modulation technique |
|---|---|---|
| 5~130MHz | Out Of Band (OOB) Data exchange between head end and terminals | QPSK |
| 130~864MHz | In-band Ordinary television broadcasting including video and audio | QAM |

FIG.3

| Frequency band | Usage |
|---|---|
| 70~74MHz | Data transmission from head end 101 to terminal apparatuses |
| 10.0~10.1MHz | Data transmission from terminal apparatus A111 to head end 101 |
| 10.1~10.2MHz | Data transmission from terminal apparatus B112 to head end 101 |
| 10.2~10.3MHz | Data transmission from terminal apparatus C113 to head end 101 |

FIG.4

| Frequency band | Usage |
|---|---|
| 150~156MHz | Television channel 1 |
| 156~162MHz | Television channel 2 |
| ⋮ | ⋮ |
| 310~311MHz | Radio channel 1 |
| ⋮ | ⋮ |

FIG.20

| Java program identifier 2001 | Control information 2002 | DSMCC identifier 2003 | Program name 2004 | Priority 2005 |
|---|---|---|---|---|
| 0x7001 | autostart | 1 | /a/PPV1Xlet | 200 |
| 0x7002 | present | 1 | /b/PPVXlet2 | 201 |

2011 → (row 1)
2012 → (row 2)

| File name or directory name 2211 | Hash algorithm 2212 | Hash value 2213 |
|---|---|---|
| ocap.certificate.1 | SHA1 | e3 f4...3f |
| ocap.signaturefile.1 | SHA1 | 03 98...35 |
| a | SHA1 | 45 97...20 |
| b | SHA1 | a3 76...39 |

| File name or directory name 2221 | Hash algorithm 2222 | Hash value 2223 |
|---|---|---|
| PPV1Xlet.class | SHA1 | c8 38...59 |

| File name or directory name 2231 | Hash algorithm 2232 | Hash value 2233 |
|---|---|---|
| PPV2Xlet.class | SHA1 | 34 b4...56 |

FIG.34

```
"-//OCAP//DTD Application Description File 1.0//EN"
"http://www.cablelabs.com/ocap/dtd/applicationdescriptionfile
-1-0.dtd"
<applicationdescription>
    <dir name="/">
        <file name="ocap.hashfile" size="25"/>
        <file name="ocap.certificate.1" size="100"/>
        <file name="ocap.signaturefile.1" size="30"/>
        <dir name="a">
            <file name="ocap.hashfile" size="15"/>
            <file name="PPV1Xlet.class" size="1000"/>
        </dir>
        <dir name="b">
            <file name="ocap.hashfile"/>
        </dir>
    </dir>
</applicationdescription>
```

| File name or directory name 4611 | Hash algorithm 4612 | Hash value 4613 |
|---|---|---|
| ocap.certificate.1 | SHA1 | d3 f4...3f |
| ocap.signaturefile.1 | SHA1 | a3 98...35 |
| a | SHA1 | 45 97...20 |
| ocap.crl.2 | SHA1 | cd 76...39 |
| ocap.certificate.2 | SHA1 | ff 45...29 |

FIG.49

| Issuer name 491 | Serial number 492 | Revocation date/time 493 |
|---|---|---|
| P | 3 | 2003-06-23 15:00 GMT |
| S | 5 | 2003-04-12 23:00 GMT |
| D | 1 | 2002-08-03 09:10 GMT |
| T | 10 | 2003-12-02 05:00 GMT |
| K | 13 | 2003-12-04 02:50 GMT |

FIG.51

```
"-//OCAP//DTD Application Description File 1.0//EN"
"http://www.cablelabs.com/ocap/dtd/applicationdescriptionfile
-1-0.dtd"
<applicationdescription>
   <dir name="/">
      <file name="ocap.hashfile" size="25"/>
      <dir name="a">
         <file name="PPV1Xlet.class" size="1000"/>
      </dir>
      <dir name="b">
         <file name="ocap.hashfile" size="15"/>
         <file name="PPV2Xlet.class" size="1000"/>
      </dir>
   </dir>
</applicationdescription>
```

AUTHENTICATED PROGRAM EXECUTION METHOD

CROSS REFERENCE TO RELATED APPLICATION

This application claims the benefit of U.S. Provisional Application No. 60/530,663, filed on Dec. 19, 2003, the contents of which are herein incorporated by reference in its entirety.

TECHNICAL FIELD

The present invention relates to an authenticated program execution method that verifies the credibility of a downloaded program and executes the program that has been verified to be credible.

BACKGROUND ART

The function in a digital television of downloading a program and checking/guaranteeing the credibility of such program is described in the DVB-MHP specification "ETSI TS 101 812 V1.2.1 DVB-MHP Specification 1.0.2", and others. This DVB-MHP specification defines the function of verifying that a program superimposed on a broadcast wave being received has not been tampered with as well as that whether or not such program was issued by a reliable organization. This function makes it possible to prevent a rewritten program that dose not operate as originally required and therefore would inflict damage to the digital television and a program of a spoofing third party, from being activated.

In addition, the Japanese Laid-Out Patent Application No. 2000-29833 describes a technique, which is comprised of a server apparatus for accumulating and transmitting data and a terminal apparatus for receiving data via a network, to prevent accumulated data from being illicitly used by accumulating the received data in the terminal apparatus. FIG. 1 of the Japanese Laid-Out Patent Application No. 2000-29833 illustrates the technique that the server apparatus 10 copies data stored in the storage unit 15 into the storage unit 23 in response to a request from the terminal apparatus 20, and when the data stored in the storage unit 23 is wished to be used, the inquiry unit 26 makes an inquiry to the server apparatus 10, the authentication unit 13 performs an audit about the use of the data, and if there is no problem, the terminal apparatus 20 uses the data. The above apparatus is capable of loading data after checking the credibility of the data stored in a non-volatile memory even when the power is turned ON/OFF. Checking the credibility of programs and data is hereinafter referred to as authentication.

According to a conventional technique, however, in the case of storing a program into a non-volatile memory once so as to activate such program after the apparatus is powered ON/OFF, authentication of the program is performed immediately before it is activated. In this case, it is necessary to perform calculations such as decryption of an encrypted value before the activation of the program starts, which causes a problem that responsiveness is decreased more as a longer time is required for calculations. Especially in the case where a program is frequently activated or where the capacity of a program is large, the responsiveness becomes more and more degraded since the amount of calculations increases in proportion to activation frequency and capacity.

In view of the above problem, it is desired to provide a program authentication apparatus such as digital television with increased responsiveness that is capable of shortening the time required before a program is activated, while guaranteeing the credibility of the program.

DISCLOSURE OF INVENTION

The present invention aims at providing an authenticated program execution method that is both capable of guaranteeing the credibility and improving the responsiveness by performing authentication immediately before a program is stored, and performing no authentication or only a part of authentication at the time of program activation.

In order to solve the conventional problem, the authenticated program execution method according to the present invention is comprised of: an authentication and storage step of authenticating a program included in a transport stream and storing the authenticated program into a broadcast receiver according to information concerning storage of each data file of the program; and an execution step of executing the authenticated stored program, wherein the authentication and storage step includes: a first step of verifying whether two hash values are consistent or not, one of the hash values being calculated from each data file included in the program and the other hash value being stored in a hash file corresponding to said each data file; a second step of verifying whether a certificate file included in the program is valid or not; a third step of verifying whether a decrypted value and a hash value are consistent or not, the decrypted value being obtained by decrypting a signature value of a signature file included in the program using a public key of a leaf certificate included in the certificate file of the program, and the hash value being calculated from a hash file located in a top directory of the program; and a fourth step of authenticating the program and storing each data file of the authenticated program according to the information concerning storage, in the case where all of the following are satisfied: the two hash values are verified to be consistent in the first step; the certificate file is verified to be valid in the second step; and the decrypted value and the hash value are verified to be consistent in the third step, and the execution step includes a fifth step of verifying whether the certificate file included in the stored program is valid or not, and in the execution step, the stored program is authenticated again and executed only in the case where the certificate file included in the stored program is verified to be valid in the fifth step.

Accordingly, it becomes possible to shorten the time required before a program is activated, while guaranteeing the credibility of the program.

Moreover, in the case where the program has a directory structure, each data file included in each directory and the hash file corresponding to said each data file may be located in a same directory, and the first step may be executed for each data file included in each directory.

Accordingly, it becomes possible to check, for each data file included in each directory, whether the hash value calculated from the data file and a hash value stored in a hash file corresponding to said data file are consistent or not.

Furthermore, the second step may include a sixth step of verifying whether two root certificates match or not, one of the root certificates being in the certificate file included in the program and the other root certificate being installed in the broadcast receiver, and in the second step, the certificate file may be verified to be valid in the case where the two root certificates match.

Here, the second step may further include a seventh step of verifying a validity period of each certificate in the certificate file included in the program, and in the second step, the certificate file may be verified to be valid in the case where both of the following are satisfied: the two root certificates match; and time at which the authentication is performed is within the validity period of each certificate in the certificate file.

Accordingly, it becomes possible to prevent a program from being stored in the case where root certificates do not match and the validity period of the certificate is expired.

Moreover, the fifth step may include an eighth step of verifying whether two root certificates match or not, one of the root certificates being in the certificate file included in the stored program and the other root certificate being installed in the broadcast receiver, and in the fifth step, the certificate file included in the stored program may be verified to be valid in the case where the two root certificates match.

Here, the fifth step may further include a ninth step of verifying a validity period of each certificate in the certificate file included in the stored program, and in the fifth step, the certificate file included in the stored program may be verified to be valid in the case where both of the following are satisfied: the two root certificates match; and time at which the execution is performed is within the validity period of each certificate in the certificate file.

Accordingly, it becomes possible to prevent a program from being executed in the case where root certificates do not match and the validity period of the certificate is expired.

Note that not only is it possible to embody the present invention as an authenticated program execution method as above but also as an authenticated program execution apparatus that includes, as its units, the characteristic steps included in the authenticated program execution method, and as a program that causes a computer to execute these steps. It should be also noted that such program can be distributed on a recording medium such as CD-ROM and via a transmission medium such as the Internet.

As is obvious from the above descriptions, the authenticated program execution method according to the present invention is capable of shortening the time required before a program is activated, while guaranteeing the credibility of the program.

The disclosure of Japanese Patent Application No. 2003-421616 filed on Dec. 18, 2003 including specification, drawings and claims is incorporated herein by reference in its entirety.

BRIEF DESCRIPTION OF DRAWINGS

These and other objects, advantages and features of the invention will become apparent from the following description thereof taken in conjunction with the accompanying drawings that illustrate a specific embodiment of the invention. In the Drawings:

FIG. 2 is a diagram showing an example of using frequency bands to be used for communications between a head end and terminal apparatuses in the cable television system according to the present invention;

FIG. 3 is a diagram showing an example of using frequency bands to be used for communications between the head end and the terminal apparatuses in the cable television system according to the present invention;

FIG. 4 is a diagram showing an example of using frequency bands to be used for communications between the head end and the terminal apparatuses in the cable television system according to the present invention;

FIG. 20 is a schematic diagram showing the contents of XAIT according to the present invention;

FIGS. 22A, 22B, and 22C are diagrams, each showing an example of files that include hash values of files or directories according to the present invention;

FIG. 34 is a diagram showing an example of a file to be used to specify files to be stored according to the present invention;

FIG. 46 is a diagram showing an example of a file that includes hash values of files or directories according to the present invention;

FIG. 49 is a schematic diagram showing a database of revoked certificates according to the present invention;

FIG. 51 is a diagram showing an example file that is used to specify files to be stored according to the present invention.

BEST MODE FOR CARRYING OUT THE INVENTION

The following describes embodiments of the present invention with reference to the drawings.

FIRST EMBODIMENT

Figure 1:
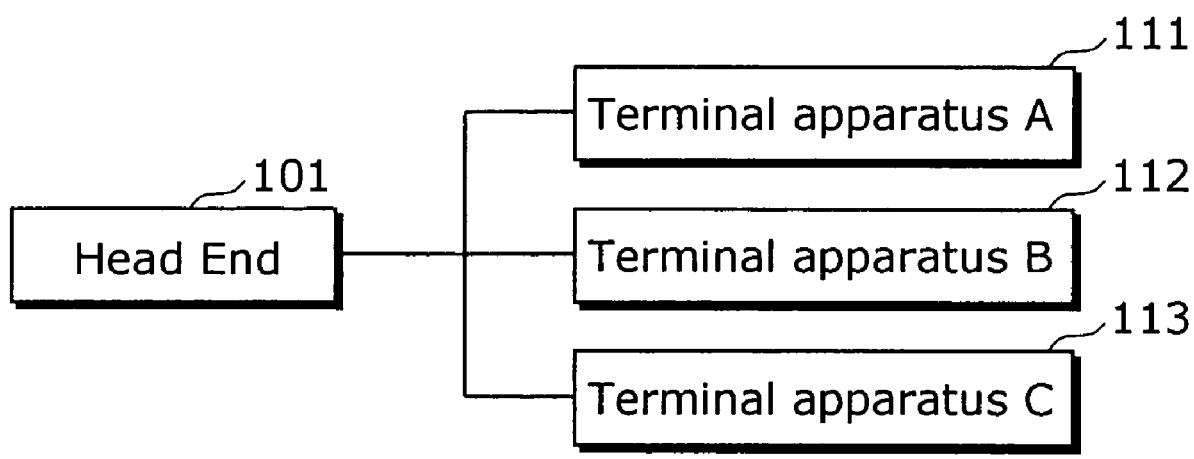
FIG. 1 is a diagram showing a structure of a cable television system according to a first embodiment of the present invention.

An explanation is given of a preferred embodiment of a cable television system according to the present invention with reference to the drawings. FIG. 1 is a block diagram showing the relationship among apparatuses composing the cable system, which are a head end 101, and three terminal apparatuses: a terminal apparatus A111, a terminal apparatus B112, and a terminal apparatus C113. In the present embodiment, three terminal apparatuses are connected to one head end, but it is possible to carry out the present invention if an arbitrary number of terminal apparatuses is/are connected to the head end.

The head end 101 transmits, to plural terminal apparatuses, broadcast signals such as video, audio and data, and receives data transmitted from the terminal apparatuses. In order to realize this, frequency bands are divided for use of data transmission between the head end 101, and the terminal apparatus A111, the terminal apparatus B112, and the terminal apparatus C113. FIG. 2 is a table showing an example of divided frequency bands. There are roughly two types of frequency bands: Out of Band (to be abbreviated as OOB) and In-Band. A frequency band of 5~130 MHz is allocated to OOB to be mainly used for data exchange between the head end 101, and the terminal apparatus A111, the terminal apparatus B112, and the terminal apparatus C113. A frequency band of 130 MHz~864 MHz is allocated to In-Band to be mainly used for broadcast channels including video and audio. QPSK is employed for OOB, whereas QAM64 is employed for In-Band as modulation techniques. A detailed explanation of modulation techniques is omitted here, since they are publicly known techniques which are less related to the present invention. FIG. 3 shows a more specific example of how the OOB frequency band is used. A frequency band of 70 MHz~74 MHz is used to transmit data from the head end 101. In this case, all of the terminal apparatus A111, the terminal apparatus B112, and the terminal apparatus C113 receive the same data from the head end 101. Meanwhile, a frequency band of 10.0 MHz~10.1 MHz is used to transmit data from the terminal apparatus A111 to the head end 101. A frequency band of 10.1 MHz~10.2 MHz is used to transmit data from the terminal apparatus B112 to the head end 101. A frequency band of 10.2 MHz~10.3 MHz is used to transmit data from the terminal apparatus C113 to the head end 101. Accordingly, it becomes possible to transmit data unique to each terminal apparatus to the head end 101 from the terminal apparatus A111, the terminal apparatus B112, and the terminal apparatus C113. FIG. 4 shows an example use of the In-Band frequency band. Frequency bands of 150~156 MHz and 156~162 MHz are allocated respectively to a television channel 1 and a television channel 2, and the subsequent frequencies are allocated to television channels at 6 MHz intervals. 310 MHz and the subsequent frequencies are allocated to radio channels at 1 MHz intervals. Each of the above channels may be used either for analog broadcasting or digital broadcasting. In the case of digital broadcasting, data is transmitted in the transport packet format compliant with the MPEG2 specification, in which case data intended for various data broadcasting systems can be transmitted, in addition to audio and video data.

The head end 101 is equipped with a QPSK modulation unit, a QAM modulation unit, and the like in order to transmit suitable broadcast signals to the respective frequency ranges. Moreover, the head end 101 is equipped with a QPSK demodulation unit for receiving data from the terminal apparatuses. Also, the head end 101 is assumed to be further equipped with various devices related to the above modulation units and demodulation unit. However, a detailed explanation of them is omitted here, since the present invention is mainly related to the terminal apparatuses.

The terminal apparatus A111, the terminal apparatus B112, and the terminal apparatus C113 receive and reproduce broadcast signals transmitted from the head end 101. Furthermore, the terminal apparatus A111, the terminal apparatus B112, and the terminal apparatus C113 transmit data unique to each terminal apparatus to the head end 101. In the present embodiment, these three terminal apparatuses shall have the same configuration.

Figure 5:
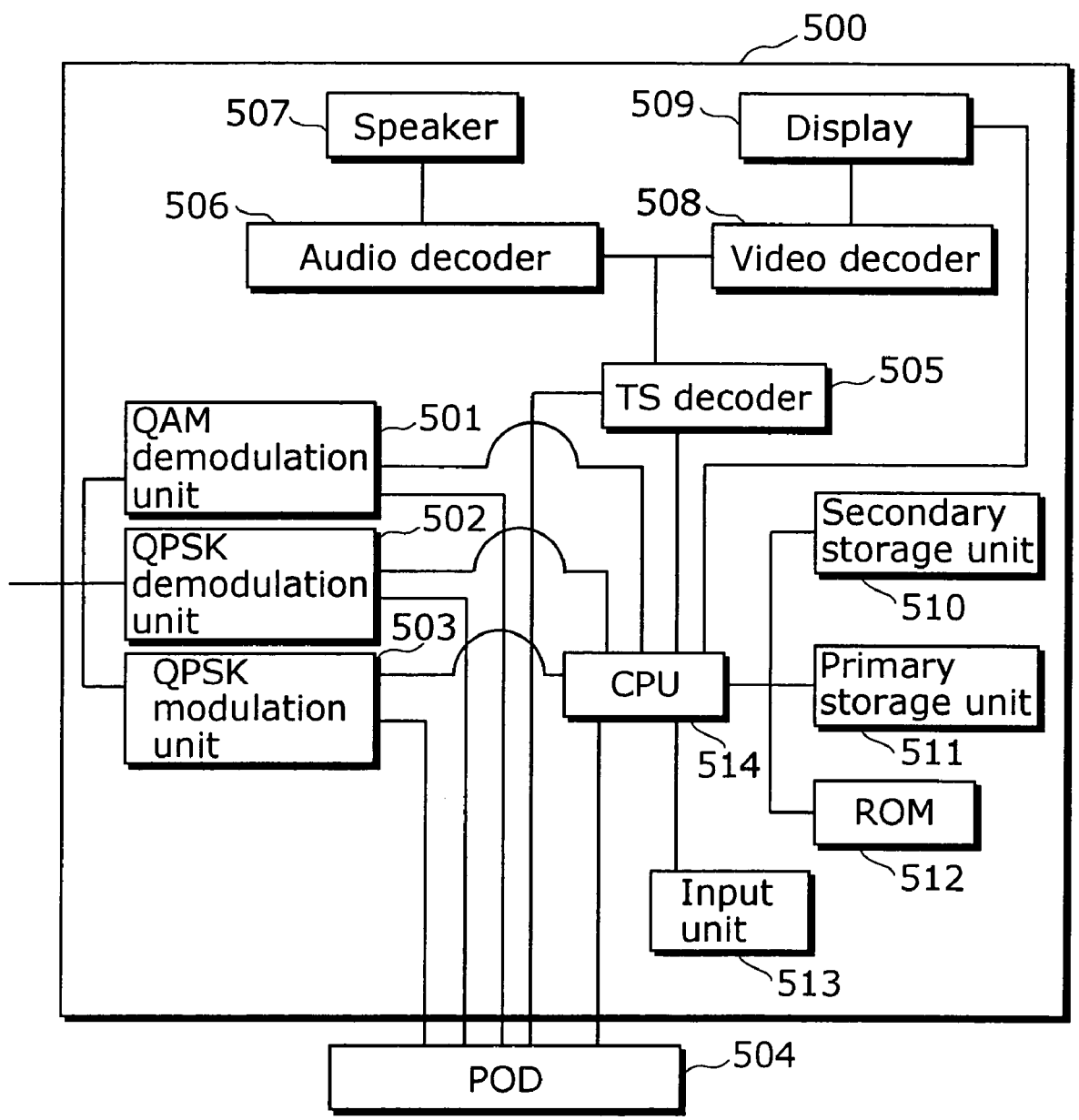
FIG. 5 is a diagram showing a configuration of a terminal apparatus in the cable television system according to the present invention.

FIG. 5 is a block diagram showing a hardware configuration of each terminal apparatus. 500 is a terminal apparatus, which is made up of a QAM demodulation unit 501, a QPSK demodulation unit 502, a QPSK modulation unit 503, a TS decoder 505, an audio decoder 506, a speaker 507, a video decoder 508, a display 509, a secondary storage unit 510, a primary storage unit 511, a ROM 512, an input unit 513, and a CPU 514. Furthermore, a POD 504 can be attached to/detached from the terminal apparatus 500.

Figure 6:
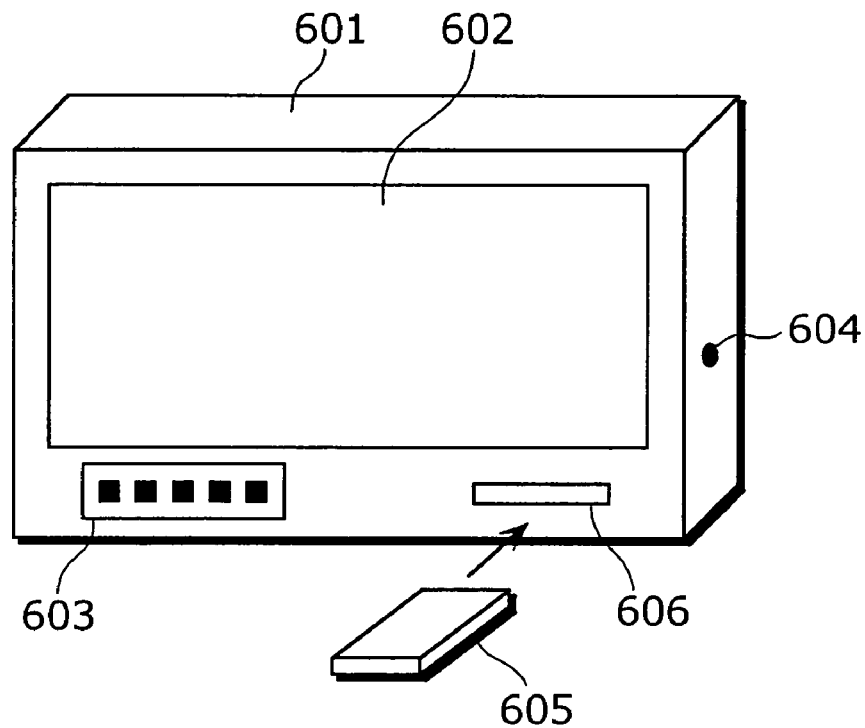
FIG. 6 is a diagram showing an example external view of the terminal apparatus in the cable television system according to the present invention.

FIG. 6 shows a thin-shaped television, which is an example external view of the terminal apparatus 500. The terminal apparatus can come in a variety of configurations, but in the present embodiment, a terminal apparatus that is configured on the basis of OpenCable™ and OCAP is described as an example.

601 is a steel case of the thin-shaped television, in which all components of the terminal apparatus 500 except for the POD 504 are contained.

602 is a display, which corresponds to the display 509 in FIG. 5.

603 is a front panel unit which is made up of plural buttons and which corresponds to the input unit 513 in FIG. 5.

604 is a signal input terminal to which a cable line is connected for transmitting/receiving signals to and from the head end 101. The signal input terminal is connected to the QAM demodulation unit 501, the QPSK demodulation unit 502, and the QPSK modulation unit 503 shown in FIG. 5.

605 is a POD card corresponding to the POD 504 in FIG. 5. The POD 504 is embodied independently of the terminal apparatus 500 and can be attached to/detached from the terminal apparatus 500, as in the case of the POD card 605 in FIG. 6. A detailed explanation of the POD 504 is given later.

606 is an insertion slot into which the POD card 605 is inserted.

Referring to FIG. 5, the QAM demodulation unit 501 demodulates a signal which has been QAM-modulated in and transmitted from the head end 101, according to tuning information that includes a frequency specified by the CPU 514, and passes the resultant to the POD 504.

The QPSK demodulation unit 502 demodulates a signal which has been QPSK-modulated in and transmitted from the head end 101, according to tuning information that includes a frequency specified by the CPU 514, and passes the resultant to the POD 504.

The QPSK modulation unit 503 QPSK-demodulates a signal passed from the POD 504, according to demodulation information that includes a frequency specified by the CPU 514, and transmits the resultant to the head end 101.

As shown in FIG. 6, the POD 504 is detachable from the main body of the terminal apparatus 500. The definition of the connection interface between the main body of the terminal 500 and the POD 504 is given in OpenCable™ CableCARD™ Interface Specification (OC-SP-CC-IF-I15-031121) and in specifications referred to by such specification. Note that CableCARD in such specification refers to a POD. Here, a detailed description is omitted, and an explanation is given only of constituent elements relevant to the present invention.

Figure 7:
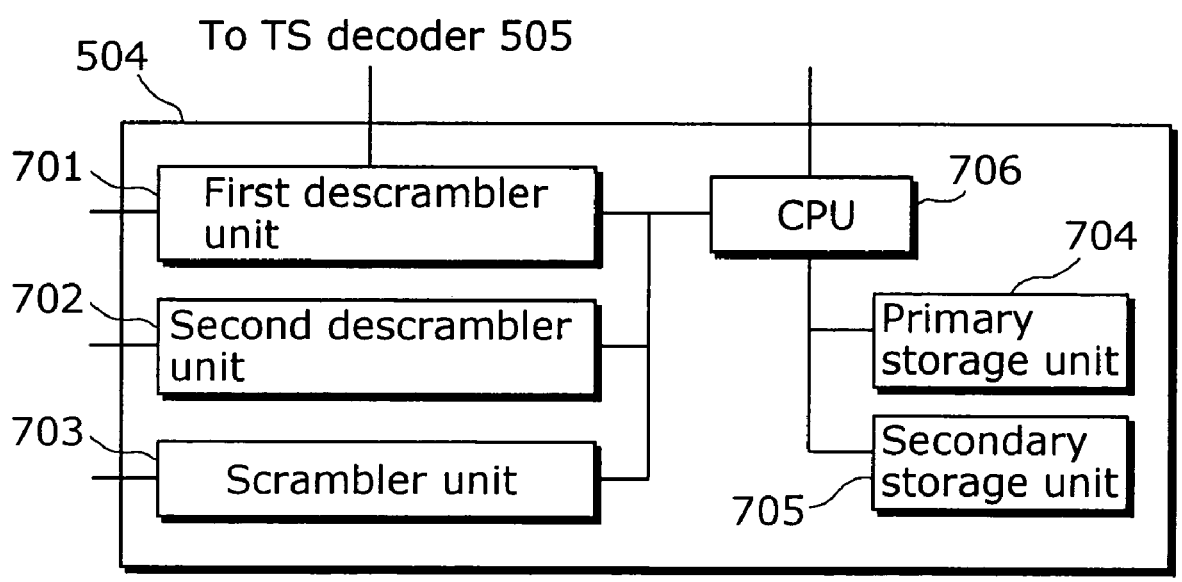
FIG. 7 is a diagram showing a hardware configuration of a POD 504 according to the present invention.

FIG. 7 is a block diagram showing an internal configuration of the POD 504. The POD 504 is made up of a first descrambler unit 701, a second descrambler unit 702, a scrambler unit 703, a primary storage unit 704, a secondary storage unit 705, and a CPU 706.

The first descrambler unit 701 receives a scrambled signal from the QAM demodulation unit 501 of the terminal apparatus 500 under the instruction from the CPU 706, and descrambles such signal. Then, the first descrambler unit 701 transmits the descrambled signal to the TS decoder 505 of the terminal apparatus 500. Information required for descrambler such as a key is provided by the CPU 706 according to need. More specifically, the head end 101 broadcasts several pay channels, and when the user purchased the right to view these pay channels, the first descrambler unit 701 receives required information such as a key from the CPU 706 and performs descrambler. Accordingly, the user can view these pay channels. When required information such as a key is not provided, the first descrambler unit 701 passes the received signal directly to the TS decoder 505 without performing descrambling.

The second descrambler unit 702 receives a scrambled signal from the QPSK demodulation unit 502 of the terminal apparatus 500 under the instruction from the CPU 706, and descrambles such signal. Then, the second descrambler unit 702 passes the descrambled data to the CPU 706.

The scrambler unit 703 scrambles the data received from the CPU 706, under the instruction from the CPU 706, and sends the resultant to the QPSK modulation unit 503 of the terminal apparatus 500.

The primary storage unit 704, a concrete constituent element of which is a primary memory such as a RAM, is intended for storing data temporarily when the CPU 706 performs processing.

The secondary storage unit 705, a concrete constituent element of which is a secondary storage memory such as a flash ROM, is intended for storing a program to be executed by the CPU 706 as well as for storing data which should never be deleted even when the power is turned off.

Figure 8:
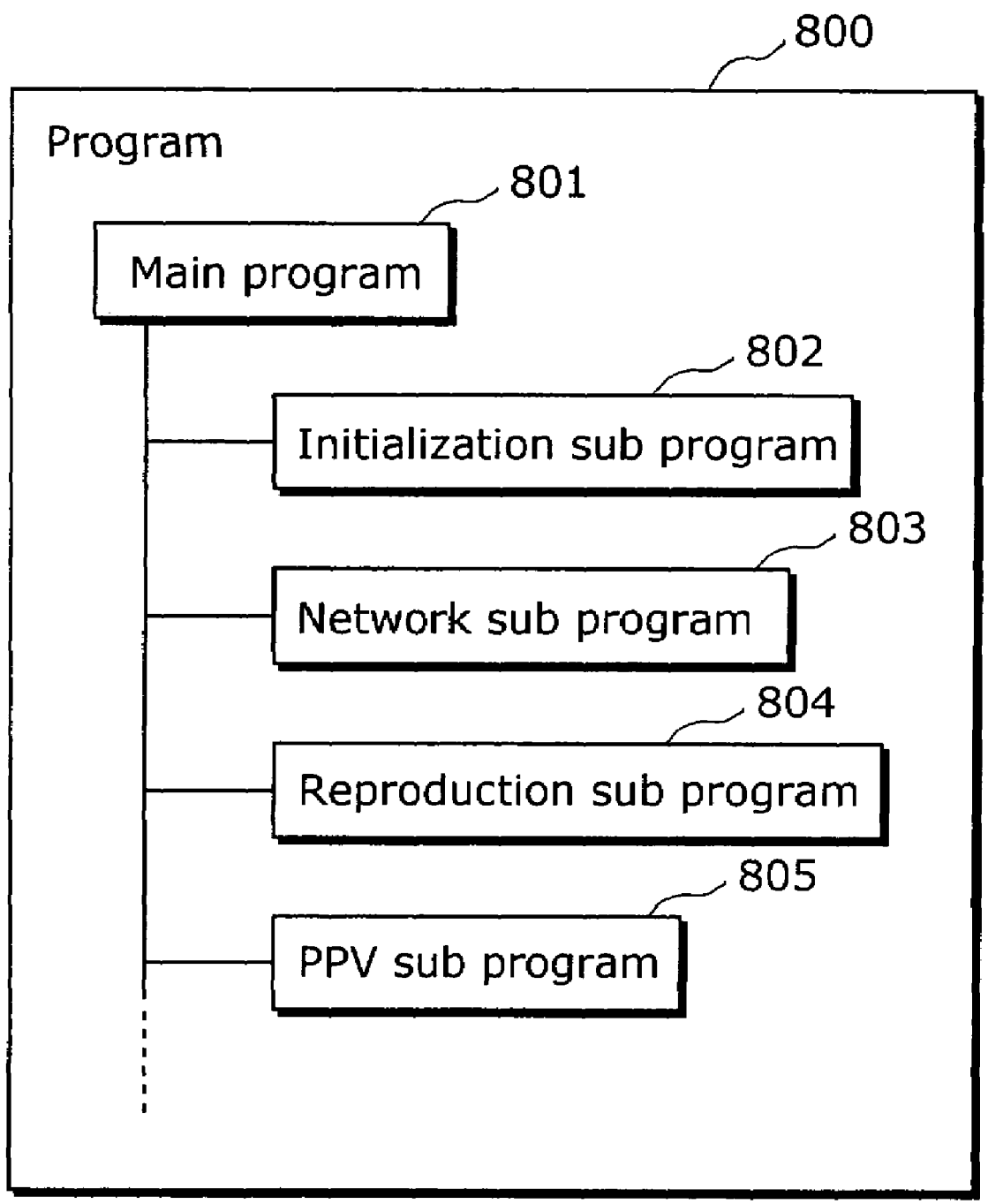
FIG. 8 is a diagram showing a structure of a program stored in the POD 504 according to the present invention.

The CPU 706 executes the program stored in the secondary storage unit 705. The program is made up of plural sub programs. FIG. 8 shows an example of the program stored in the secondary storage unit 705. In FIG. 8, a program 800 is made up of plural sub programs including a main program 801, an initialization sub program 802, a network sub program 803, a reproduction sub program 804, and a PPV sub program 805.

Here, PPV, which is an abbreviation of Pay Per View, refers to a service that allows the user to view a certain program such as a movie on a chargeable basis. When the user enters his/her personal identification number, the fact that the user purchased the right to view the program is notified to the head end 101, and the program is descrambled. Accordingly, the user can view such program. This viewing of the program requires the user to pay for the purchase at later date.

The main program 801, which is the sub program activated by the CPU 706 first of all when the power is turned on, controls the other sub programs.

The initialization sub program 802, which gets activated by the main program 801 when the power is turned on, carries out information exchange and the like with the terminal apparatus 500 to perform initialization processing. This initialization processing is defined in detail in OpenCable™ Cable-CARD™ Interface Specification (OC-SP-CC-IF-I15-031121) and in specifications referred to by such specification. Furthermore, the initialization sub program 802 also performs initialization processing not defined in these specifications. Here, a part of such initialization processing is introduced. When the power is turned on, the initialization sub program 802 notifies the QPSK demodulation unit 502 of a first frequency stored in the secondary storage unit 705 via the CPU 514 of the terminal apparatus 500. The QPSK demodulation unit 502 performs tuning using the provided first frequency, and transmits the resulting signal to the secondary scrambler unit 702. Moreover, the initialization sub program 802 provides the secondary descrambler unit 702 with descrambling information such as a first key stored in the secondary storage unit 705. As a result, the secondary descrambler unit 702 performs descrambling and passes the resultant to the CPU 706 executing the initialization sub program 802. Accordingly, the initialization sub program 802 can receive the information. In the present embodiment, the initialization sub program 802 receives information via the network sub program 803. A detailed description on this is given later.

Furthermore, the initialization sub program 802 notifies the QPSK modulation unit 503 of a second frequency stored in the secondary storage unit 705 via the CPU 514 of the terminal apparatus 500. The initialization sub program 802 provides the scrambler unit 703 with scrambling information stored in the secondary storage unit 705. When the initialization sub program 802 provides, via the network sub program 803, the scrambler unit 703 with information required to be sent, the scrambler unit 703 scrambles the data using the provided scrambling information, and provides the scrambled data to the QPSK modulation unit 503. The QPSK modulation unit 503 modulates the scrambled information which it received, and sends the modulated information to the head end 101.

As a result, it becomes possible for the initialization sub program 802 to carry out a two way communication with the head end 101 via the terminal apparatus 500, the secondary descrambler unit 702, the scrambler unit 703, and the network sub program 803.

The network sub program 803, which is used by plural sub programs such as the main program 801 and the initialization sub program 802, is a sub program intended for carrying out a two way communication with the head end 101. More specifically, the network sub program 803 behaves as if other sub programs using the network sub program 803 were carrying out a two way communication with the head end 101 in accordance with TCP/IP. A detailed explanation of TCP/IP is omitted here, since it is a publicly known technique that specifies the protocols to be used when exchanging information between plural terminals. When activated by the initialization sub program 802 at power-on time, the network sub program 803 notifies, via the terminal apparatus 500, the head end 101 of an MAC address (an abbreviation of Media Access Control) which is an identifier for identifying the POD 504 and which is stored in the secondary storage unit 705 beforehand, so as to request for obtaining an IP address. The head end 101 notifies the POD 504 of the IP address via the terminal apparatus 500, and the network sub program 803 stores such IP address in the primary storage unit 704. From then on, the head end 101 and the POD 504 communicate with each other using such IP address as the identifier of the POD 504.

The reproduction sub program 804 provides the first descrambler unit 701 with descrambling information such as a second key stored in the secondary storage unit 705 as well as descrambling information such as a third key provided by the terminal apparatus 500, so as to allow descrambling to be performed. Furthermore, the reproduction sub program 804 receives, via the network sub program 803, information indicating that the signal inputted in the first descrambler unit 701 is a PPV channel. On the notification that the signal is a PPV channel, the reproduction sub program 804 activates the PPV sub program 805.

When activated, the PPV sub program 805 displays, on the terminal apparatus 500, a message that prompts the user to purchase the program, and accepts an input from the user. More specifically, when information wished to be displayed on the screen is sent to the CPU 514 of the terminal apparatus 500, a program running on the CPU 514 of the terminal apparatus 500 shows the message on the display 509 of the terminal apparatus 500. Then, when the user enters the personal identification number via the input unit 513 of the terminal apparatus 500, the CPU 514 of the terminal apparatus 500 accepts it, and sends it to the PPV sub program 805 running on the CPU 706 of the POD 504. The PPV sub program 805 sends, to the head end 101, the accepted personal identification number via the network sub program 803. When such personal identification number is valid, the head end 101 notifies, via the network sub program 803, the PPV sub program 805 of descrambling information required for descrambling such as a fourth key. The PPV sub program 805 provides the first descrambler unit 701 with the accepted descrambling information such as the fourth key, and then the first descrambler unit 701 descrambles the input signal.

Figure 9:
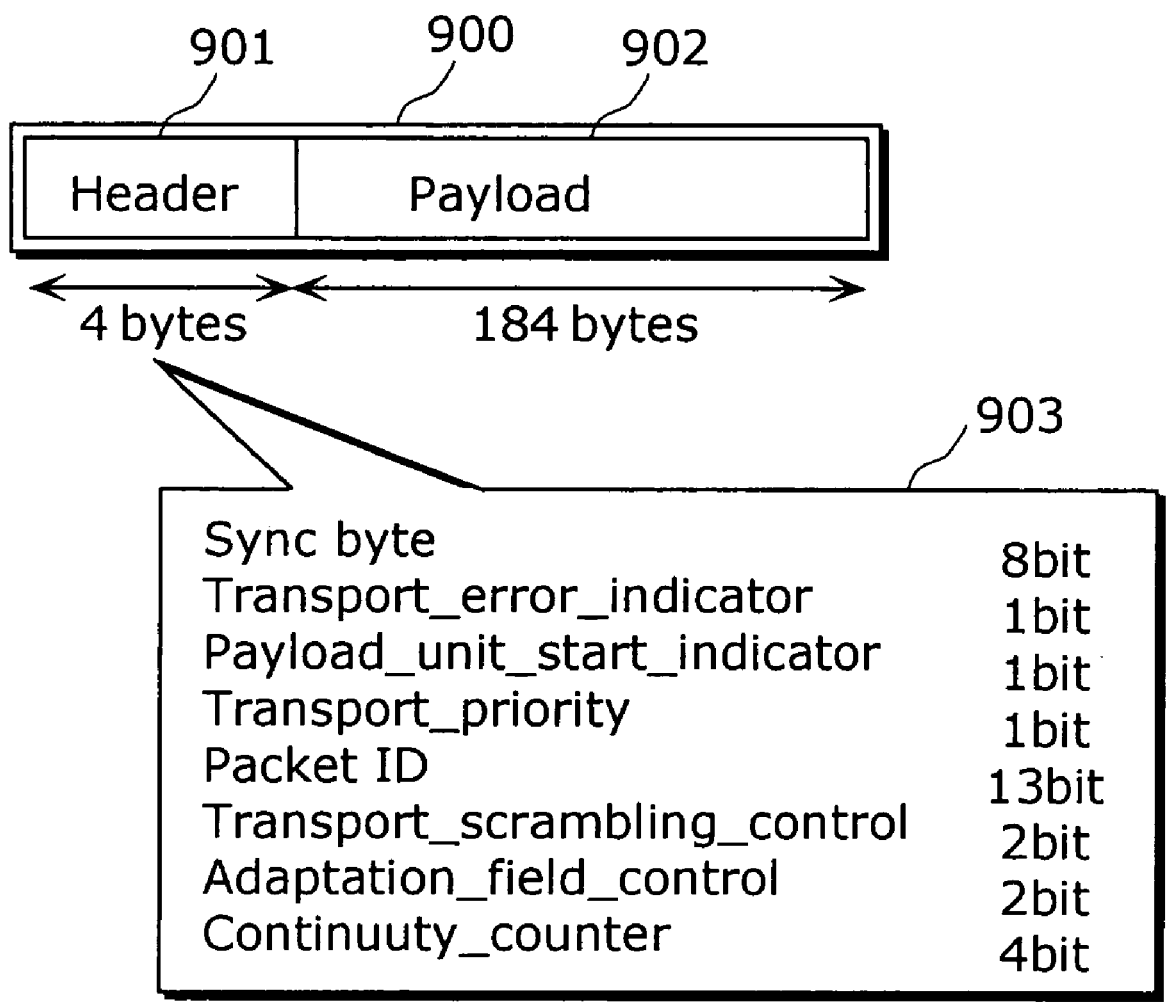
FIG. 9 is a diagram showing a structure of a packet defined in the MPEG standard.
Figure 10:
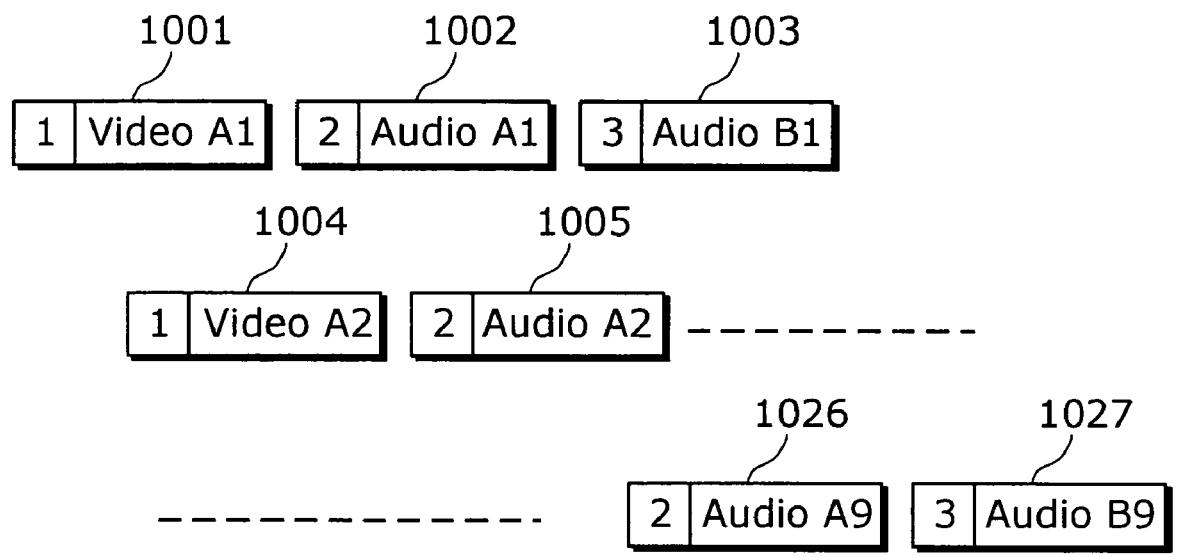
FIG. 10 is a diagram showing an example of an MPEG2 transport stream.

Referring to FIG. 5, the TS decoder 505 performs filtering on the signal accepted from the POD 504, and passes necessary data to the audio decoder 506, the video decoder 508, and the CPU 514. Here, the signal sent from the POD 504 is an MPEG2 transport stream. A detailed description about an MPEG2 transport stream is given in the MPEG specification ISO/IEC138181-1, and therefore it is not explained in detail in the present embodiment. An MPEG2 transport stream is composed of plural fixed length packets, and a packet ID is assigned to each packet. FIG. 9 is a diagram showing the structure of a packet. 900 is a packet, which contains fixed length 188 bytes. The top four bytes is a header 901 storing information for identifying the packet, and the other 184 bytes is a payload 902 storing information wished to be carried. 903 shows the breakdown of the header 901. A packet ID is included in 13 bits from the $1^{st}$ to the $12^{th} \sim 24^{th}$ bit. FIG. 10 is a schematic diagram illustrating plural packet strings to be transmitted. A packet 1001 contains a packet ID "1" in its header and includes the first information of video A in its payload. A packet 1002 contains a packet ID "2" in its header and includes the first information of audio A in its payload. A packet 1003 contains a packet ID "3" in its header and includes the first information of audio B in its payload.

A packet 1004 contains the packet ID "1" in its header and includes the second information of the video A in its payload, which is the subsequent information of the packet 1001. Similarly, packets 1005, 1026, and 1027 carry subsequent data of the other packets. By concatenating the contents of the payloads of packets with the same packet IDs in the above manner, it is possible to reproduce video and audio in successive order.

Refer to FIG. 10. When the CPU 514 indicates, to the TS decoder 505, the packet ID "1" as well as "the video decoder 508" as an output destination, the TS decoder 505 extracts packets with the packet ID "1" from the MPEG2 transport stream received from the POD 504, and passes them to the video decoder 508. In FIG. 10, therefore, only the video data is passed over to the video decoder 508. At the same time, when the CPU 514 indicates, to the TS decoder 505, the packet ID "2" as well as "the audio decoder 506", the TS decoder 505 extracts packets with the packet ID "2" from the MPEG2 transport stream received from the POD 504, and passes them to the audio decoder 506. In FIG. 10, only the audio data is passed over to the video decoder 508.

This processing of extracting only necessary packets according to packet IDs corresponds to filtering to be performed by the TS decoder 505. The TS decoder 505 is capable of performing more than one filtering processing simultaneously at the instruction from the CPU 514.

Referring to FIG. 5, the audio decoder 506 concatenates audio data embedded in the packets in the MPEG2 transport stream provided by the TS decoder 505, performs digital-to-analog conversion on the concatenated data, and outputs the resultant to the speaker 507.

The speaker 507 outputs the signal provided by the audio decoder 506 as audio.

The video decoder 508 concatenates video data embedded in the packets in the MPEG2 transport stream provided by the TS decoder 505, performs digital-to-analog conversion on the concatenated data, and outputs the resultant to the display 509.

The display 509, a concrete constituent element of which is a CRT or a liquid crystal and the like, outputs a video signal provided by the video decoder 508 and displays a message specified by the CPU 514, and so forth.

The secondary storage unit 510, concrete constituent elements of which are a flash memory, a hard disk, and the like, stores and deletes data and programs specified by the CPU 514. Stored data and programs are referred to by the CPU 514. The stored data and programs are kept in storage even while the terminal apparatus 500 is powered off.

The primary storage unit 511, concrete constituent elements of which are a RAM and the like, temporarily stores data and programs specified by the CPU 514 and deletes them. Stored data and programs are referred to by the CPU 514. The stored data and programs are deleted when the terminal apparatus 500 gets powered off.

The ROM 512 is a read-only memory device, concrete constituent elements of which are a ROM, a CD-ROM, and a DVD, and the like. The ROM 512 stores a program to be executed by the CPU 514.

Figure 11:
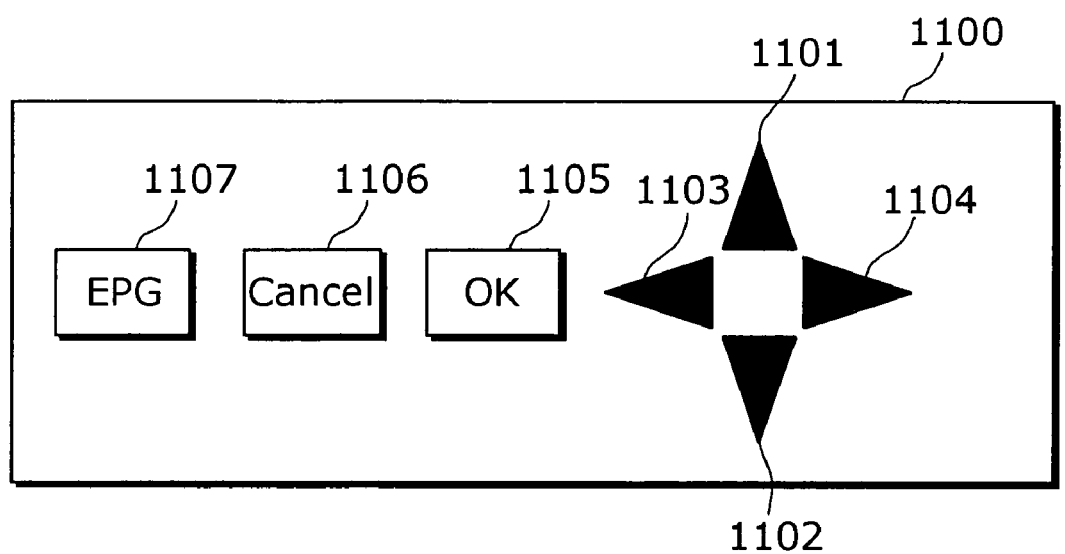
FIG. 11 is a diagram showing an example external view of an input unit 513 in the case where it is configured in the form of a front panel.

The input unit 513, concrete constituent elements of which are a front panel or a remote controller, accepts an input from the user. FIG. 11 shows an example of the input unit 513 in the case where it is configured in the form of a front panel. 1100 is a front panel, which corresponds to the front panel unit 603 shown in FIG. 6. Such front panel 1100 is made up of seven buttons: an up-cursor button 1101, a down-cursor button 1102, a left-cursor button 1103, a right-cursor button 1104, an OK button 1105, a cancel button 1106, and an EPG button 1107. When the user presses down a button, the identifier of such pressed button is notified to the CPU 514.

The CPU 514 executes the program stored in the ROM 512. According to instructions from such program to be executed, the CPU 514 controls the QAM demodulation unit 501, the QPSK demodulation unit 502, the QPSK modulation unit 503, the POD 504, the TS decoder 505, the display 509, the secondary storage unit 510, the primary storage unit 511, and the ROM 512.

Figure 12:
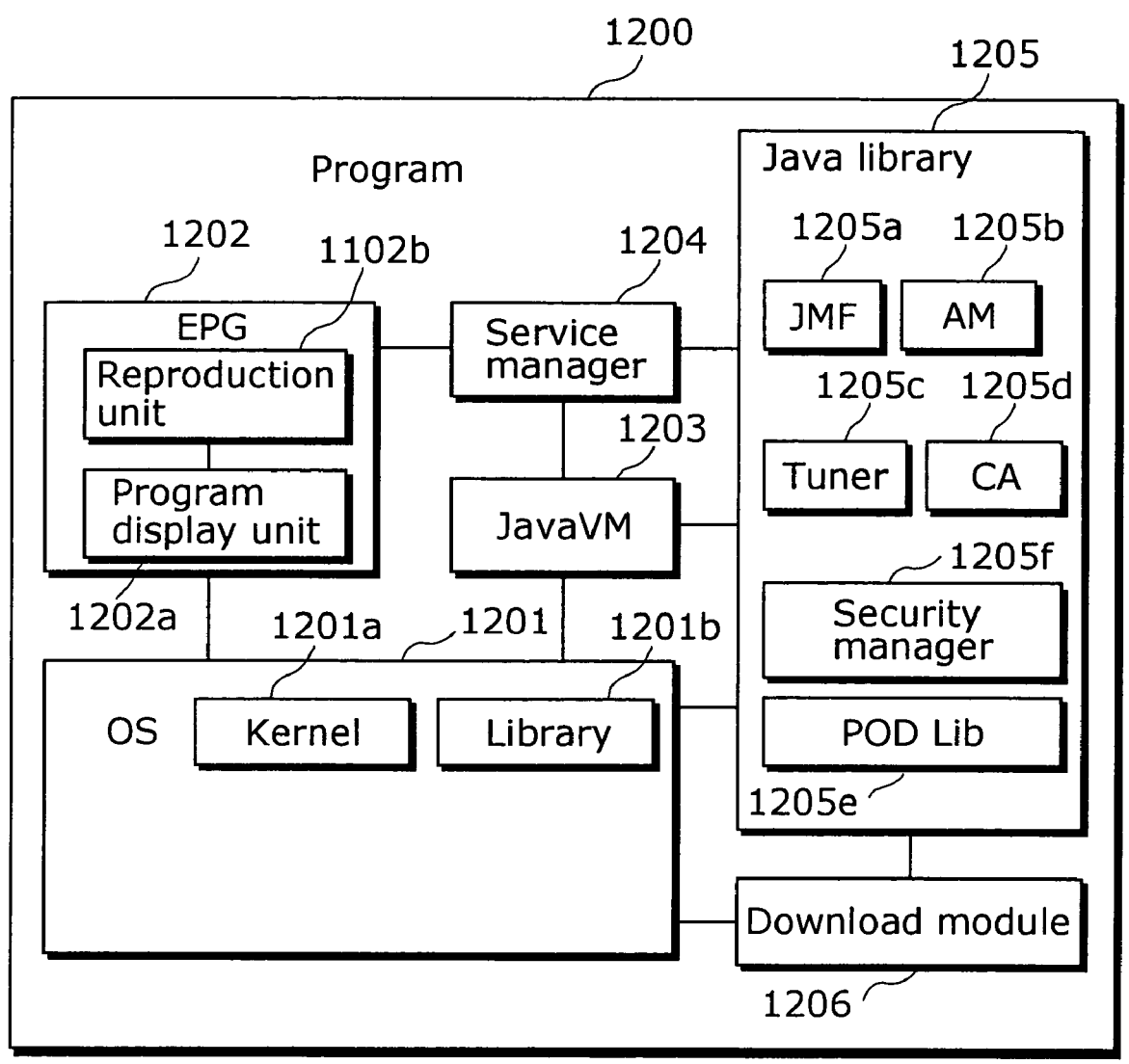
FIG. 12 is a diagram showing a structure of the program stored in a terminal apparatus 500 according to the present invention.

FIG. 12 is a diagram showing an example structure of the program that is stored in the ROM 512 and executed by the CPU 514.

A program 1200 is made up of plural sub programs. To be more specific, the program 1200 is made up of an OS 1201, an EPG 1202, a JavaVM 1203, a service manager 1204, and a Java library 1205.

The OS 1201 is a sub program to be activated by the CPU 514 when the terminal apparatus 500 is powered on. The OS 1201 is an abbreviation of operating system, an example of which is Linux and the like. The OS 1201 is a generic name for a publicly known art made up of a kernel 1201a for executing a sub program in parallel with another sub program and of a library 1201b, and therefore a detailed explanation is omitted. In the present embodiment, the kernel 1201a of the OS 1201 executes the EPG 1202 and the JavaVM 1203 as sub programs. Meanwhile, the library 1201b provides these sub programs with plural functions required for controlling the constituent elements of the terminal apparatus 500.

Here, tuning is introduced as an example of such functions. With the function of tuning, tuning information including a frequency is received from another sub program and then passed over to the QAM demodulation unit 501. Accordingly, it is possible for the QAM demodulation unit 501 to perform demodulation based on the provided tuning information, and pass the demodulated data to the POD 504. As a result, the other sub programs can control the QAM demodulation unit via the library 1201b.

Figure 13A:
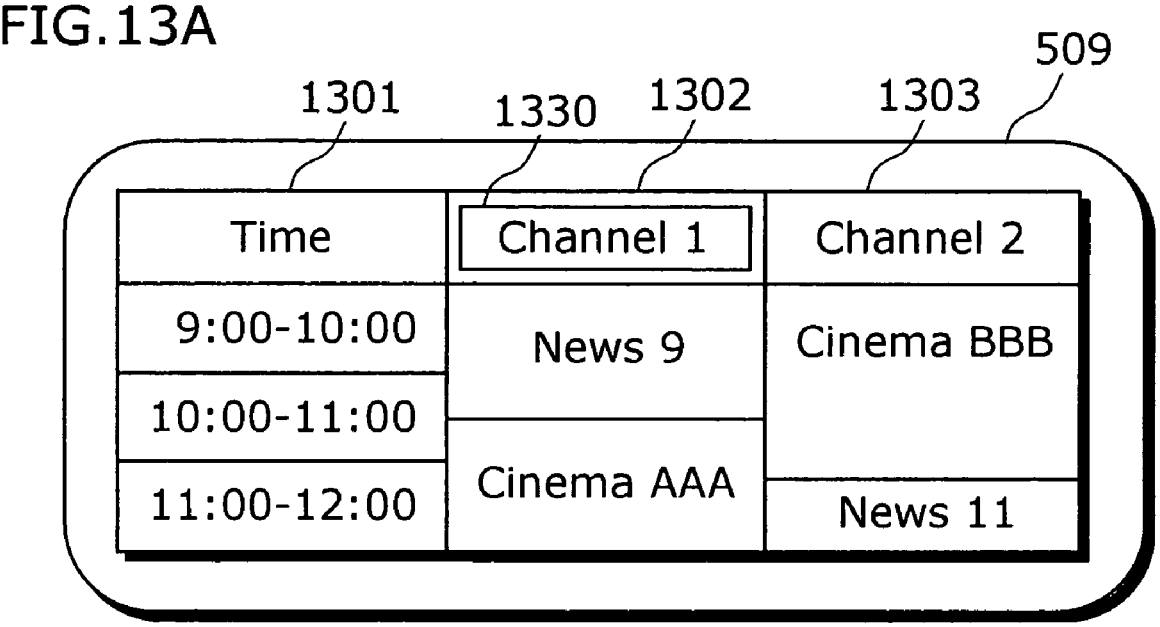
FIG. 13A is a diagram showing an example of a display screen displayed by a display 509 according to the present invention.
Figure 13B:
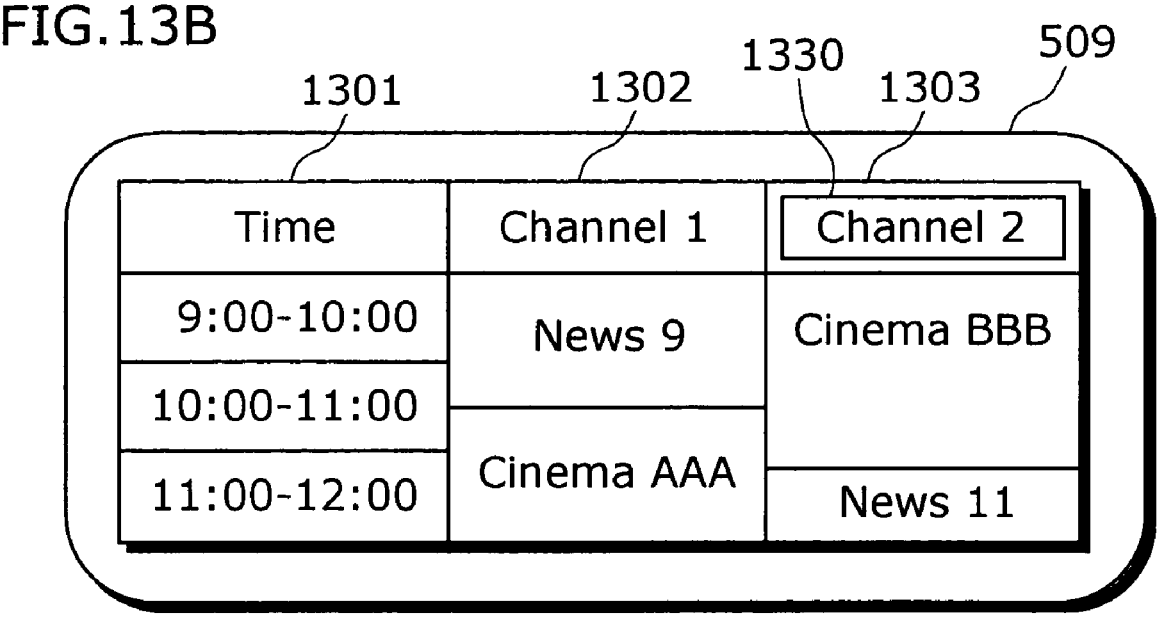
FIG. 13B is a diagram showing an example of a display screen displayed by the display 509 according to the present invention.

The EPG 1202 is made up of a program display unit 1202a for displaying a list of programs to the user as well as for accepting an input from the user, and a reproduction unit 1102b for selecting channels. Here, EPG is an abbreviation of Electric Program Guide. The EPG 1202 gets activated when the terminal apparatus 500 is powered on. In the activated EPG 1202, the program display unit 1202a waits for an input from the user via the input unit 513 of the terminal apparatus 500. Here, in the case where the input unit 513 takes a form of the front panel illustrated in FIG. 11, when the user presses down the EPG button 1107 on the input unit 513, the CPU 514 is notified of the identifier of such EPG button. The program display unit 1202a of the EPG 1202, which is a sub program running on the CPU 514, accepts this identifier, and shows program information on the display 509. FIG. 13A and FIG. 13B show examples of a program table displayed on the display 509. See FIG. 13A. The Program information is displayed on the display 509 in a grid pattern. A column 1301 describes time information. A column 1302 describes a channel name "Channel 1" and programs to be broadcast during time periods corresponding to the respective times described in the column 1301. It is shown that a program "News 9" is broadcast from 9:00 to 10:30, and "Cinema AAA" is broadcast from 10:30 to 12:00 on "Channel 1". A column 1303 describes a channel name "Channel 2" and programs to be broadcast during time periods corresponding to the respective times described in the column 1301, as in the case of the column 1302. A program "Cinema BBB" is broadcast from 9:00 to 11:00, and "News 11" is broadcast from 11:00 to 12:00. 1330 is a cursor. The cursor 1330 moves at the press of the left-cursor 1103 or the right-cursor 1104 on the front panel 1100. When the right-cursor 1104 is pressed down in the state illustrated in FIG. 13A, the cursor 1330 moves toward right as shown in FIG. 13B. Meanwhile, when the left-cursor 1103 is pressed down in the state illustrated in FIG. 13B, the cursor 1330 moves toward left as shown in FIG. 13A.

When the OK button 1105 on the front panel 1100 is pressed down in the state shown in FIG. 13A, the program display unit 1202a notifies the reproduction unit 1102b of the identifier of "Channel 1". Meanwhile, when the OK button 1105 on the front panel 1100 is pressed down in the state shown in FIG. 13B, the program display unit 1202a notifies the reproduction unit 1102b of the identifier of "Channel 2".

Furthermore, the program display unit 1202a periodically stores program information to be displayed from the head end 101 into the primary storage unit 511 via the POD 504. Generally, it takes time to obtain program information from the head end. However, it becomes possible to quickly display a program table by displaying the program information that is pre-stored in the primary storage unit 511 at the press of the EPG button 1107 of the input unit 513.

Figure 14:
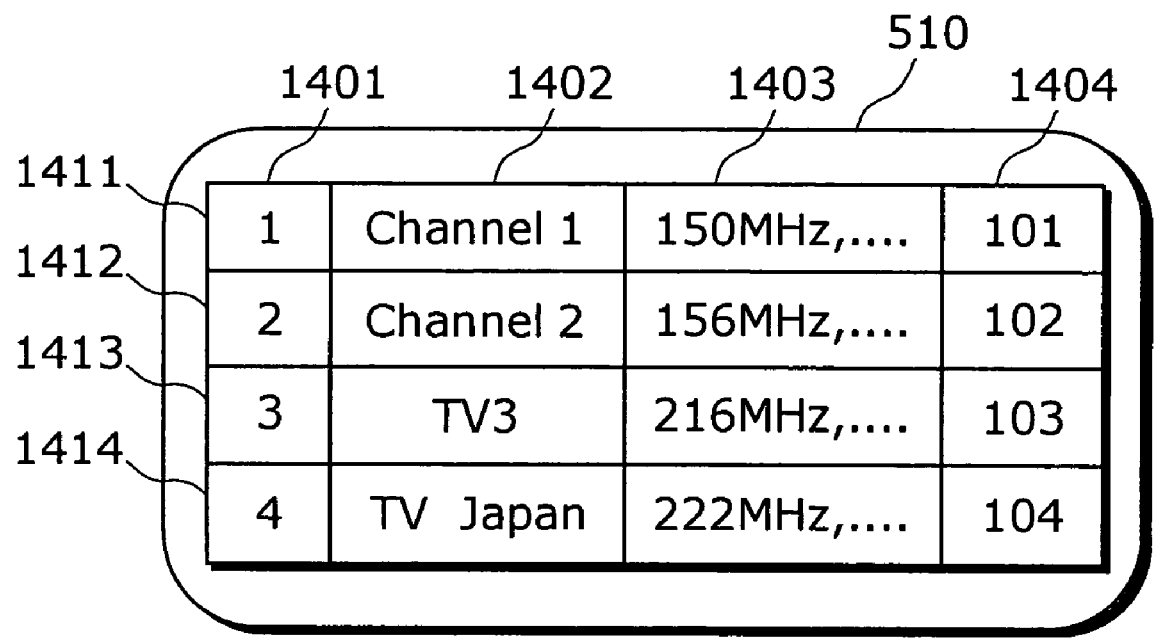
FIG. 14 is a diagram showing an example of information stored in a secondary storage unit 510 according to the present invention.

The reproduction unit 1102b reproduces the channel using the received identifier of the channel. The relationship between channel identifiers and channels is pre-stored by the secondary storage unit 510 as channel information. FIG. 14 shows an example of the channel information stored in the secondary storage unit 510. The channel information is stored in tabular form. A column 1401 describes the identifiers of channels. A column 1402 describes channel names. A column 1403 describes tuning information. Here, the tuning information is represented by values to be provided to the QAM demodulation unit 501 such as frequency, transmission rate, and coding ratio. A column 1404 describes program numbers. Program numbers are numbers used to identify PMTs defined by the MPEG2 standard. A description about PMT is given later. Each of lines 1411~1414 indicates a set of the identifier, channel name, and tuning information of each channel. The line 1411 describes a set that includes "1" as an identifier, "Channel 1" as a channel name, a frequency of "312 MHz" as tuning information, and "101" as a program number. The reproduction unit 1102b passes the identifier of the received channel directly to the service manager in order to reproduce the channel.

Figure 15A:
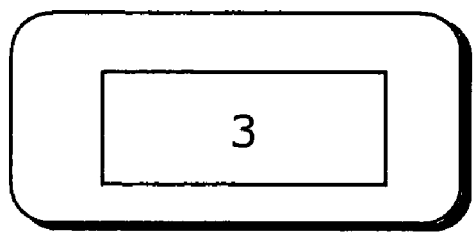
FIGS. 15A, 15B, and 15C are diagrams, each showing an example of information stored in a primary storage unit 511 according to the present invention.
Figure 15B:
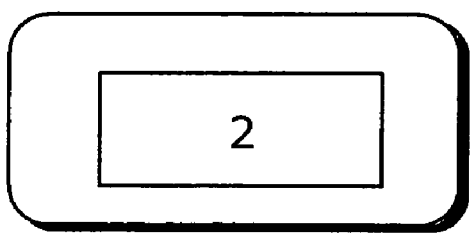
Figure 15C:
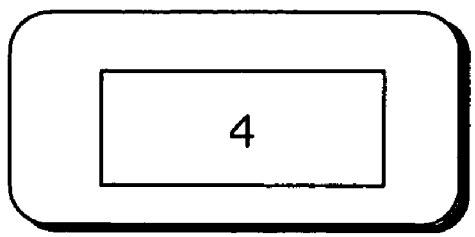

Moreover, when the user presses down the up-cursor 1101 and the down-cursor 1102 on the front panel 1100 while the reproduction is taking place, the reproduction unit 1102b receives a notification about such press by the user from the input unit 513 via the CPU 514, and switches the channel being reproduced to another one. First, the reproduction unit 1102b stores, in the primary storage unit 511, the identifier of the channel that is currently reproduced. FIGS. 15A, B, and C show example identifiers of channels stored in the primary storage unit 511. FIG. 15A shows that an identifier "3" is stored, and it is shown by referring to FIG. 14 that a channel with the channel name "TV 3" is being reproduced. When the user presses down the up-cursor 1101 in a state illustrated in FIG. 15A, the reproduction unit 1102b refers to the channel information shown in FIG. 14, and passes the identifier "2" of a channel with the channel name of "Channel 2" to the service manager in order to newly reproduce a channel with the channel name of "Channel 2", which is the previous channel in the table. At the same time, the reproduction unit 1102b rewrites the identifier into the channel identifier "2" stored in the primary storage unit 511. FIG. 15B shows such rewritten channel identifier. Meanwhile, when the user presses down the down-cursor 1102 in the state illustrated in FIG. 15A, the reproduction unit 1102b refers to the channel information shown in FIG. 14, and passes the identifier "4" of a channel with the channel name of "TV Japan" to the service manager in order to newly reproduce a channel with the channel name of "TV Japan", which is the next channel in the table. At the same time, the reproduction unit 1102b rewrites the identifier into the channel identifier "4" stored in the primary storage unit 511. FIG. 15C shows such rewritten channel identifier.

The JavaVM 1203 is a Java virtual machine that sequentially analyzes and executes programs written in the Java™ language. Programs written in the Java language are compiled into intermediate codes known as byte codes which do not depend on hardware. The Java virtual machine is an interpreter that executes such byte codes. Some of the Java virtual machines translate the byte codes into an executable form which can be interpreted by the CPU 514 and pass the resultant to the CPU 514, which executes it. The JavaVM 1203 gets activated, with a Java program to be executed being specified by the kernel 1201a. In the present embodiment, the kernel 1201a specifies the service manager 1204 as a Java program to be executed. A detailed commentary on the Java language is given in many books that include "Java Language Specification" (ISBN 0-201-63451-1). Therefore, a detailed description about it is omitted here. Also, a detailed commentary on the operation of the Java VM itself is given in many books that include "Java Virtual Machine Specification" (ISBN 0-201-63451-X). Therefore, a detailed description about it is omitted here.

The service manager 1204, which is a Java program written in the Java language, is executed by the JavaVM 1203 sequentially. It is possible for the service manager 1204 to call and to be called by another sub program not written in the Java language through the JNI (Java Native Interface). A commentary on the JNI is given in many books that include "Java Native Interface". Therefore, a detailed description about it is omitted here.

The service manager 1204 accepts the identifier of the channel from the reproduction unit 1102b through the JNI.

First, the service manager 1204 passes the identifier of the channel to a Tuner 1205c in the Java library 1205 so as to request for tuning. The Tuner 1205c refers to the channel information stored in the secondary storage unit 510 to obtain the tuning information. Assuming that the service manager 1204 passes the identifier "2" of the channel to the Tuner 1205c, the Tuner 1205c refers to the column 1412 shown in FIG. 14, and obtains the tuning information "156 MHz," corresponding to the channel. The Tuner 1205c passes the tuning information to the QAM demodulation unit 501 via the library 1201b of the OS 1201. The QAM demodulation unit 501 demodulates the signal sent from the head end 101 according to the tuning information given to the QAM demodulation unit 501, and passes the resultant signal to the POD 504.

Next, the service manager 1204 requests a CA 1205b inside the lava library 1205 to perform descrambling. The CA 1205d provides the POD 504 with information required for descrambling through the library 1201b in the OS 1201. On the basis of such provided information, the POD 504 descrambles the signal provided by the QAM demodulation unit 501, and passes the resultant signal to the TS decoder 505.

Next, the service manager 1204 provides a JMF 1205a inside the Java library 1205 with the identifier of the channel, so as to request for the reproduction of the video and audio.

Figure 16:
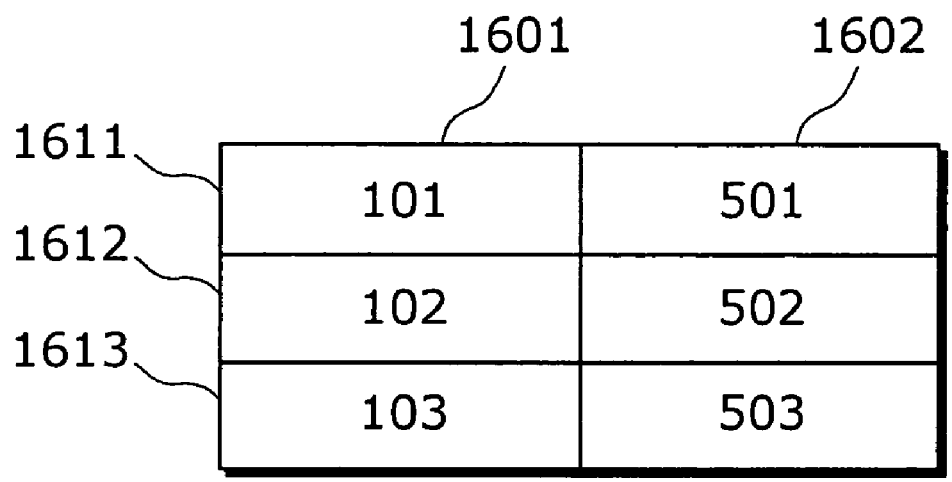
FIG. 16 is a schematic diagram showing the contents of a PAT specified in the MPEG2 standard according to the present invention.
Figure 17:
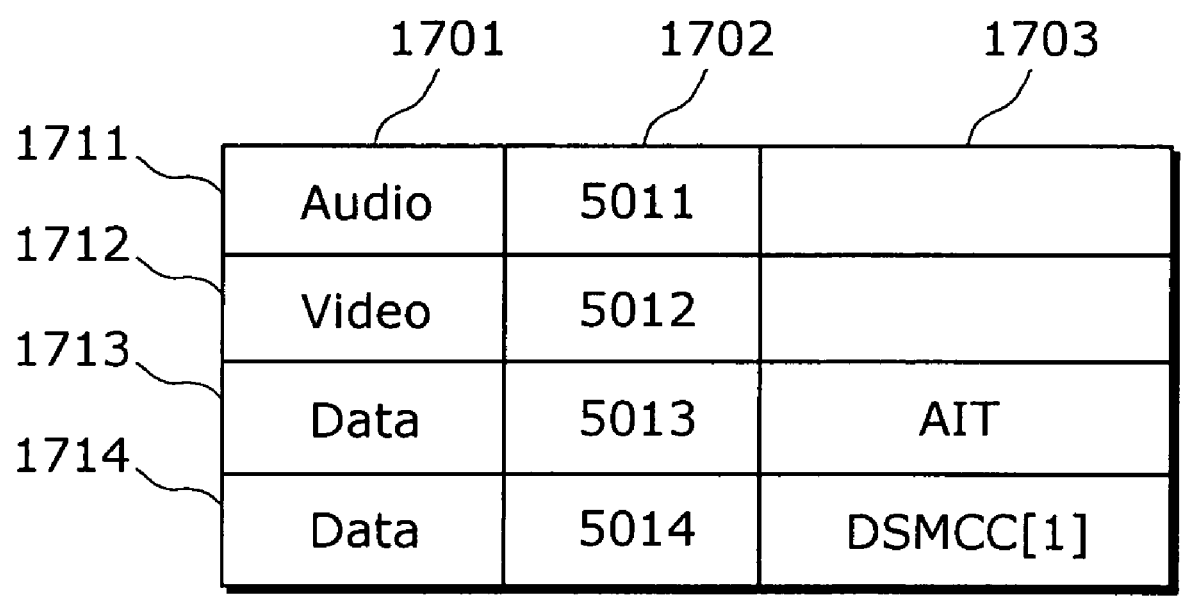
FIG. 17 is a schematic diagram showing the contents of a PMT specified in the MPEG2 standard according to the present invention.

First, the JMF 1205a obtains, from a PAT and a PMT, packet IDs used to specify the video and audio to be reproduced. PAT and PMT are tables defined by the MPEG-2 standard that show the program line-up included in an MPEG2 transport stream. PAT and PMT are carried in the payloads in packets included in an MPEG2 transport stream, together with audio and video. Refer to the specification for a detailed description of PAT and PMT. Here, only an overview of PAT and PMT is given. PAT, which is an abbreviation of Program Association Table, is carried in packets with the packet ID "0". In order to obtain the PAT, the JMF 1205*a* indicates, to the TS decoder 505, the packet ID "0" and the CPU 514 through the library 1201*b* of the OS 1201. Then, the TS decoder 505 performs filtering based on the packet ID "0", and passes the resultant to the CPU 514. Accordingly, the JMF 1205*a* can collect the PAT packets. FIG. 16 illustrates a table that schematically shows an example of the collected PAT information. A column 1601 describes program numbers. A column 1602 describes packet IDs. The packet IDs shown in the column 1602 are used to obtain the PAT. Each of lines 1611~1613 is a pair of the program number of a channel and a packet ID corresponding to it. Here, three channels are defined. The line 1611 defines a pair of the program number "101" and the packet ID "501". Assuming that the channel identifier provided to the JMF 1205*a* is "2", the JMF 1205*a* refers to the column 1412 in FIG. 14, so as to obtain the program number "102" corresponding to such channel identifier, and then refers to the line 1612 in the PAT shown in FIG. 16, so as to obtain the packet ID "502" corresponding to the program number "102". PMT, which is an abbreviation of Program Map Table, is carried in packets with the packet IDs specified in the PAT. In order to obtain the PMT, the JMF 1205*a* indicates, to the TS decoder 505, a packet ID and the CPU 514 through the library 1201*b* of the OS 1201. Here, a packet ID to be specified is "502". Then, the TS decoder 505 performs filtering based on the packet ID "502", and passes the resultant to the CPU 514. Accordingly, the JMF 1205*a* can collect the PMT packets. FIG. 17 illustrates a table that schematically shows an example of the collected PMT information. A column 1701 describes stream types. A column 1702 describes packet IDs. Information specified in the respective stream types is carried in the payloads of packets with the packet IDs specified in the column 1702. A column 1703 describes additional information. Each of lines 1711~1714 is a pair of a packet ID and the type of information being transmitted, which is known as an elementary stream. The line 1711, which is a pair of the stream type "audio" and the packet ID "5011", indicates that audio data is stored in the payload of the packet with the packet ID "5011". The JMF 1205*a* obtains, from the PMT, the packet IDs of the video and audio to be reproduced. Referring to FIG. 17, the JMF 1205*a* obtains the audio packet ID "5011" from the line 1711, and the video packet ID "5012" from the line 1712.

Then, the JMF 1205*a* provides the TS decoder 505 with pairs of the obtained audio packet ID and the audio decoder 506 as an output destination as well as the video packet ID and the video decoder 508 as an output destination, via the library 1201*b* of the OS 1201. The TS decoder 505 performs filtering based on such provided packet IDs and the output destinations. Here, the packet with the packet ID "5011" is passed to the audio decoder 506 and the packet with the packet ID "5012" is passed to the video decoder 508. The audio decoder 506 performs digital-to-analog conversion on the provided packet, so as to reproduce the audio via the speaker 507. The video decoder 508 performs digital-to-analog conversion on the provided packet, so as to display the video on the display 509.

Finally, the service manager 1204 provides the channel identifier to an AM 1205*b* in the Java library 1205, so as to request for data broadcast reproduction. Here, data broadcast reproduction means to extract a Java program included in the MPEG2 transport stream and cause the JavaVM 1203 to execute it. As a technique for embedding a Java program into an MPEG2 transport stream, a method known as DSMCC is used, which is described in the MPEG specification ISO/IEC138181-6. A detailed explanation of DSMCC is omitted here. DSMCC specification defines a method of encoding a file system comprised of directories and files used by a computer, in packets within an MPEG2 transport stream. Information about the Java program to be executed is carried in packets in the MPEG2 transport stream in the form of AIT. AIT is an abbreviation of Application Information Table whose definition is given in the tenth chapter of the DVB-MHP standard (formally known as ETSI TS 101 812 DVB-MHP specification V1.0.2).

First, in order to obtain the AIT, the AM 1205*b* obtains the PAT and PMT as in the case of the JMF 1205*a*, so as to obtain the packet ID of the packet that stores the AIT. Assuming that "2" is the provided channel identifier and that the PAT shown in FIG. 16 and the PMT shown in FIG. 17 are being transmitted, the AM 1205*b* obtains the PMT shown in FIG. 17 according to the same procedure followed by the JMF 1205*a*. Subsequently, the AM 1205*b* extracts, from the PMT, the packet ID of the elementary stream whose stream type is "Data" and which has "AIT" as additional information. As shown in FIG. 17, the elementary stream in the line 1713 corresponds to such elementary stream, and therefore the AM 1205*b* obtains the packet ID "5013" from it.

Figure 18:
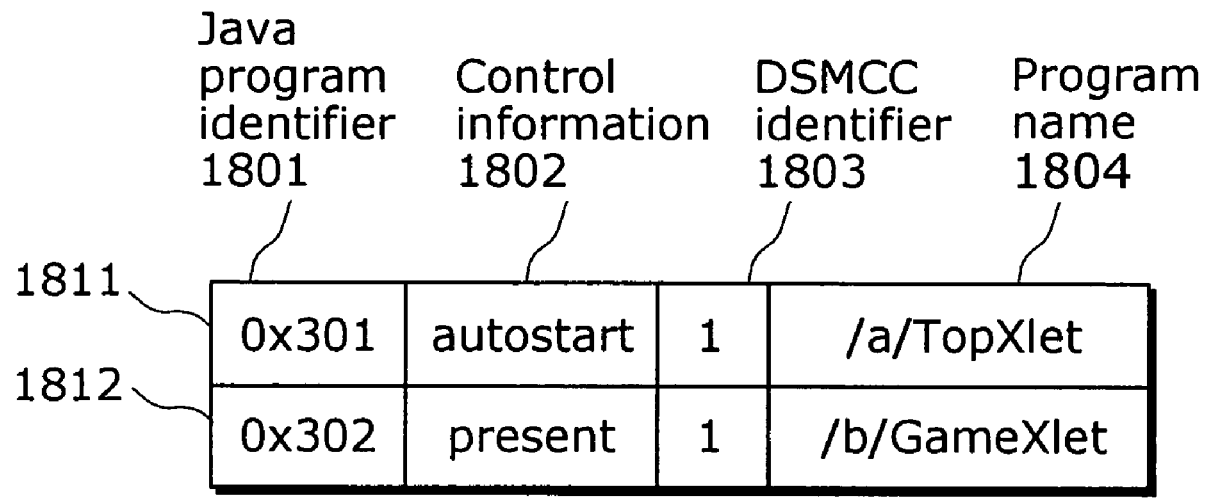
FIG. 18 is a schematic diagram showing the contents of an AIT specified in the DVB-MHP standard according to the present invention.

The AM 1205*b* provides the TS decoder 505 with the packet ID of the AIT and the CPU 514 as an output destination through the library 1201*b* of the OS 1201. Then, the TS decoder 505 performs filtering based on such provided packet ID, and passes the resultant to the CPU 514. Accordingly, the AM 1205*b* can collect the packets of AIT. FIG. 18 is a table that schematically shows an example of the collected AIT information. A column 1801 describes identifiers of Java programs. According to the MHP specification, these identifiers are defined as Application IDs, which identify whether a Java program is a program that should be authenticated by a security manager 1205*f* of the terminal apparatus 500. No authentication is required when the value of an identifier is in the range of 0x0 to 0x3fff, while authentication is required when the value of an identifier is in the range of 0x4000 to 0x7fff. A Java program whose identifier value falls within the former range is referred to as "unsigned program" and a Java program whose identifier value falls within the latter range is referred to as "signed program". A column 1802 describes control information for controlling the Java programs. The control information includes "autostart", "present", and "kill". "autostart" means that the terminal apparatus 500 automatically executes the program promptly. "present" means that the program is not executed automatically. "kill" means that the program is to be terminated. A column 1803 describes DSMCC identifiers used to extract packet IDs that include Java programs in the DSMCC format. A column 1804 describes program names of the Java programs. Each of lines 1811 and 1812 is a set of information about a Java program. The Java program defined in the line 1811 is a set of an identifier "301", control information "autostart", a DSMCC identifier "1", and a program name "a/TopXlet". The Java program defined in the line 1812 is a set of an identifier "302", control information "present", a DSMCC identifier "1", and a program name "b/GameXlet". Here, these two Java programs have the same DSMCC identifier. This indicates that two Java programs are included in the file system which has been encoded according to the same DSMCC method. Here, only four pieces of information are specified for the respective Java programs, but more pieces of information are specified in actuality. Refer to the DVB-MHP specification for detail.

The AM 1205*b* finds the "autostart" Java program from the AIT, and extracts the corresponding DSMCC identifier and Java program name. Referring to FIG. 18, the AM 1205*b* extracts the Java program in the line 1811, and obtains the DSMCC identifier "1" and the Java program name "a/TopXlet".

Next, the AM 1205b obtains, from the PMT, the packet ID of packets that store Java programs in the DSMCC format, using the DSMCC identifier obtained from the AIT. More specifically, the AM 1205b obtains, from the PMT, the packet ID included in the elementary stream whose stream type is "Data" and whose DSMCC identifier in the additional information matches.

Here, assuming that such DSMCC identifier is "1" and the PMT is the one shown in FIG. 17, the elementary stream in the line 1714 satisfies the above condition. Therefore, the packet ID "5014" is to be extracted.

The AM 1205b indicates, to the TS decoder 505, the packet ID of packets in which data is embedded in the DSMCC format as well as the CPU 514 as an output destination through the library 1201b of the OS 1201. Here, the packet ID "5014" is provided. Then, the TS decoder 505 performs filtering based on the provided packet ID, and passes the resultant to the CPU 514. Accordingly, the AM 1205b can collect the required packets. The AM 1205b reconstructs the file system from the collected packets according to the DSMCC method, and stores the reconstructed file system into the primary storage unit 511. The process for extracting data such as the file system from packets in the MPEG2 transport and storing the extracted data into storage units such as the primary storage unit 511 is hereinafter called download.

Figure 19:
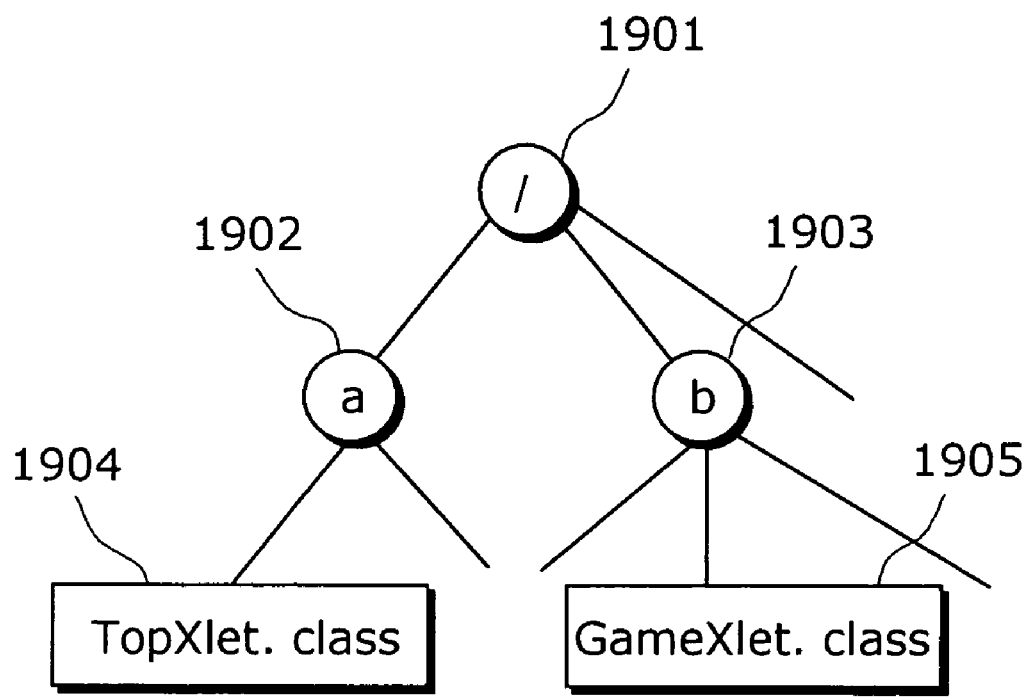
FIG. 19 is a schematic diagram showing a file system to be transmitted in the DSMCC format according to the present invention.

FIG. 19 shows an example of the downloaded file system. In the diagram, circles represent directories and squares represent files, where 1901 is a root directory, 1902 is a directory "a", 1903 is a directory "b", 1904 is a file "TopXlet. class", and 1905 is a file "GameXlet. class".

Subsequently, the AM 1205b passes, to the JavaVM 1203, a Java program to be executed out of the file system downloaded into the primary storage unit 511. Here, assuming that the Java program name to be executed is "a/TopXlet", a file "a/TopXlet. class" resulted from appending ". class" to the above Java program name is a file to be executed. "/" is a delimiter between a directory and a file name, and as shown in FIG. 19, the file 1904 is a Java program to be executed. Next, the AM 1205b passes the file 1904 to the JavaVM 1203 since the column 1801 describing the identifier of the Java program indicates unsigned program, meaning that there is no need to request the security manager 1205f to perform authentication of such Java program.

The JavaVM 1203 executes such received Java program.

Upon the receipt of the identifier of another channel, the service manager 1204 terminates the reproduction of the video and audio as well as the execution of the Java program which are being carried out through each library included in the Java library 1205, through each library included in the same Java library 1205, and then performs the reproduction of the video and audio as well as the execution of a Java program based on the newly received channel identifier.

The Java library 1205 is a collection of plural Java libraries stored in the ROM 512. In the present embodiment, the Java library 1205 includes the JMF 1205a, the AM 1205b, the Tuner 1205c, the CA 1205d, a POD Lib 1205e, the security manager 1205f, a download module 1206, and the like.

The service manager 1204 and the download module 1206 carry out a two way communication with the head end 101 via the POD Lib 1205e included in the Java library 1205. This two way communication can be realized by the POD Lib 1205e using the QPSK demodulation unit 502 and the QPSK modulation unit 503 via the library 1201b of the OS 1201 and the POD 504.

Figure 37:
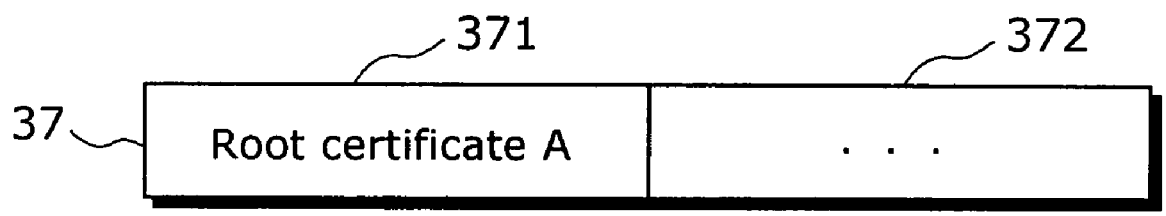
FIG. 37 is a diagram showing a simplified structure of a code file to be received from a download module according to the present invention.

The download module 1206 can receive code data from the head end 101 through this communication. Code data refers to binary data that includes an X. 509 certificate and/or firmware of the terminal apparatus 500. FIG. 37 is a schematic diagram showing code data that describes only a part related to the present invention. When receiving code data 37, the download module 1206 extracts a root certificate 371 if it is included, and passes it to the security manager 1205f. 372 indicates other data such as firmware.

The AM 1205b receives, from the head end 101, information about Java programs which the terminal apparatus 500 should store in the secondary storage unit 510. Such information is referred to as XAIT information. The XAIT information is transmitted between the head end 101 and the POD 504 in an arbitrary form. The present invention can be carried out regardless of transmission format, as long as information required as XAIT is included.

FIG. 20 illustrates a table that schematically shows an example of the XAIT information obtained from the head end 101. A column 2001 describes the identifiers of Java programs. A column 2002 describes control information for controlling the Java programs. The control information includes "autostart" and "present". "autostart" means that the program is executed automatically when the terminal apparatus 500 is powered on, and "present" means that the program is not to be executed automatically. A column 2003 describes DSMCC identifiers used to extract packet IDs that include Java programs in the DSMCC format. A column 2004 describes the program names of the Java programs. A column 2005 describes the priorities of the Java programs. Each of lines 2011 and 2012 is a set of information about the respective Java programs. The Java program defined in the line 2011 is a set of an identifier "0x7001", control information "autostart", a DSMCC identifier "1", and a program name "a/PPV1Xlet". It can be known from its Java program Application ID that this Java program is a signed program. Here, only five pieces of information are specified for the respective Java programs, but the present invention can be carried out even when more pieces of information are defined.

Figure 21:
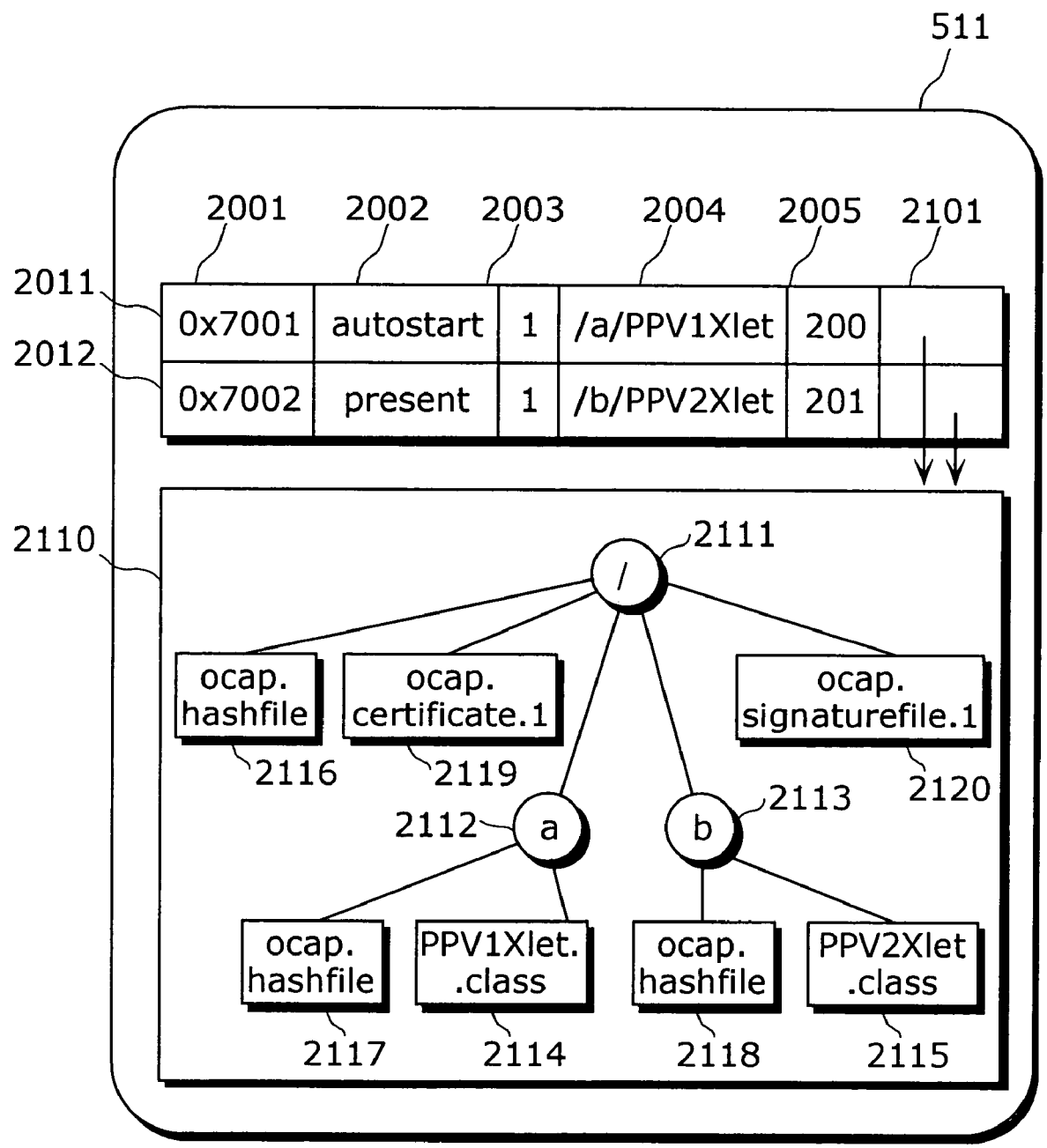
FIG. 21 is a diagram showing an example of information stored in the secondary storage unit 510 according to the present invention.

On the receipt of the XAIT information, the AM 1205b stores the file system from the MPEG2 transport stream into the primary storage unit 511, according to the same procedure as the one for downloading the Java program from the AIT information. After this, the AM 1205b performs a pre-storage notification to the security manager 105f immediately before it stores the file system into the secondary storage unit 510. At this time, an authentication operation is initiated by the security manager 1205f according to the present invention, but its details are described later. Upon notification from the security manager 1205f that the activation is enabled, the AM 1205b stores the file system into the secondary storage unit 510. Next, the AM 1205b stores, into the secondary storage unit 510, the result of associating the XAIT information with a storage position of the downloaded file system. FIG. 21 shows an example of the XAIT information and the downloaded file system stored in the secondary storage unit 510 in association with each other. Here, a file defined in the OCAP specification is described as an example. Elements in FIG. 21 which are the same as those in FIG. 20 are the same as each other, and therefore an explanation for such elements is omitted. A column 2101 stores the storage position of the downloaded file system. In FIG. 21, such storage positions are indicated by arrows. 2110 is the downloaded file system, in which a top directory 2111, a directory "a" 2112, a directory "b" 2113, a file "PPV1Xlet. class" 2114, a file "PPV2Xlet.

class" 2115, files "ocap. hashfile" 2116~2118, a file "ocap. certificate. 1" 2119, and a file "ocap. signaturefile. 1" 2120 are included.

The files 2116~2118 are hash files in which file names or directory names and the corresponding hash values are included. FIGS. 22A, 22B, and 22C are schematic diagrams that show the details of "ocap. hashfiles". 221 in FIG. 22A shows "ocap. hashfile" 2116, 222 in FIG. 22B shows "ocap. hashfile" 2117, and 223 in FIG. 22C shows "ocap. hashfile" 2118. The "ocap. hashfile" of 221, which exists in the "/" directory 2111, includes, in the column 2211, an "ocap. certificate. 1" file 2119, an "ocap. signaturefile. 1" file 2120, an "a" directory 2112, and a "b" directory 2113 that exist in the same directory 2111. A column 2212 indicates which hash algorithm was used to calculate each value described in a column 2213. The column 2213, which relates to the files or directories in the column 2211, includes hash values that were calculated by use of the hash algorithm specified in the column 2212. Currently, hash algorithms that are mainly used are SHA1 (Secure Hash Algorithm 1) and MD5 (Message Digest 5). These are publicly known algorithms for converting data with an arbitrary length into a fixed-length byte value, which have the following features: it is impossible to predict the original data after it is converted; and they are used to check if a file has been destroyed or tampered with. Meanwhile, a hash value is a pseudo random number that is generated by use of a hash algorithm. When a hash algorithm is SHA1, the length of a hash value is 20 bytes, whereas when a hash algorithm is MD5, the length of a hash value is converted into 16 bytes. For details about SHA1 and MD5, refer to "FIPS-PUB 186-2 Secure Hash Standard" and "IETF RFC1321", respectively. Here, hash values that correspond to the respective directories "a" and "b" described in the column 2211 are SHA1 hash values that have been calculated respectively for the "ocap. hashfile" file 2117 existing in the "a" directory and the "ocap. hashfile" file 2118 existing in the "b" directory.

As in the case of the "ocap. hashfile" in 221, "ocap. hashfile" in 222 includes the file name, hash algorithm, and hash value of a "PPV1Xlet. class" file 2114 that exists in the same directory 2112. Similarly, included in 223 are the file name, hash algorithm, and hash value of a "PPV2Xlet. class" file 2115 that exists in the same directory 2113.

Here, only attributes that are related to the present invention are described, and thus the OCAP specification "OpenCable™ Application Platform Specification OCAP 1.0 Profile (OC-SP-OCAP1.0-IF-I09-031121)" should be referred to for details about "ocap. hashfile".

Figure 23:
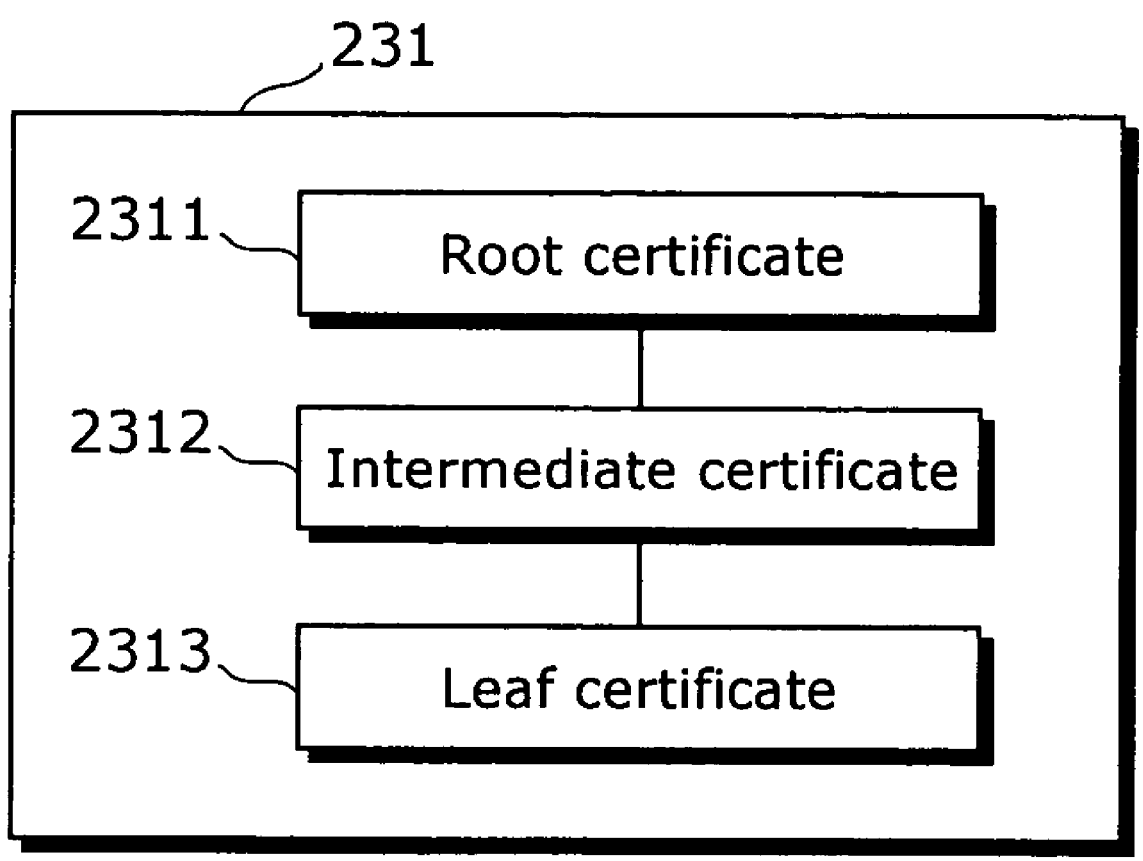
FIG. 23 is a diagram showing a structure of a certificate chain according to the present invention.

A file 2119 is a certificate chain. FIG. 23 is a diagram showing a detailed structure of the "ocap. certificate. 1" file 2119. 231, which depicts a typical structure of "ocap. certificate. x" (x is a positive integer), contains a root certificate 2311, an intermediate certificate 2312, and a leaf certificate 2313. They are in a chain relationship in which the holder of the root certificate 2311 issues the intermediate certificate 2312 and the holder of the intermediate certificate 2312 issues the leaf certificate 2313, for example. Note that according to the OCAP specification, a certificate chain related to a signature file "ocap. signaturefile. x" is "ocap. certificate. x" having the same value "x". In the case of FIG. 21, a certificate chain that corresponds to the "ocap. signaturefile. 1" is the "ocap. certificate. 1". Also, the root certificate 2311, the intermediate certificate 2312, and the leaf certificate 2313 are configured in the same X. 509 certificate format. X. 509 certificates are widely used in various fields in the information and communications industry as a de facto standard for certificate representation format, as a recommendation of ITU-T. In FIG. 23, only three certificates are illustrated, but there is a case where there exist a plurality of intermediate certificates. In this case, however, these intermediate certificates must be in a chain state in which they are related to each other.

Figure 24:
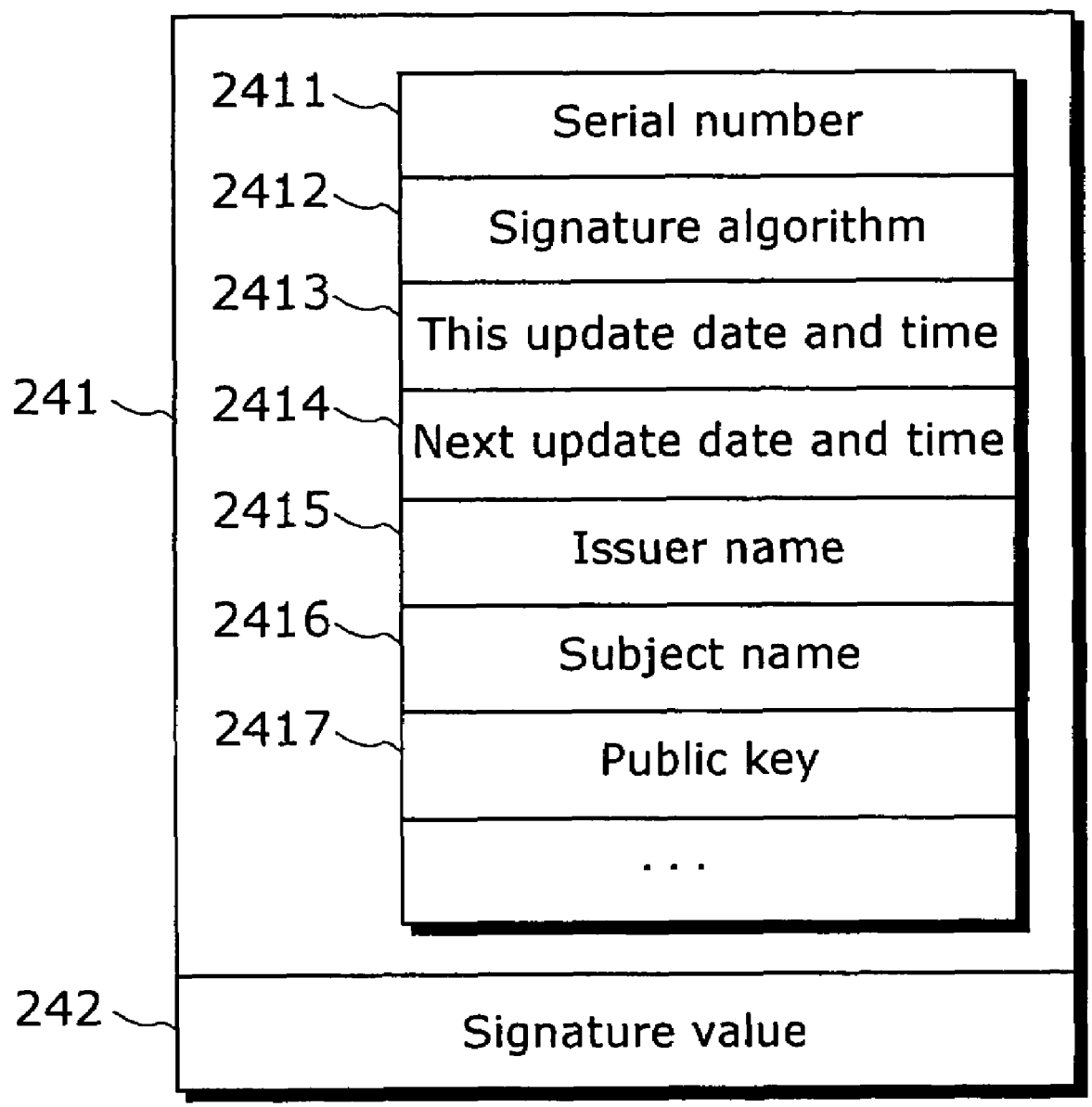
FIG. 24 is a diagram showing a structure of an X. 509 certificate according to the present invention.

FIG. 24 is a diagram showing the structure of an X. 509 certificate. Here, only the attributes that are required for explaining the present invention are illustrated. For details about X. 509 certificates, refer to IETF RFC3280 "Internet X. 509 Public Key Infrastructure Certificate and CRL Profile". 241 indicates an attribute area of the X. 509 certificate and 242 indicates the signature value of the X. 509 certificate. Serial number 2411 indicates the number to identify the certificate, signature algorithm 2412 indicates the algorithm used to determine the signature value 242, this update date and time 2413 indicates the date and time when this X. 509 certificate becomes valid, next update date and time 2414 indicates the date and time when this X. 509 certificate expires, issuer name 2415 indicates the name of the authority that issued this X. 509 certificate, subject name 2416 indicates the holder of this X. 509 certificate, public key 2417 indicates the public key of the subject name 2416, and signature value 242 indicates a value that has been signed (encrypted) with the private key of the issuer of this X. 509 certificate. In this embodiment, this update date and time 2413 and the next update date and time 2414 need information of date and time, but this update date and time 2413 and the next update date and time 2414 do not always need information of time. As a system utilizing public key and private key, public key cryptosystems are widely used for electronic commerce and others. In a public key cryptosystem, an encrypted text is decrypted with a key that is different from the key used to encrypt the plaintext. Since the key for encryption and the key for decryption are different, it is impossible to estimate the key for encryption from the key for decryption. This key for encryption corresponds to the private key and this key for decryption corresponds to the public key. Representative examples of public key cryptosystems include RSA (Rivest-Shamir-Adleman) and DSA (Digital Signature Standard).

Figure 25:
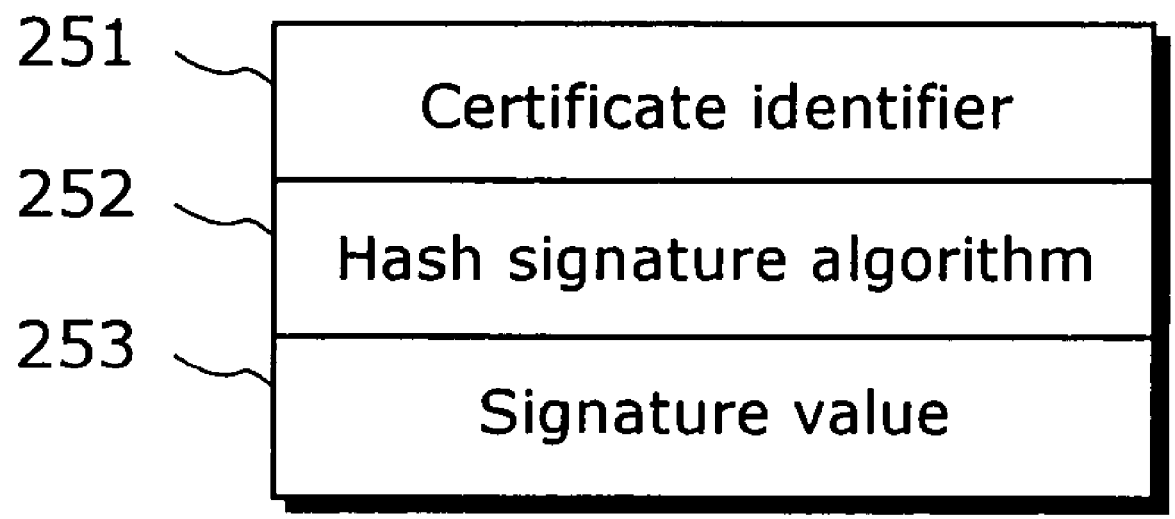
FIG. 25 is a diagram showing a structure of a signature file according to the present invention.

The file 2120 is a signature file. FIG. 25 is a schematic diagram showing the "ocap. signaturefile. 1" file 2120. 251 indicates a certificate identifier for identifying which X. 509 certificate is related, 252 indicates a hash signature algorithm, and 253 indicates a signature value that has been calculated from the "ocap. hashfile" 2116 by use of the hash signature algorithm indicated in 252.

Once a Java program is stored into the secondary storage unit 510, it is possible to activate such Java program without needing to wait for download as long as the AM 1205b has received the XAIT shown in FIG. 20, even in the case where the Java program was deleted from the primary storage unit 511 due to causes such as channel change and the power-off of the terminal apparatus 500. In other words, in FIG. 20, the control information 2002 of the program "/a/PPV1Xlet" is "autostart". Thus, in 2011 in FIG. 21, when a search is made for the storage position 2101 of the file system that corresponds to the "/a/PPV1Xlet" and then the file 2114 is passed to the JavaVM 1203, the Java program "PPV1Xlet" stored in such file system is activated.

Next, a description is given of the security manager 1205f that is a major functionality of the present invention.

The security manager 1205f receives, from the service manager 1204, a pre-storage notification indicating that "/a/PPV1Xlet" and "/b/PPVXlet2" indicated in 2004 in FIG. 20 are about to be stored. Upon receipt of such notification, the security manager 1205f checks the value of the Java program identifier 2001 to judge whether it is an unsigned program or a signed program. Here, since the Java program is a signed program, the security manager 1205*f* performs authentication of the file system lower than the "/" directory. To verify the file system, authentication is performed by use of the ocap. hashfiles (2116~2118), the ocap. certificate. 1 (2119), and the ocap. signaturefile. 1 (2120) illustrated in FIG. 21.

Figure 26:
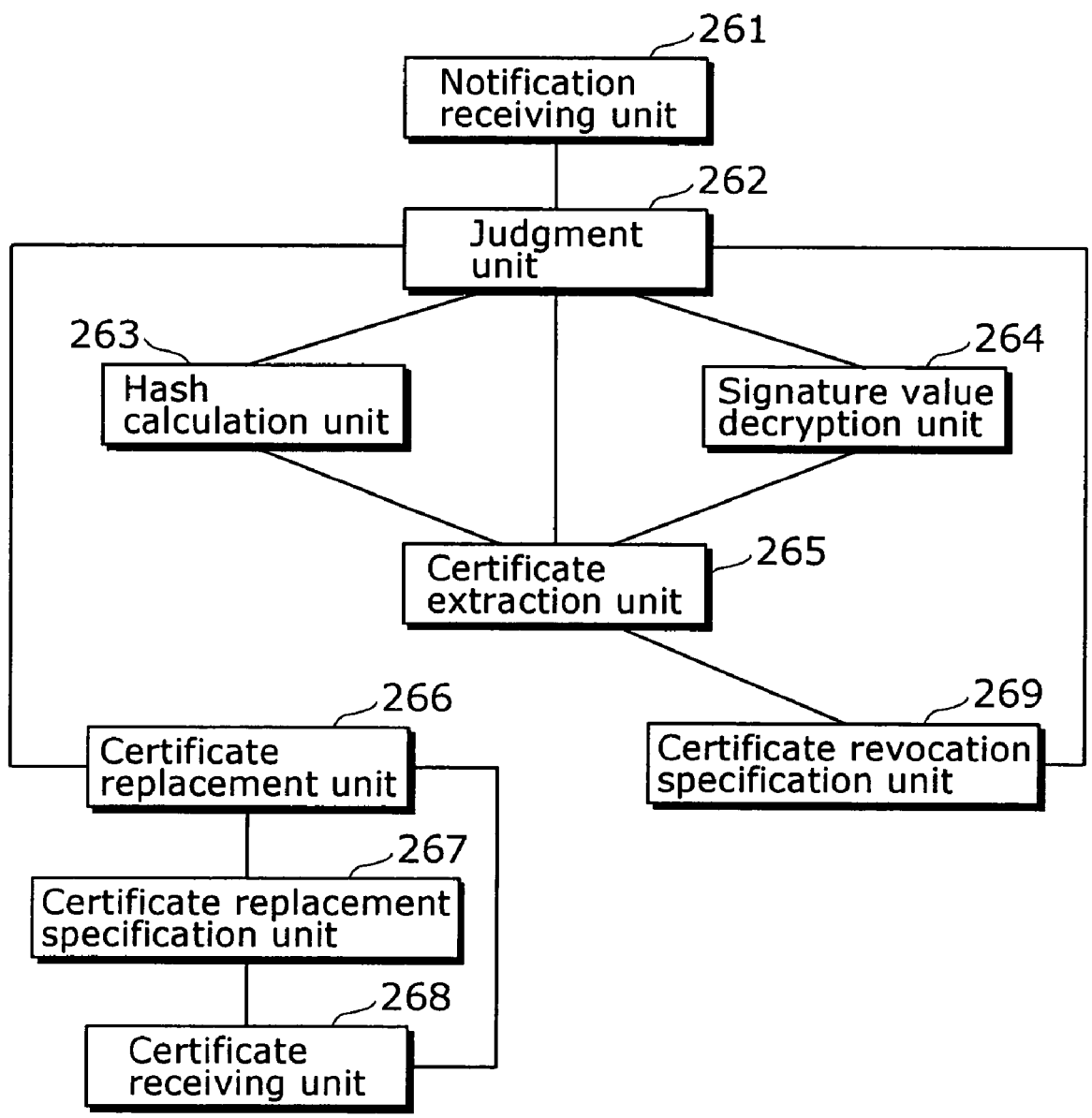
FIG. 26 is a diagram showing constituent elements of a security module according to the present invention.

FIG. 26 shows the constituent elements of the security manager 1205*f* for performing authentication of a file system.

A notification receiving unit 261 is intended for receiving a pre-storage notification immediately before the AM 1205*b* is about to store a file system as well as for notifying such fact to a judgment unit 262.

The judgment unit 262 judges an authentication result. It requests a hash calculation unit 263 to do hash calculations for the file system to receive hash values. The judgment unit 262 extracts, from among the hash values 2213, 2223, and 2233 that exist in the "ocap. hashfile" file, a value to be compared and checks whether or not it matches the received hash values. If they do not match, the judgment unit 262 judges that there has been tampering, and the authentication ends in failure.

Furthermore, the judgment unit 262 extracts each of the X. 509 certificates using a certificate extraction unit 265, and judges if the current time is not before this update date and time 2413 of each of the X. 509 certificates and not after the next update date and time 2414 of each of the X. 509 certificates (Namely, the current time is in between this update date and time 2413 and the next update date and time 2414 of each of the X. 509 certificates). The current date and time is obtained from the library 1201*b* of the OS 1201. If the validity period does not satisfy "this update date and time<current date and time<next update date and time", the judgment unit 262 judges that the authentication is a failure.

Moreover, in order to authenticate the certificate chain, the judgment unit 262 requests the hash calculation unit 263 to do a hash calculation for the attribute area 241 of each of the X. 509 certificates. Then, it requests a signature value decryption unit 264 to do a calculation for decrypting the signature value 242 included in each of the X. 509 certificates, and compares the resulting decrypted value with the hash values obtained by the hash value calculation unit 263 so as to check the status of the certificate chain. If they do not match, it means that the certificates are not in a chain relationship, and thus the authentication is judged to be a failure. Meanwhile, when such values match and it has been verified that the certificates are in a chain relationship, it is checked whether the root certificate in the certificate chain is included in the secondary storage unit 510 of the terminal apparatus 500. If not included, the judgment unit 262 judges that the authentication is a failure, regarding that it is impossible to perform a comparison.

The judgment unit 262 judges that authentication is successful when all of the following are satisfied: (1) there has been no tampering; (2) there is period validity; (3) certificates are in a chain relationship; and (4) root certificates match.

When requested by the judgment unit 262 to calculate a hash value of each of the files, the hash calculation unit 263 extracts each of the files from the library 1201*b* of the OS 1201 to perform hash calculations for them, and passes the resulting values to the judgment unit 262. Furthermore, the hash calculation unit 263 obtains each of the X. 509 certificates in the certificate chain 231 from the certificate extraction unit 265, and performs hash calculations for the attribute area 241 of each of them.

The signature value decryption unit 264 is requested by the judgment unit 262 to perform a calculation for decrypting the signature value of either each X. 509 certificate or "ocap. signaturefile. x". When performing a calculation to decrypt the signature of each X. 509 certificate, the signature value decryption unit 264 obtains each of the X. 509 certificates in the certificate chain 231 from the certificate extraction unit 265, and then performs a calculation for decrypting the signature of each of them, and returns the resultant to the judgment unit 262.

The certificate extraction unit 265 is requested to extract each of the X. 509 certificates in the certificate chain 231 by the judgment unit 262, the hash calculation unit 263, and the signature value decryption unit 264, and extracts and returns the X. 509 certificates.

Figure 27:
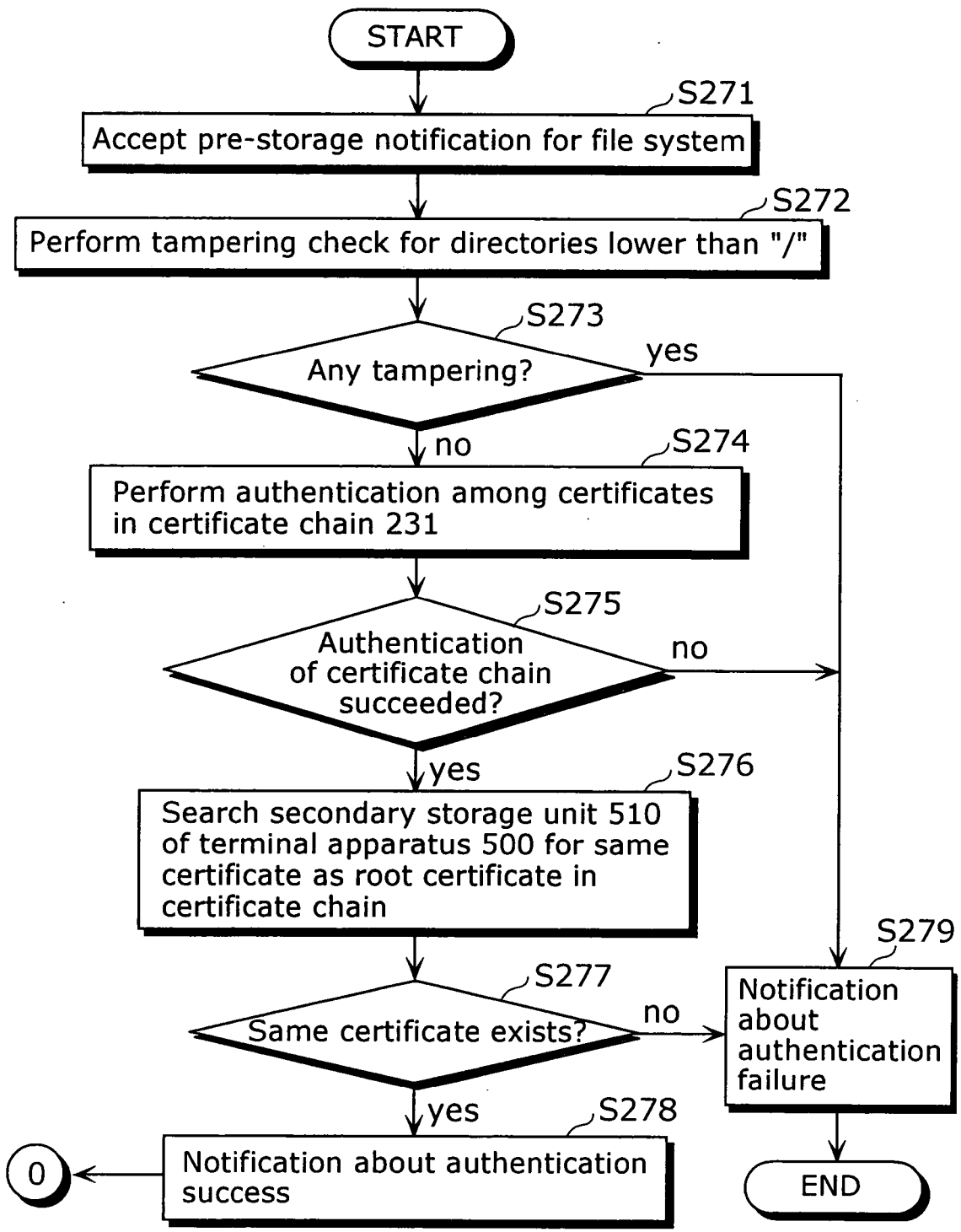
FIG. 27 is a flowchart showing an operation to be performed when a file system is authenticated according to the present invention.

FIG. 27 is a flowchart that summarizes an operation performed by the security manager 1205*f* when performing authentication of a file system. Based on this flowchart, an explanation is given of the operation to be performed in the case where the files system has the configuration shown in FIG. 21. Upon receipt of a pre-storage notification for the file system from the AM 1205*b* (Step S271), the security manager 1205*f* conducts a tampering check for the file system lower than the top-level "/" directory of the file system (Step S272). In the tampering check, it is verified, by comparing hash values, that there is no corruption or changes in files existing in each directory of the file system.

Figure 29:
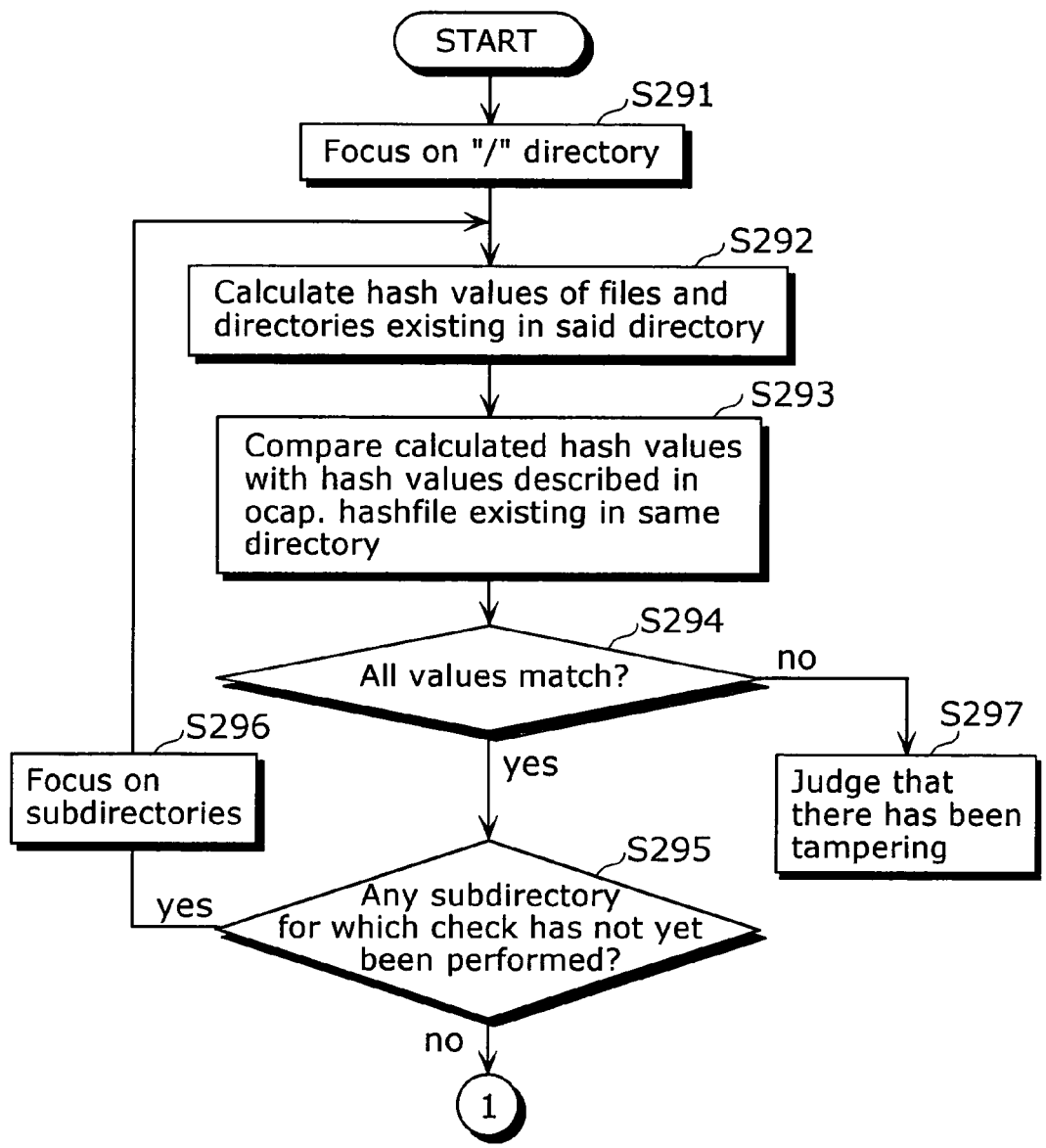
FIG. 29 is a flowchart showing an operation to be performed when a tampering check is performed for a file system according to the present invention.
Figure 30:
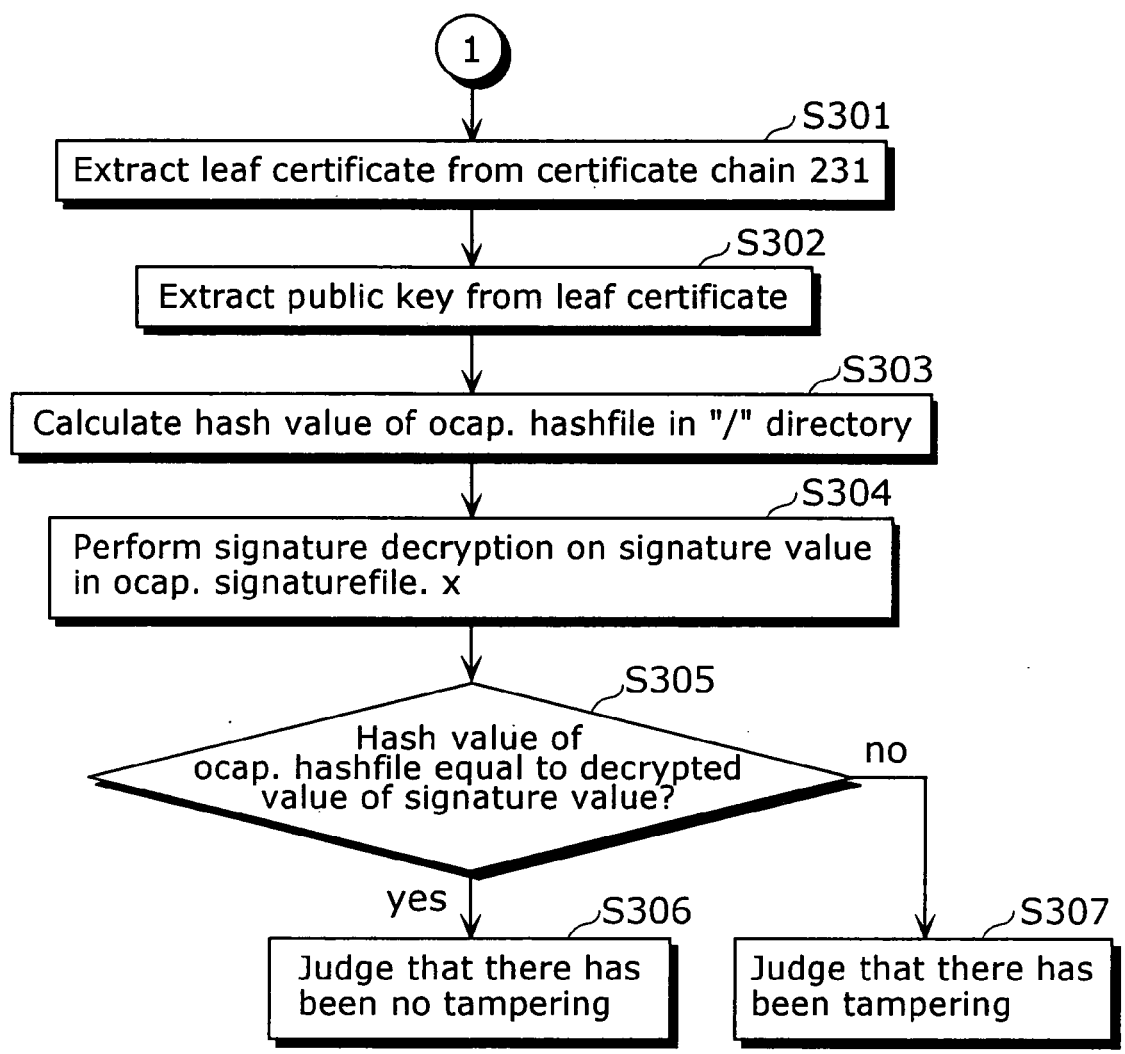
FIG. 30 is a flowchart showing an operation to be performed when a tampering check is performed by use of a signature file according to the present invention.

FIG. 29 and FIG. 30 are detailed flowcharts of Step S272. First, as shown in Step S291, hash values are calculated for the respective files "ocap. certificate. 1" and "ocap. signaturefile. 1" and the respective directories "a" and "b" that exist in the "/" directory. Note that the hash values of the directories "a" and "b" are calculated from the "/a/ocap. hashfile" file 222 and the "/b/ocap. hashfile" file 223, respectively. In Step S293, the hash values calculated in Step S292 are compared with each of the hash values described in 2213 in "/ocap. hashfile". In Step S294, if any of the calculated hash values differs from the hash values in 2213, it is judged that there has been tampering (Step S297). Meanwhile, when all of the calculated hash values match the hash values in 2213, a transition is made to Step S295. In Step S295, it is checked whether there exists any subdirectory for which a tampering check has not been completed. At the current stage, the directories "a" and "b" exist as the subdirectories of the "/" directory, for which tampering checks have not yet been performed. Therefore, tampering checks need to be performed for these directories "a" and "b". First, a focus is put on the "a" directory in Step S296, where a process equivalent to the one performed for the "/" directory is performed. After the tampering check for the "a" directory is completed, a tampering check is performed for the "b" directory. When tampering checks for the directories "a" and "b" have been completed, a focus is then put on the "/" directory, and the process for Step S301 in FIG. 30 is performed. In Step S301, the leaf certificate 2313 is extracted from the "/ocap. certificate. 1" file 2119, which is the certificate chain 231. Then, in Step S302, the public key 2417 is taken out from the extracted leaf certificate 2313. Subsequently, in Step S303, a hash value for the "/ocap. hashfile" file 221 is calculated. Meanwhile, in Step S304, decryption is performed on the signature value 242 in the "/ocap. signaturefile. 1" file 2120, using the public key 2417 that exists in the leaf certificate 2313 in "/ocap. certificatefile. 1" file 2119. In Step S305, it is checked whether the hash value calculated in Step S303 is equal to the value obtained in Step S304 by decrypting the signature value. If these calculated values match, it is possible to judge that the file system lower than the "/" directory has not been tampered with (Step S306). Meanwhile, if the calculated values do not match, it is possible to judge that the file system has been tampered with (Step S307). Note that a description has been given for an example in which tampering checks are performed starting with the top-level "/" directory toward the subdirectories in descending order, but the present invention is not limited to this. Therefore, processes may be performed starting with the lowest-level directory toward the top-level directory in ascending order. Through the above processes, the result of Step S272 in FIG. 27 is obtained.

In Step S273, when the result in Step S272 is "there has been tampering", it is judged that the authentication has failed and a notification is made about such fact (Step S279), after which the process is terminated. When the result of Step S272 is "no tampering", the process for Step S274 is executed.

Figure 31:
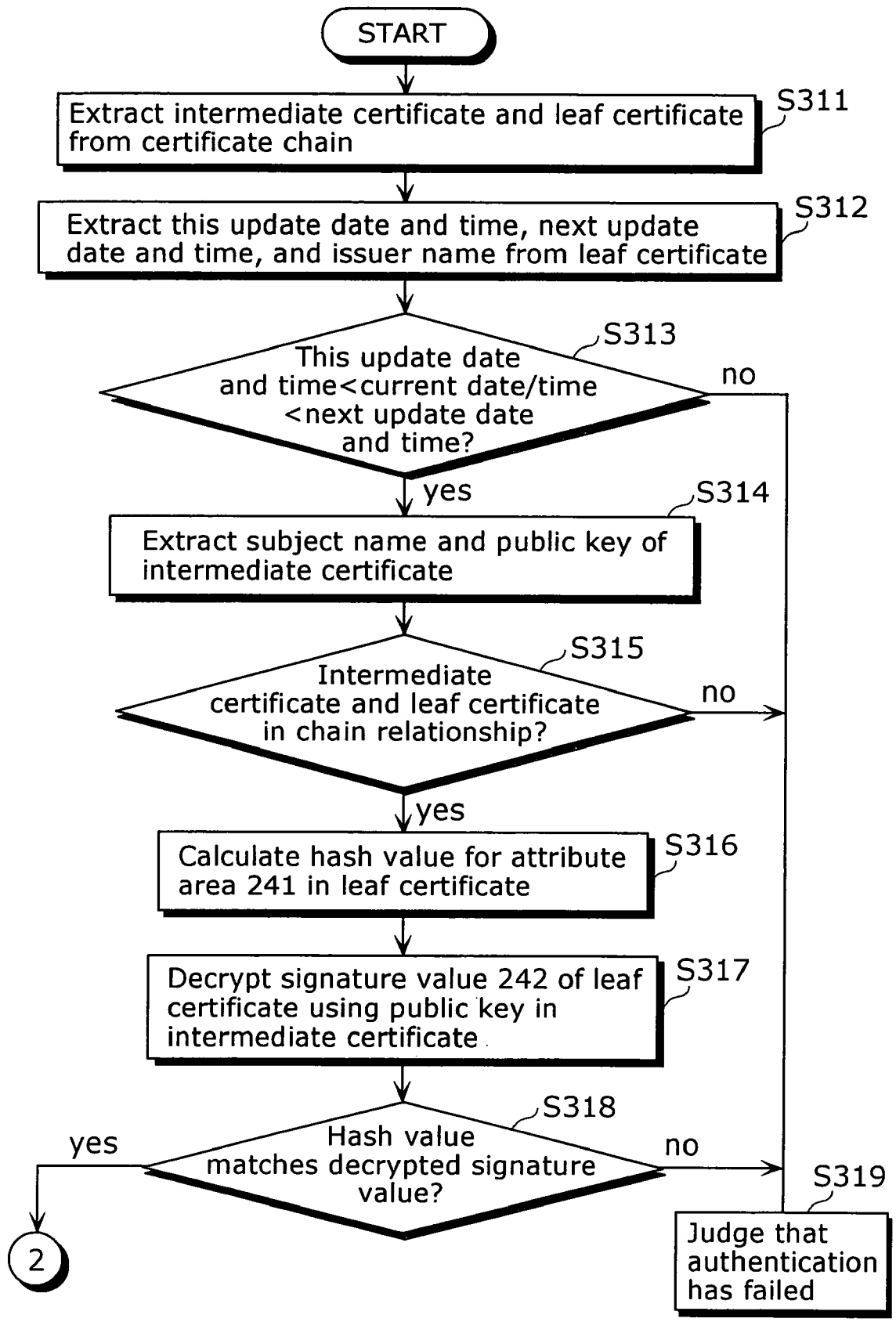
FIG. 31 is a flowchart showing an operation to be performed when a chain relationship between a leaf certificate and an intermediate certificate is checked according to the present invention.
Figure 32:
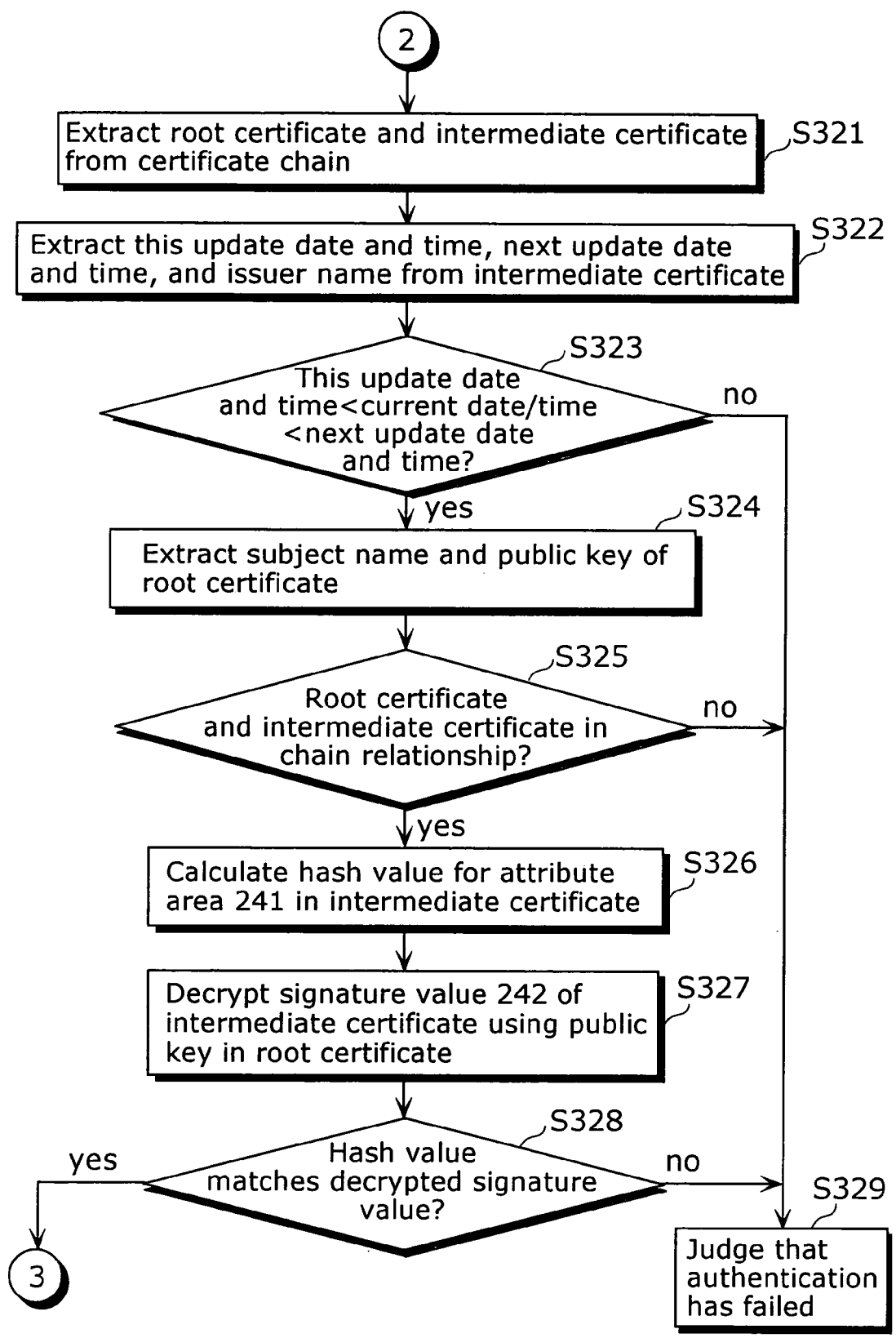
FIG. 32 is a flowchart showing an operation to be performed when a chain relationship between an intermediate certificate and a root certificate is checked according to the present invention.
Figure 33:
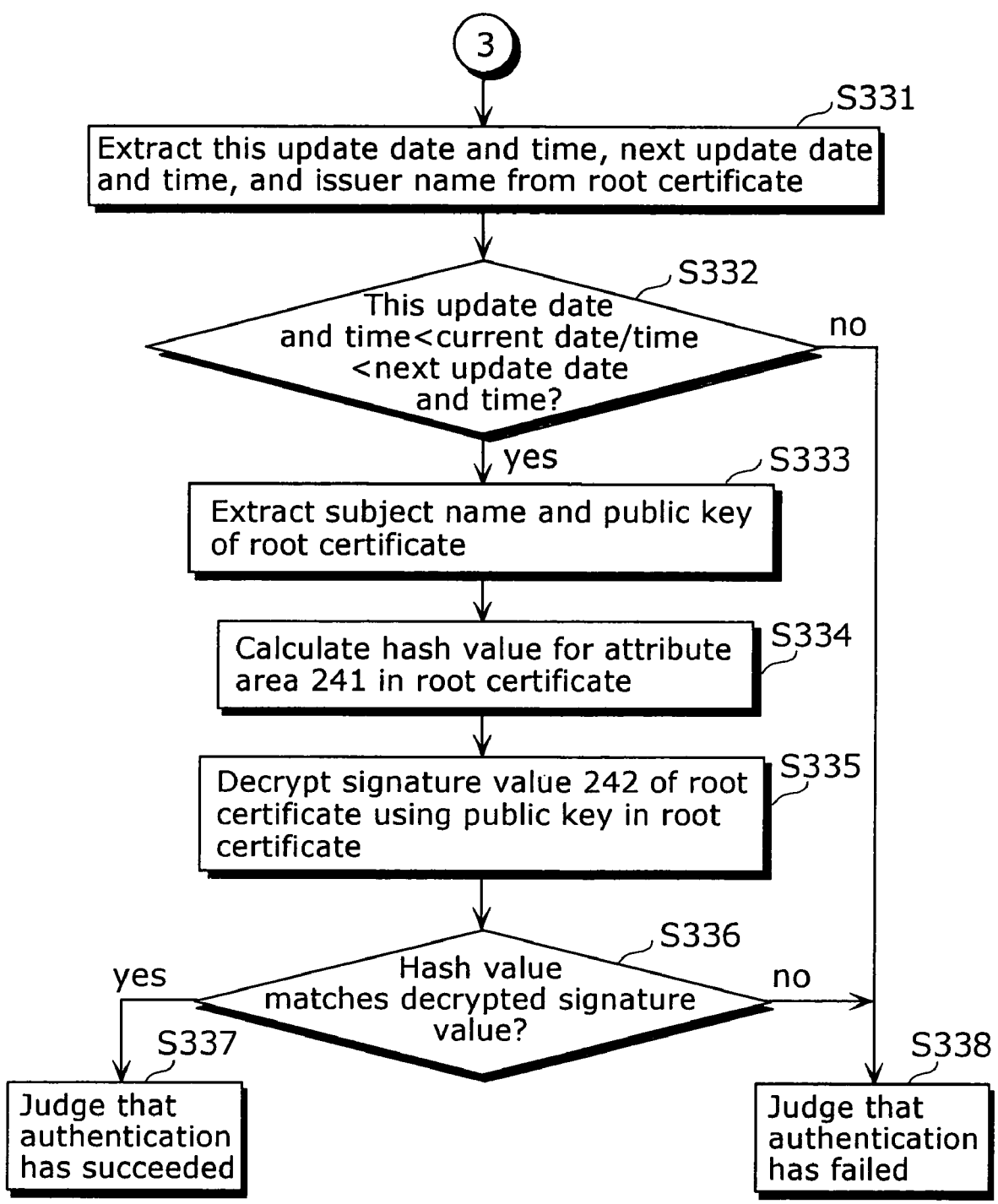
FIG. 33 is a flowchart showing an operation to be performed when a signature in a root certificate is checked according to the present invention.

Next, referring to FIG. 31 to FIG. 33, a detailed description is given of certificate chain authentication (Step S274). Assuming that a check is first performed for the intermediate certificate 2312 and the leaf certificate 2313, a flowchart for it is shown in FIG. 31. First, the intermediate certificate 2312 and the leaf certificate 2313 are extracted from the certificate chain 231 (Step S311). From such extracted leaf certificate 2313, this update date and time 2413, next update date and time 2414, and the issuer name 2415 are extracted (Step S312). Of them, it is judged whether the current date and time is in between said this update date and time 2413 and next update date and time 2414 during which the certificate can remain valid (Step S313). If it is beyond the period during which the certificate can remain valid, the authentication of the certificate chain ends in failure (Step S319). Meanwhile, when it is judged that it is within the valid period of the certificate, the subject name 2416 and the public key 2417 in the intermediate certificate 2312 are extracted (Step S314), and a comparison is made between the subject name 2416 of the intermediate certificate 2312 and the issuer name 2415 of the leaf certificate 2313 to judge if the intermediate certificate 2312 and the leaf certificate 2313 are in a chain relationship or not (Step S315). If these certificates are not in a chain relationship, the authentication of the certificate chain is a failure. Meanwhile, when there is a chain relationship between them, a hash value for the attribute area 241 of the leaf certificate 2313 is calculated (Step S316). Furthermore, the signature value 242 in the leaf certificate 2313 is decrypted with the public key 2417 of the intermediate certificate 2312 (Step S317). When Step S316 and Step S317 are completed, it is checked whether the hash value and the decrypted signature value obtained in the respective steps match or not (Step S318). If they do not match, the authentication of the certificate chain ends in failure (Step S319).

Next, a check is performed between the root certificate 2311 and the intermediate certificate 2312. FIG. 32 is a flowchart showing this process. The root certificate 2311 and the intermediate certificate 2312 are extracted form the certificate chain 231 (Step S321), and a process that is equivalent to the check performed for the intermediate certificate 2312 and the leaf certificate 2313 is performed for the root certificate 2311 and the intermediate certificate 2312 (Step S322~Step S328).

When it is judged in Step S328 that the values match, a check is performed solely for the root certificate 2311. FIG. 33 is a flowchart showing a check to be performed solely for the root certificate 2311. From the root certificate 2311 extracted in Step S321, this update date and time 2413, next update date and time 2414, and the issuer name 2415 are extracted (Step S331). Of them, it is judged whether the current date and time is in between said this update date and time 2413 and next update date and time 2414 during which the certificate can remain valid (Step S332). If it is beyond the period during which the certificate can remain valid, the authentication of the certificate chain ends in failure. Meanwhile, when it is judged that it is within the validity period of the certificate, a hash value for the attribute area 241 of the root certificate 2311 is calculated (Step S334). Furthermore, the signature value 242 in the root certificate 2311 is decrypted with the public key 2417 of the root certificate 2311 (Step S335). When Step S334 and Step S335 are completed, it is checked whether the hash value and the decrypted signature value obtained in the respective steps match or not (Step S336). If they do match, the authentication of the certificate chain is successful (S337), whereas if they do not match, the authentication of the certificate chain ends in failure (Step S338). At this point, the process of Step S274 ends.

The process is performed differently in Step S275 depending on the result of S274. When the result of Step 274 is "authentication of certificate chain failed", it is judged that the authentication has failed and a notification is made about it (Step S279), and then the authentication for the file system is terminated. Meanwhile, in the case of "authentication of certificate chain succeeded", the process of Step S276 is performed.

Figure 28:
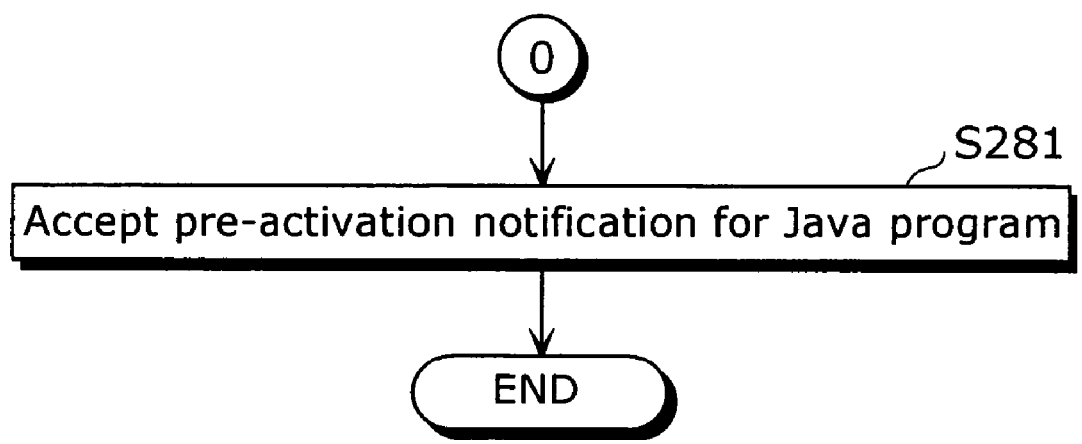
FIG. 28 is a flowchart in the case where no authentication is performed when a program pre-activation notification is received according to the present invention.

Next, the secondary storage unit 510 of the terminal apparatus 500 is searched for a certificate that is the same as the root certificate 2311 of the "/ocap. certificate. 1" file 2119 (Step S276). When the same certificate is not present in the secondary storage unit 510, it is judged in Step S277 that the authentication of the certificate chain 231 is a failure, and a notification is made about this authentication failure (Step S279), after which the process is terminated. Meanwhile, when the root certificate 2311 is included, it is judged that the authentication of the file system is successful, and a notification is made to the AM 1205b about this authentication success (Step S278). Referring to FIG. 28, even if a pre-activation notification for a Java program is received after that (Step S281), the process is terminated with nothing performed.

In the first embodiment, when a stored Java program is to be activated after a certain period of time, there is no need to perform authentication at that point since the file system was already authenticated immediately before it was stored.

Here, a description is given of the case where "application description file" shown in FIG. 34 exists in the file system and only the files described therein are to be stored. According to the OCAP specification, for example, "application description file" is described in the XML (extensible Markup Language) format. FIG. 34 shows one example of "application description file". In FIG. 34, there is no description of the "PPV2Xlet. class" 2115 shown in FIG. 21. In this case, therefore, the "PPV2Xlet. class" 2115 is not included as storage targets. In this case, no hash value is calculated in S292 for the "PPV2Xlet. class" 2115 and thus no comparison is made in S293 with the hash value in 2233 described in the "ocap. hashfile" file 2118. In Step S294, a transition may be made to the process of S295 by stipulating that files not included as storage targets are out of application.

SECOND EMBODIMENT

When a Java program (PPV1Xlet. class 2114 or PPV2Xlet. class 2115) included in the file system is to be activated a certain period of time after such file system is stored, there is a possibility that the validity of one of the X. 509 certificates included in the "/ocap. certificate. 1" file 2119 is expired (i.e. activation date and time of the Java program>next update date and time 2414). The first embodiment, however, allows the Java program to be activated even if an already expired X. 509 certificate is included in the certificate chain 231.

Thus, the present embodiment is achieved by adding, to the first embodiment, the function of verifying, at the time of activating a Java program, that the validity of each of the certificates 2311, 2312, and 2313 included in the certificate chain 231 is not expired. FIG. 26 shows the constituent elements in the present embodiment. Constituent elements 261-265 necessary for the present embodiment are already described in the first embodiment, and therefore descriptions thereof are not given here.

Figure 35:
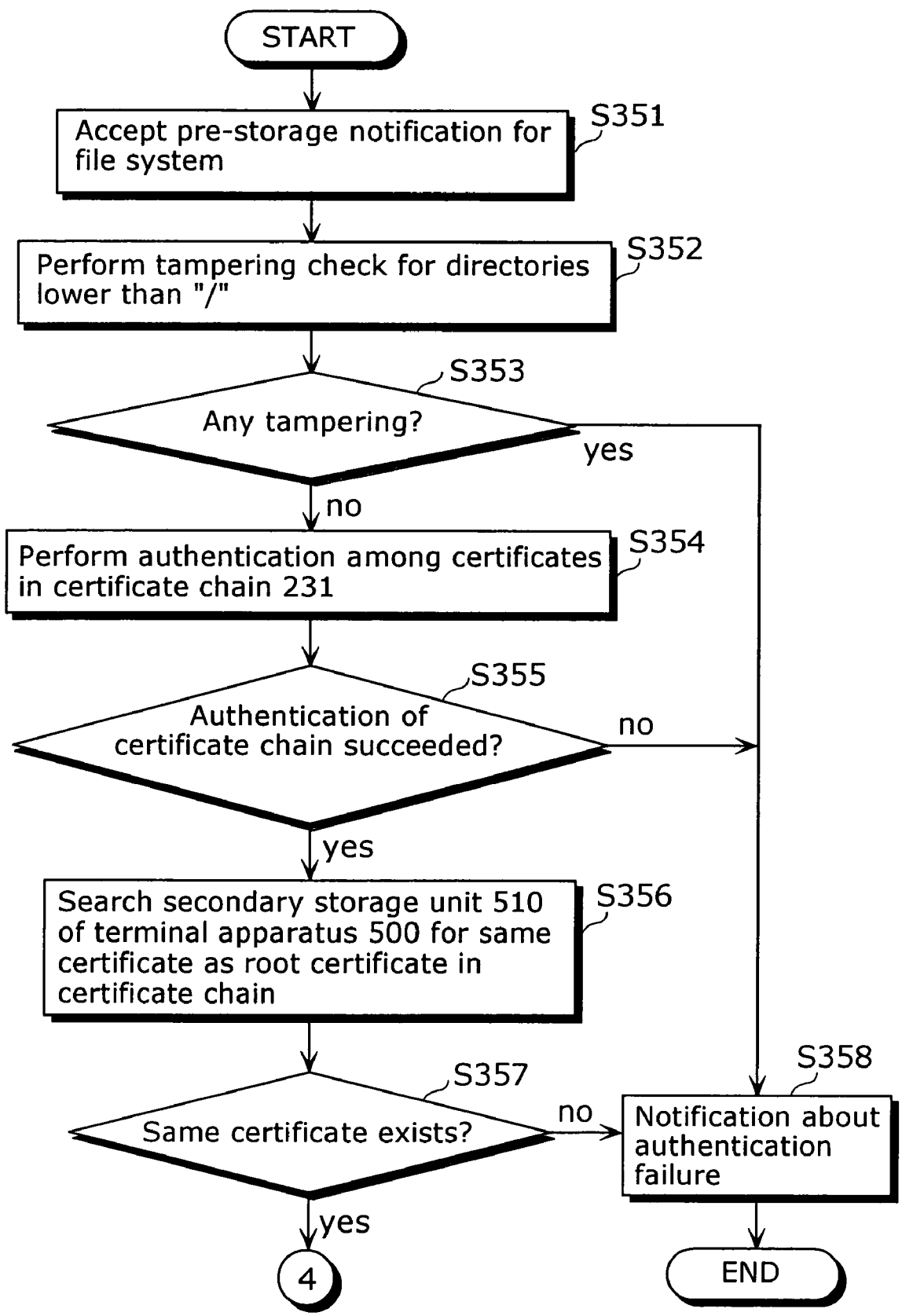
FIG. 35 is a flowchart showing an operation to be performed when authentication of a file system is performed according to the present invention.
Figure 36:
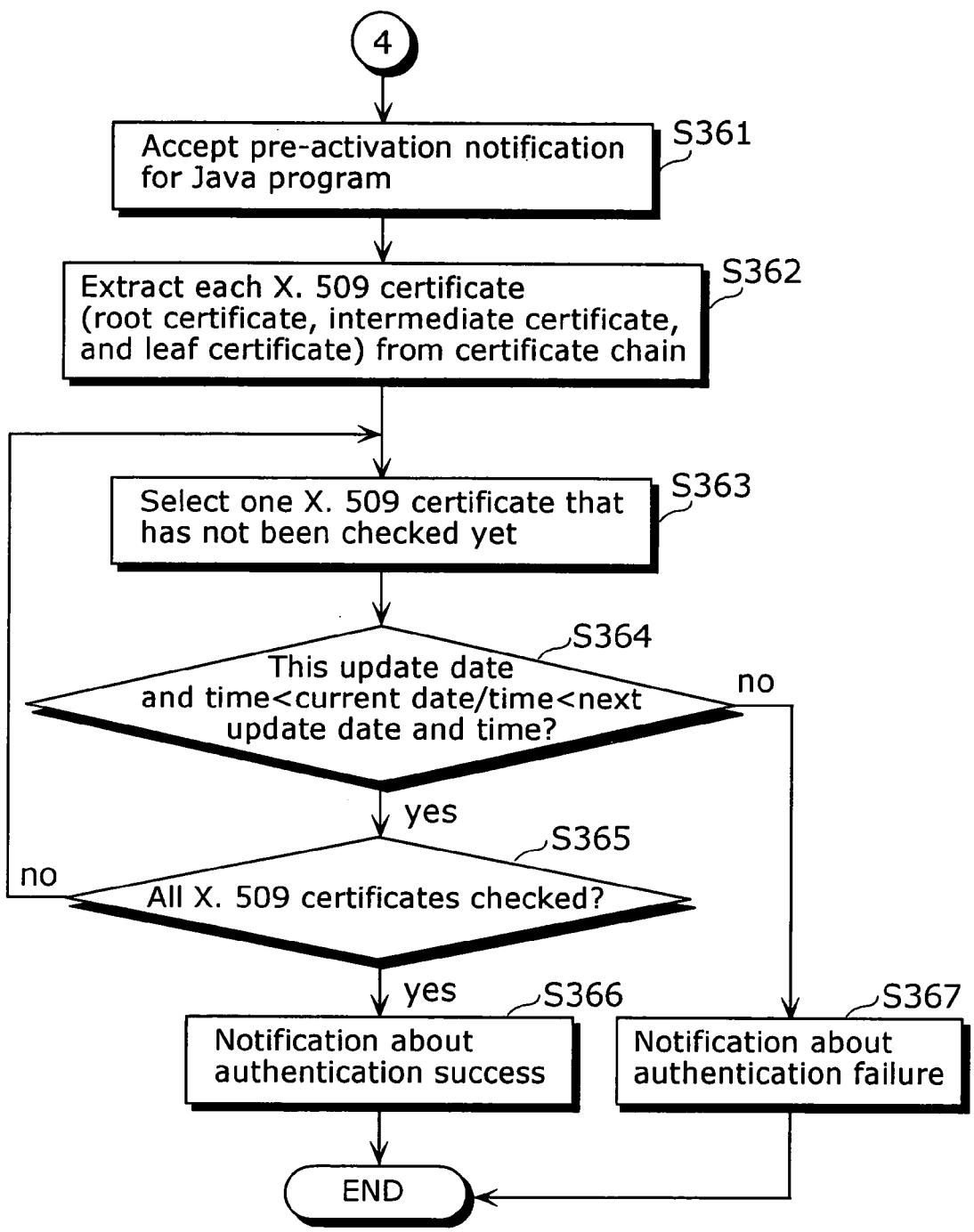
FIG. 36 is a flowchart showing an operation to be performed at the time of checking the validity of X. 509 certificates when a program pre-activation notification is received according to the present invention.

As flowcharts, the flowchart of FIG. 27 is replaced by the flowchart of FIG. 35 and the flowchart of FIG. 36 is added.

Referring to FIG. 35, the processes to be performed immediately before the file system is stored (Step S351 to Step S357) are the same as the processes explained in the first embodiment (Step S271 to Step S277), and therefore descriptions thereof are omitted. If the authentication is not a failure, the process goes onto the flowchart shown in FIG. 36. When a notification that the PPV1Xlet. class 2114, which is a Java program, is to be activated after a certain period of time (Step S361), each of the X. 509 certificates, i.e., the root certificate 2311, the intermediate certificate 2312, and the leaf certificate 2313 are extracted from the "ocap. certificate. 1" file 2119 (Step S362). Then, the extracted X. 509 certificates are selected one by one in order starting with the leaf certificate to the root certificate (Step S363), and it is checked whether the current date and time is in between this update date and time 2413 and the next update date and time 2414 of each of the selected X. 509 certificates (Step S364). If the current date and time is not in between this update date and time 2413 and the next update date and time 2414, it is judged that the authentication is a failure and a notification is made about such fact (Step S367). In the other case, it is checked whether checks have been performed for all the X. 509 certificates or not (Step S365). If checks have not been completed for all the X. 509 certificates, the process is returned to S363, and the subsequent processes are repeated. Meanwhile, when all the X. 509 certificates have already been checked in Step S365, it is judged that the authentication is successful, and a notification is made about this authentication success (Step S366), after which the process is terminated. By adding the processes shown in the flowchart of FIG. 36, it becomes possible to notify the AM 1205b of authentication failure so that a Java program whose validity period has expired will not be activated. When notified by the security manager 1205f of authentication failure, the AM 1205b aborts the activation without passing such Java program to the JavaVM 1203.

THIRD EMBODIMENT

As described in the first embodiment, the secondary storage unit 510 includes an X. 509 certificate being the root certificate, which is compared with the root certificate 2311 in the certificate chain 231. The root certificate stored in the secondary storage unit 510 is replaced by a new X. 509 certificate (hereinafter referred to as certificate replacement) in preparation for the case where the credibility of the certificate is degraded due to hacking and others. The new X. 509 certificate is transmitted from the head end 101 to the terminal apparatus 500 to be delivered to the security manager 1205f via the download module 106.

Figure 38A:
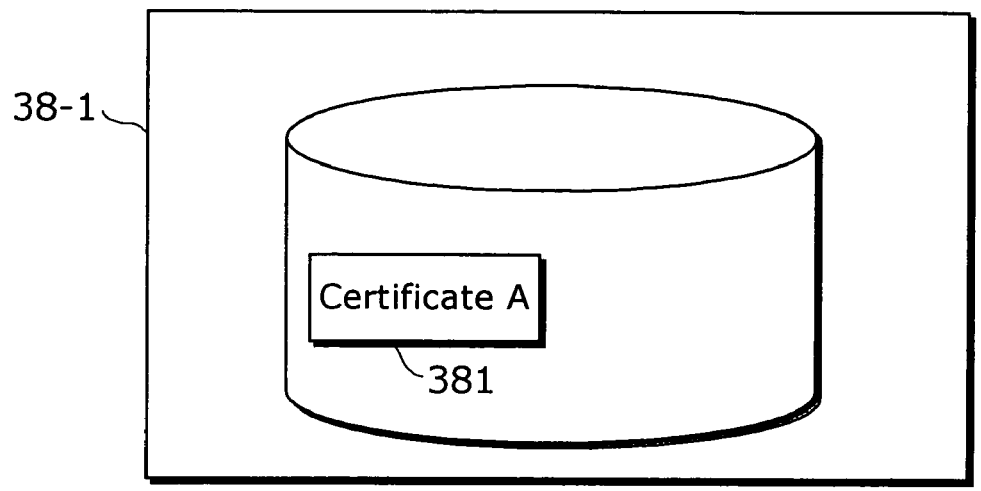
FIGS. 38A, 38B, and 38C are diagrams, each showing a certificate(s) owned by the terminal apparatus being replaced according to the present invention.
Figure 38B:
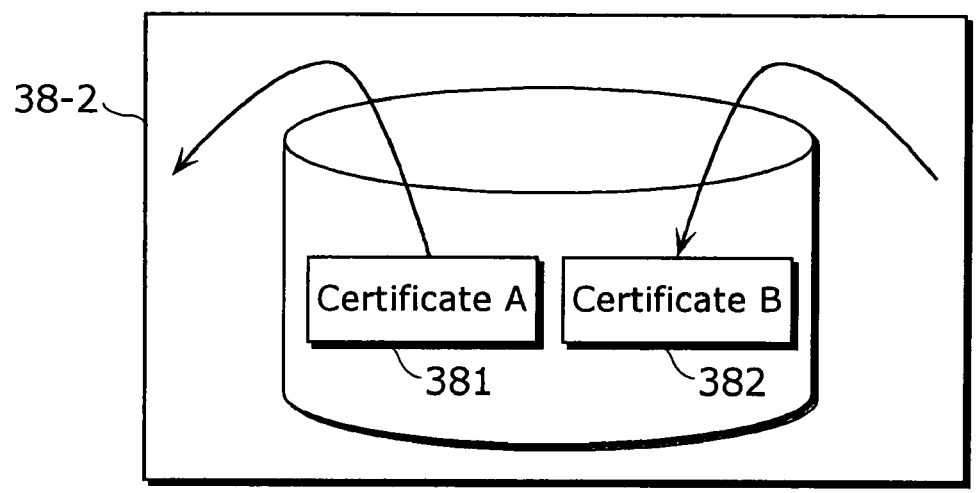
Figure 38C:
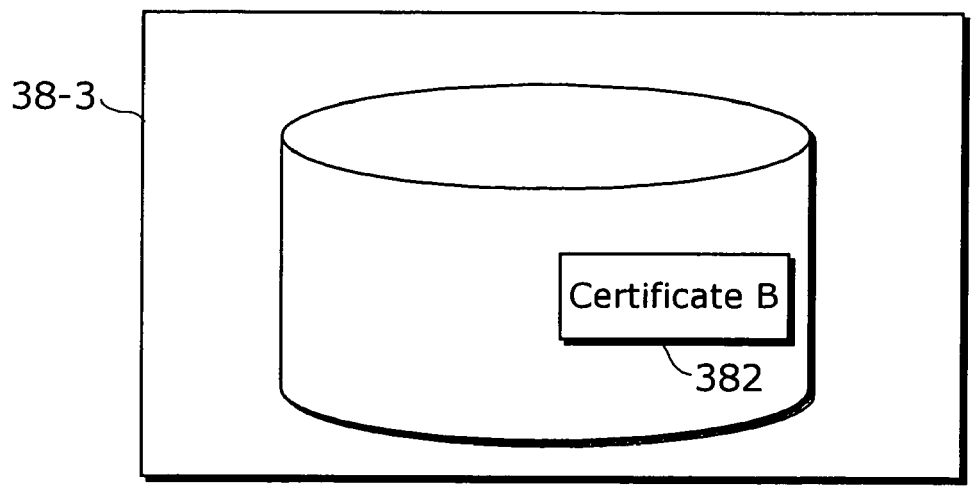

FIGS. 38A, 38B, and 38C are diagrams, each showing a root certificate in the secondary storage unit 510 being replaced (certificate replacement) by the security manager 1205f. In this case, a certificate A381 is an old certificate to be replaced, whereas a certificate B382 is a new certificate. 38-1 in FIG. 38A shows the certificate stored in the secondary storage unit 510 before certificate replacement is performed, 38-2 in FIG. 38B shows the certificate in the middle of being replaced, and 38-3 in FIG. 38C shows the certificate stored in the secondary storage unit 510 after certificate placement is performed.

In the first embodiment and the second embodiment, even when certificate replacement is performed after a Java program is stored, no consideration is made for a new certificate at activation time of the Java program. Consider, for example, that the root certificate 2311 in the certificate chain 231 matches the certificate A3811 when the security manager 1205f is authenticating a Java program in response to its pre-storage notification and that the security manager 1205f receives a pre-activation notification for the Java program after the certificate A381 is replaced by the certificate B382. At this point of time, the secondary storage unit 510 does not include any certificates that match the root certificate 2311 in the certificate chain 231, meaning that such certificate is not credible. However, in the first embodiment and the second embodiment, since no comparison is made between root certificates immediately before the activation of a Java program (i.e. the root certificate 2311 in the certificate chain 231 is not compared with the certificate B382), a notification is not made to the AM 1205b about authentication failure. As a result, the AM 1205b causes the Java program to be activated.

Thus, the present embodiment is added with the function of performing a comparison of root certificates in consideration of certificate replacement at the time of Java program activation.

FIG. 26 shows the constituent elements in the present embodiment. The constituent elements 261~265 have already been described and therefore explanations thereof are omitted. A certificate replacement unit 266, a certificate replacement specification unit 267, and a certification receiving unit 268 are added.

When the certificate replacement specification unit 267 judges that a certificate that is older than the received certificate is stored in the secondary storage unit 510, the certificate replacement unit 266 replaces such old certificate with the new certificate. Meanwhile, when the certificate replacement specification unit 267 judges that no older certificate is stored, the certificate replacement unit 266 stores the new certificate into the secondary storage unit 510.

The certificate replacement specification unit 267 receives the certificate received by the certificate receiving unit 268. Then, it checks the certificate stored in the secondary storage unit 510 to see if there is any certificate whose issuer is the same and which is older than the received certificate, by use of the library 1201b of the OS 1201.

The certificate receiving unit 268 receives a new certificate when the download module 1206 receives such new certificate from the head end 101. Upon receipt of the certificate, the certificate receiving unit 268 passes it to the certificate replacement unit 266 and the certificate replacement specification unit 267.

Figure 39:
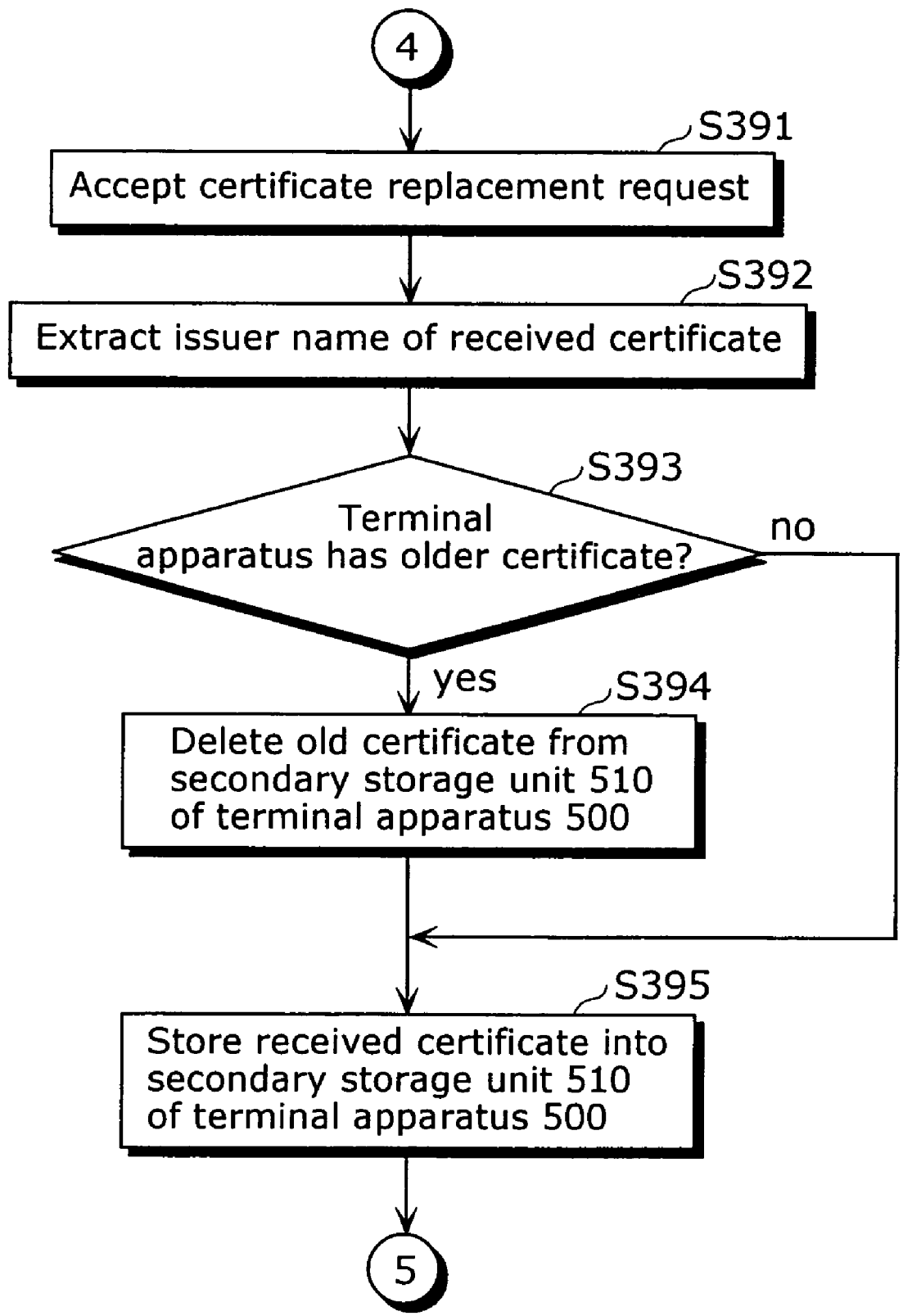
FIG. 39 is a flowchart showing an operation to be performed when certificate replacement is performed according to the present invention.
Figure 40:
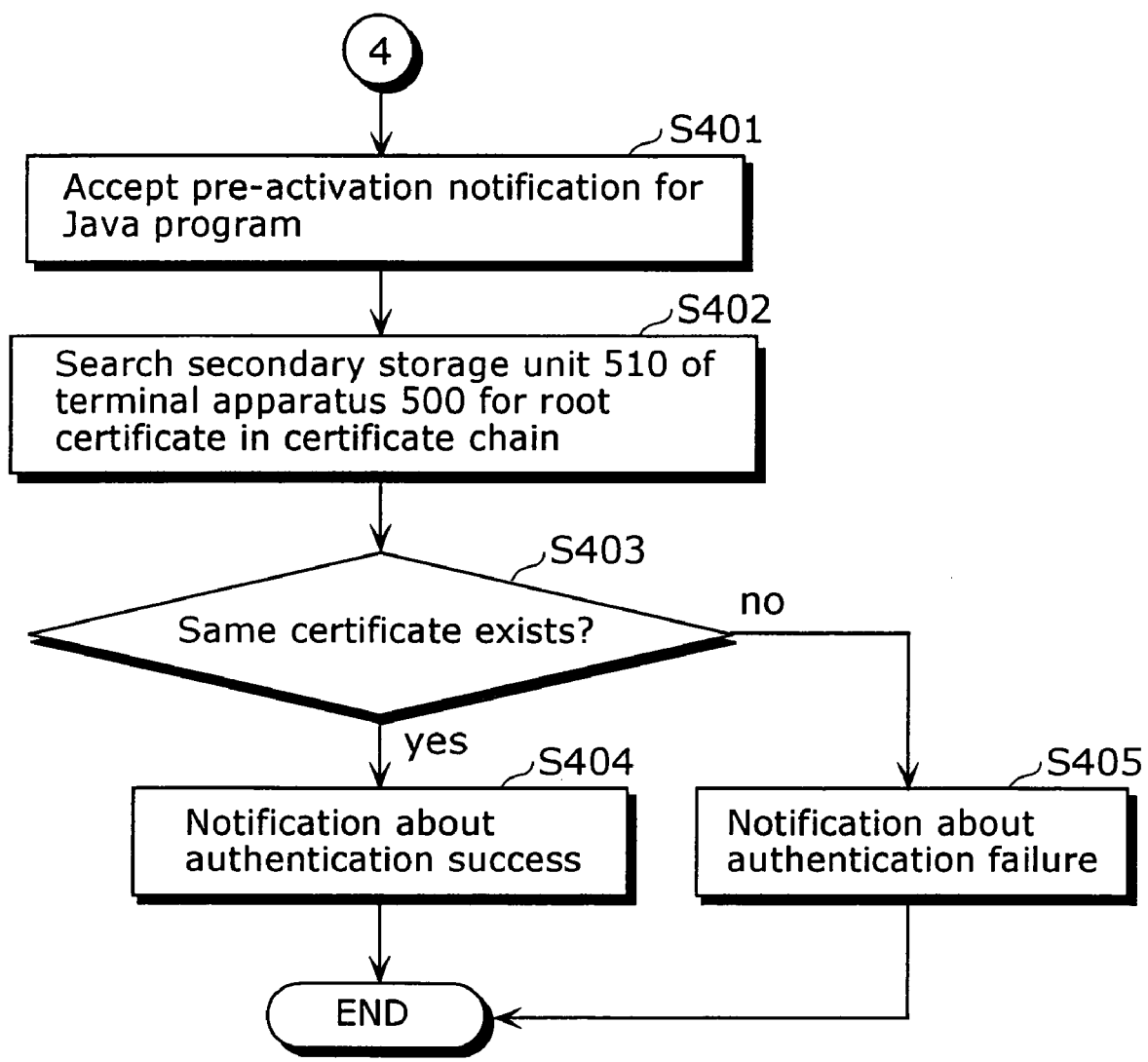
FIG. 40 is a flowchart showing an operation to be performed at the time of comparing root certificates when a program pre-activation notification is received according to the present invention.

In addition, FIG. 39 and FIG. 40 are added subsequently to the flowchart of FIG. 35.

FIG. 39 is a flowchart at the time of performing certificate replacement, while FIG. 40 is a flowchart at the time of activating the Java program after certificate replacement is performed. Referring to FIG. 39, when a request for certificate replacement is received (Step S391), the issuer name of such received certificate is extracted (Step S392). It is checked whether an old certificate that needs to be replaced is present in the secondary storage unit 510 of the terminal apparatus 500 (Step S393), and only when an old certificate is present, such certificate is deleted. Then, the received certificate is stored into the secondary storage unit 510 (Step S395). When an activation notification for the Java program is received after a certain period of time (Step S401), the secondary storage unit 510 is searched for the certificate that matches the root certificate 2311 in the certificate chain 231 (Step S402), and if there is any (Step S403), it is judged that the authentication is successful and a notification is made about such fact (Step S404). If there is no matching certificate (Step S403), it is judged that the authentication is a failure, and a notification is made about such fact (Step S405). Note that before it is judged in Step S404 that the authentication is successful, it is also possible to conclude that the authentication is successful after verifying that each of the X. 509 certificates in the certificate chain satisfies "this update date and time<current date and time<next update date and time".

Moreover, in addition to checking if root certificates match, it is also possible to judge that authentication is successful/unsuccessful after performing, before S402, the check shown in FIG. 31~FIG. 33 to see if the certificates in the certificate chain are in a chain relationship or not.

Furthermore, the above descriptions have been given for the case where a certificate that should be replaced is specified based on the issuer name, but the certificate may also be specified based on another attribute value such as the subject name.

FOURTH EMBODIMENT

When a Java program (PPV1Xlet. class 2114 or PPV2Xlet. class 2115) included in the file system is to be activated a certain period of time after such file system is stored, there is a case where a certificate is revoked due to reasons other than that the validity of any of the X. 509 certificates included in the "/ocap. certificate. 1" file 2119 is expired and that the root certificate was replaced. This configuration allows the Java program to be activated even when there exists a revoked certificate.

Figure 41:
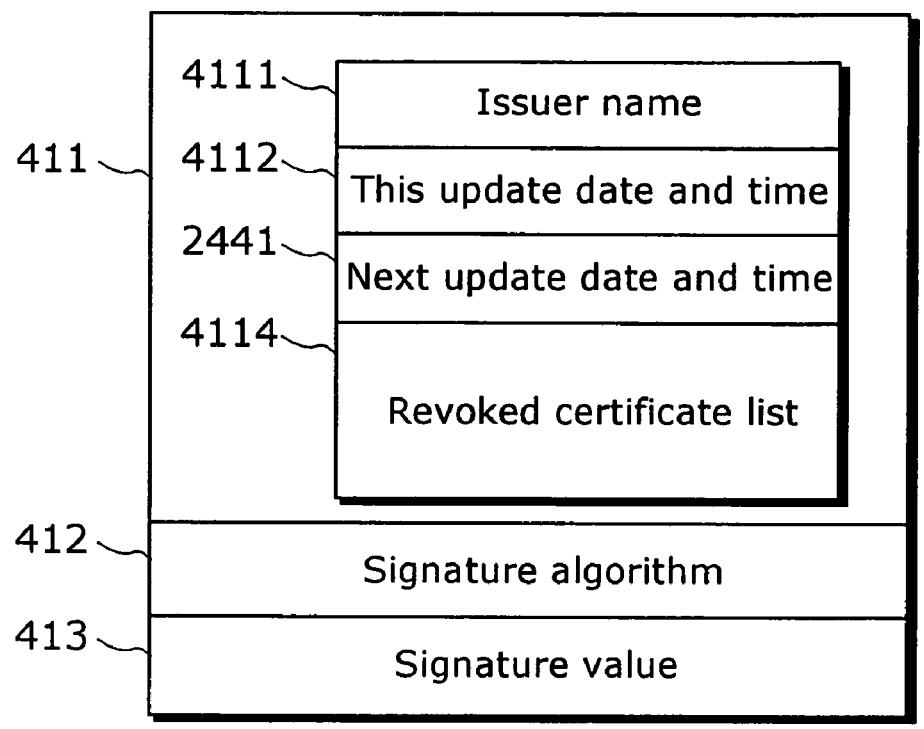
FIG. 41 is a diagram showing a structure of a CRL according to the present invention.
Figure 42:
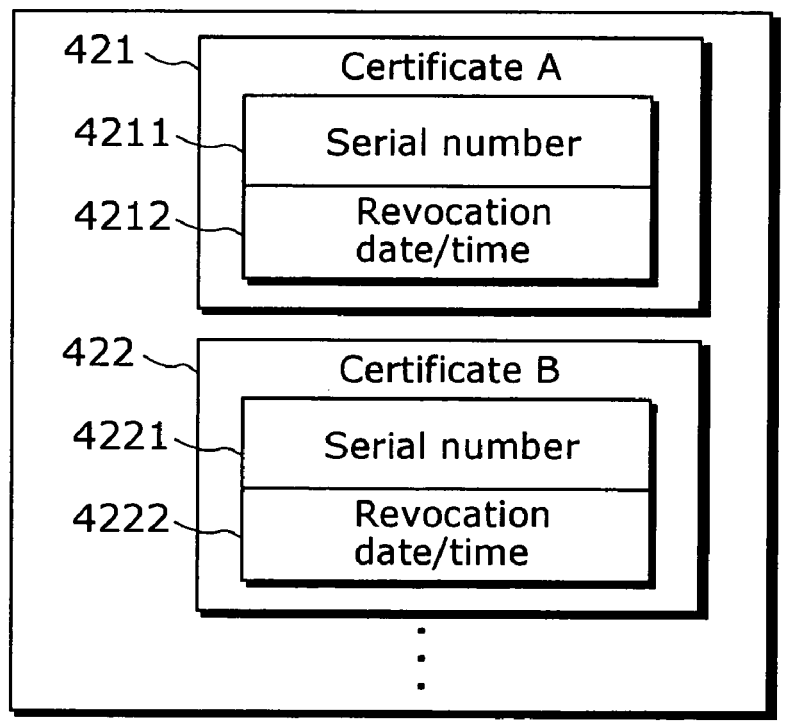
FIG. 42 is a schematic diagram showing a revoked certificate list in the CRL according to the present invention.

Here, CRL (Certificate Revocation List) is a widely known revoker of certificates. FIG. 41 is a diagram showing the structure of a CRL. Here, only attributes necessary for explaining the present invention are illustrated. For more details about CRL, refer to IETF RF C3280 "Internet X. 509 Public Key Infrastructure Certificate and CRL Profile". 411 indicates an attribute area of the CRL, 412 indicates the signature algorithm of a signature value 413, and 413 indicates the signature value of the CRL. Issuer name 4111 indicates the issuer of this CRL, this update date and time 4112 indicates the date and time when the CRL becomes valid, next update date and time 4113 indicates the date and time when the validity of the CRL expires, and revoked certificate list 4114 indicates information about revoked X. 509 certificates. FIG. 42 is a diagram showing the structure of the revoked certificate list 4114. Only attributes that are necessary for explaining the present invention are illustrated here, too. Information about a plurality of revoked X. 509 certificates is stored in the revoked certificate list 4114. In the case of FIG. 42, as information about a revoked "certificate A" 421, a serial number 4211 for uniquely identifying the certificate and date and time 4212 when the "certificate A" 421 became revoked are included. Other revoked certificates are also equivalent to 421.

Figure 43:
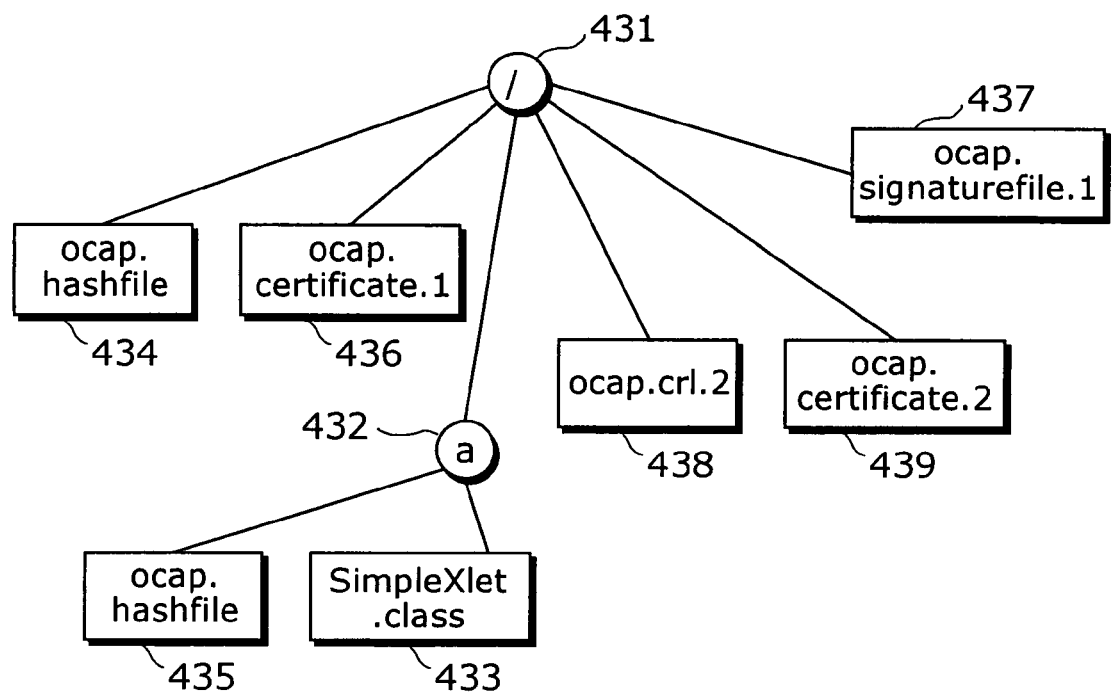
FIG. 43 is a diagram showing an example of a file system that includes a CRL according to the present invention.

FIG. 43 is an example configuration of a file system that includes a CRL. A "/" directory 431, an "a" directory 432, a "SimpleXlet. class" file 433, "ocap. hashfile" files 434~435, an "ocap. certificate. 1" file 436, an "ocap. signaturefile. 1" file 437, an "ocap. crl. 2" file 438, and an "ocap. certificate. 2" file 439 are internally stored. Authentication of a file system that includes no CRL is as described in the first embodiment. Thus, a focus is put in the present embodiment on the "ocap. crl. 2" file 438 that is structured in the CRL format and the "ocap. certificate. 2" file 439 that is the certificate chain of such file. Note that according to the OCAP specification, the certificate chain of "ocap. crl. x" is "ocap. certificate. x". In the case of FIG. 43, the certificate chain of the "ocap. crl. 2" is "ocap. certificate. 2".

FIG. 46 is a schematic diagram showing the "ocap. hashfile" file 434. 461 shows the details of the ocap. hashfile 434. ocap. hashfile in 461, which exists in the "/" directory 431, includes the hash values related to each of the "ocap. certificate. 1" file 436, the "ocap. signatrefile. 1" file 437, the "a" directory 432, the "ocap. crl. 2" file 438, and the "ocap. certificate. 2" file 439 that exist in the same directory 431.

Figure 44:
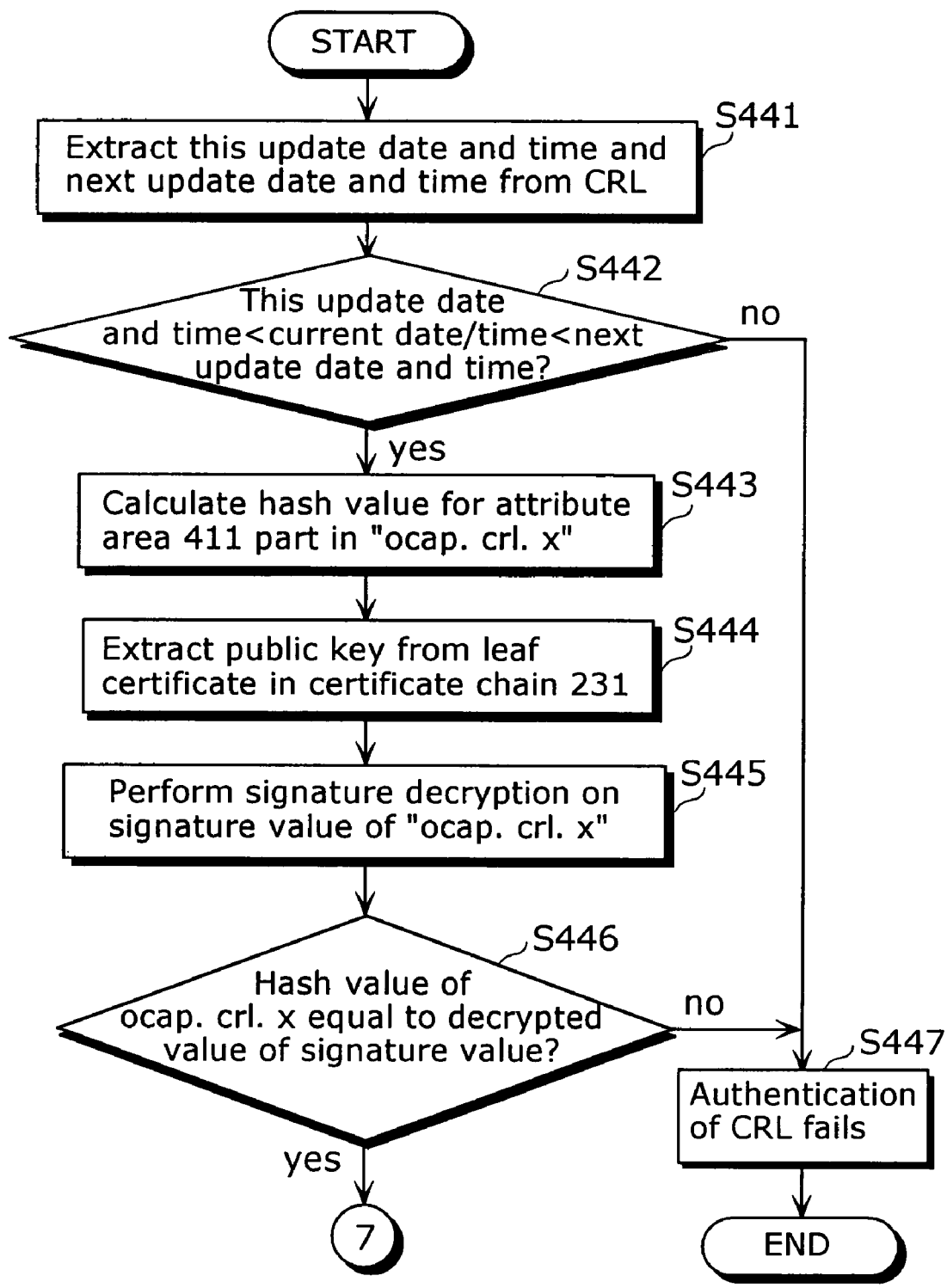
FIG. 44 is a flowchart showing an operation to be performed when the validity of the CRL is checked based on a hash value and a signature value according to the present invention.
Figure 45:
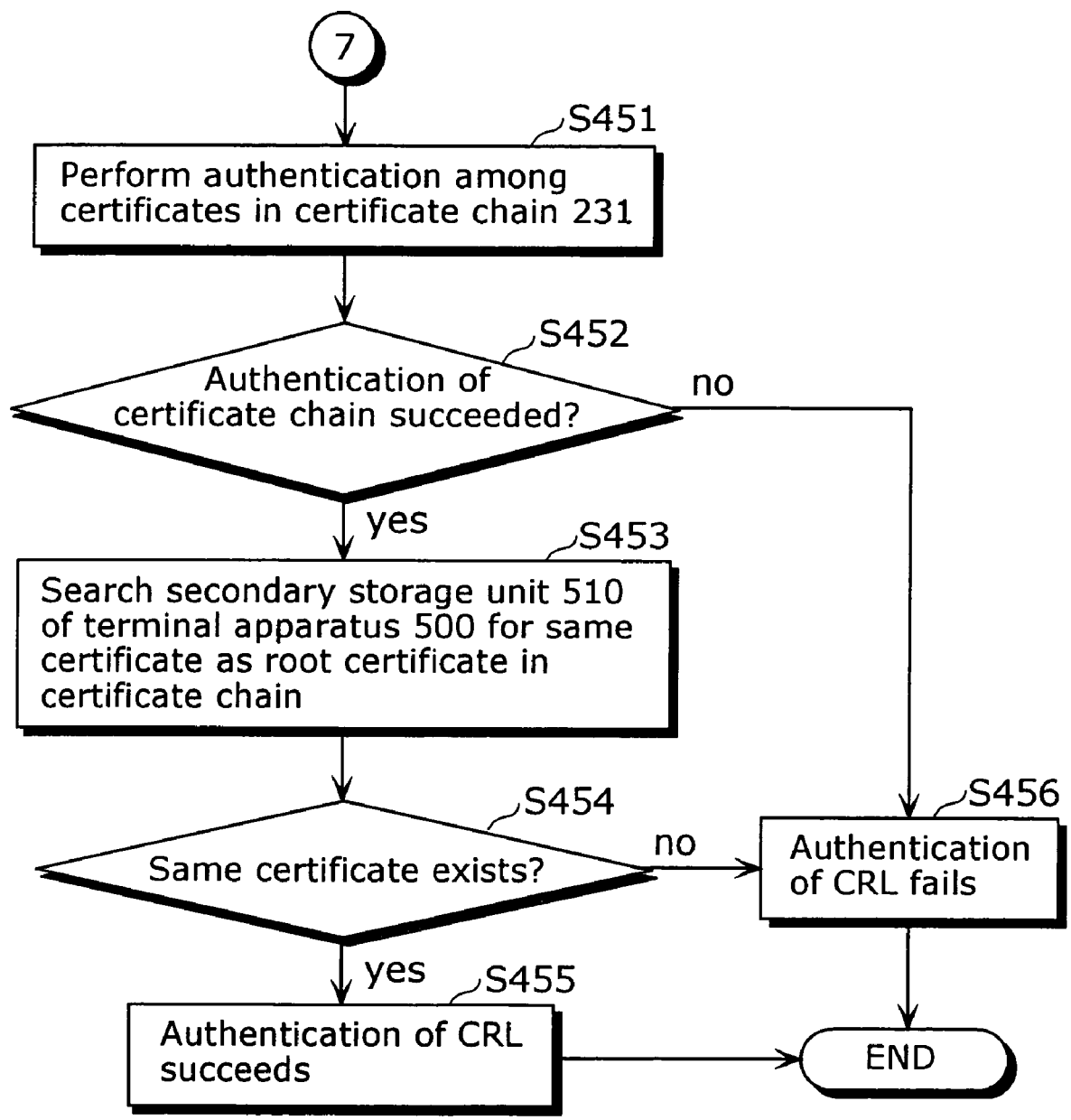
FIG. 45 is a flowchart showing an operation to be performed when the validity of the CRL is checked based on a chain relationship among certificates and a comparison between root certificates according to the present invention.

FIG. 44 is a flowchart for explaining authentication of a CRL. The following description is given for an example in which the file system has the configuration shown in FIG. 43. First, this update date and time 4112 and the next update date and time 4113 are extracted from the CRL (Step S441), and it is checked whether the current date and time is in between said this update date and time 4112 and next update date and time 4113 (Step S442). If not, this CRL is judged to be invalid (Step S447). If the current date and time is in between them, a hash value for the attribute area 411 is calculated in order to verify the signature value of the "ocap. crl. 2" file 438 (Step S443). At the same time, the public key 2417 of the leaf certificate 2313 is extracted from the "ocap. certificate. 2" file 439, which is a certificate chain (Step S444), and the signature value 413 of the "ocap. crl. 2" file 438 is decrypted with the extracted public key 2417 (Step S445). Then, it is checked whether the hash value obtained in Step S443 is equal to the decrypted value obtained in Step S445 (Step S446). If they are not equal, it is judged that the CRL is invalid (Step S447). If they are equal, referring to FIG. 45, authentication is performed for the "ocap. certificate. 2" file 439 that is a certificate chain (Step S451). A method for authenticating the certificate chain is the same as the one shown in FIG. 31 to FIG. 33, and therefore it is not described here. Subsequently, it is judged whether the authentication of the certificate chain is successful or not (Step S452), and if the authentication is a failure, this CRL is judged to be invalid (Step S456). Meanwhile, if the authentication is successful, the secondary storage unit 510 is searched for a certificate that is the same as the root certificate (Step S453). Here, if there is no matching root certificate, it is judged that the authentication is a failure and that this CRL is invalid (Step S456), whereas if a matching root certificate is included, it is judged that the authentication is successful and that the CRL is valid (Step S455).

The following describes a solution to the problem that a Java program is activated despite that a certificate is revoked according to the CRL. In order to support this, the present embodiment is added with the function of judging whether or not a certificate that was used to authenticate a Java program is a revoked one in the CRL, when an activation notification for such Java program is made.

FIG. 26 shows the constituent elements of the present embodiment. Except for 262 to which some addition is made and 269 which has not been described yet, no description is given for the constituent elements that have been described above.

The judgment unit 262; which is further capable of authenticating a CRL, requests the certificate revocation specification unit 269 to specify a certificate to be revoked by the CRL. Then, when the notification receiving unit 261 receives a pre-activation notification for a Java program that is related to a revoked certificate specified by the certificate revocation specification unit 269, the judgment unit 262 judges that the authentication is a failure. Meanwhile, when the notification receiving unit 261 receives a pre-activation notification for the Java program in the state in which the judgment unit 262 has failed to authenticate the CRL and therefore judged that such CRL is invalid, the judgment unit 262 judges that the authentication is successful.

When the judgment unit 262 recognizes that the authentication of the CRL was successful, the certificate revocation specification unit 269 specifies which one of the X. 509 certificates extracted by the certificate extraction unit 265 is a revoked certificate.

Figure 47:
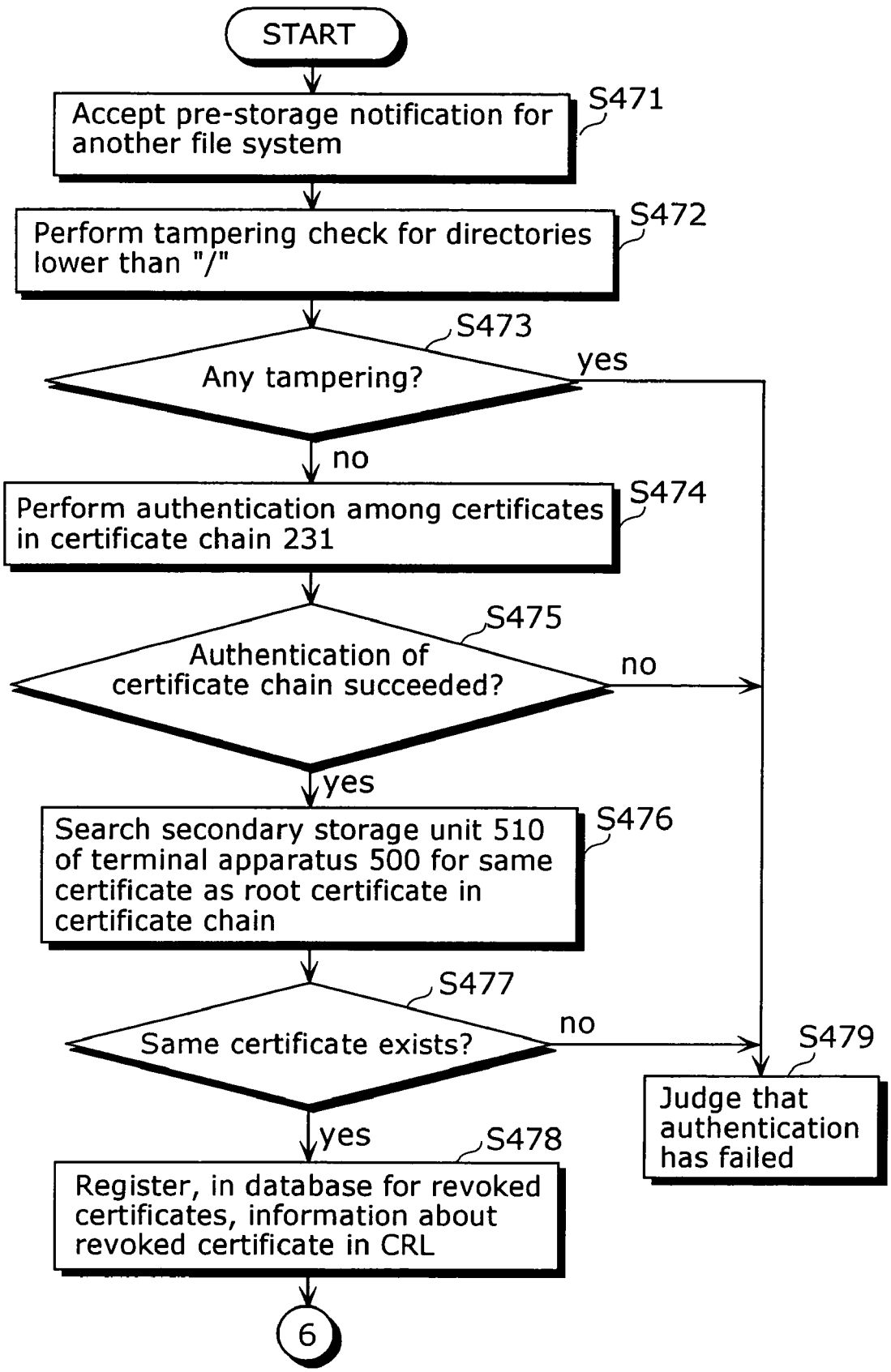
FIG. 47 is a flowchart showing an operation for performing authentication in the case where a CRL exists at program storage time according to the present invention.
Figure 48:
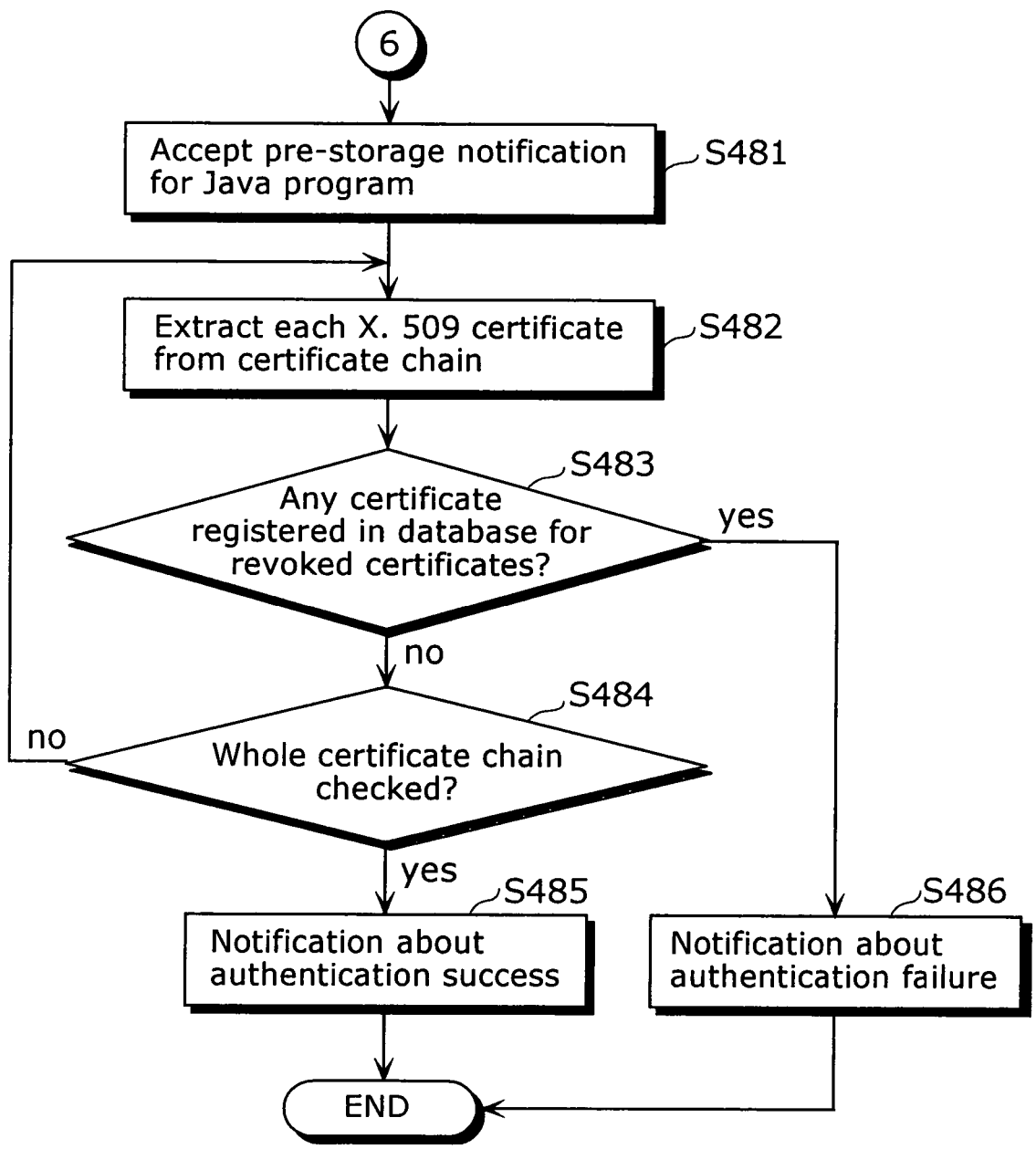
FIG. 48 is a flowchart showing an operation for performing authentication in the case where a CRL exists at program activation time.

As flowcharts, FIG. 47 and FIG. 48 are added. The following description is given according to these flowcharts. Assuming that a pre-storage notification for the file system shown in FIG. 21 is made now, the processes shown in the flowchart of FIG. 35 are started, and the process of Step S357 is completed in due time. Assuming that a pre-storage notification for another file system shown in FIG. 43 is then accepted, Step S471 to Step S477 are executed after the completion of the processes shown in the flowchart of FIG. 44. The processes of Step S471 to Step S477 are the same as those of Step S351 to Step S357. When Step S478 is reached and if the authentication of the "ocap. crl. 2" file 438 (the flowcharts of FIG. 44 and FIG. 45) is successful, information about revoked certificates contained in such file is written to the database of revoked certificates. FIG. 49 is a schematic diagram showing the database of revoked certificates. Issuer names are stored in a column 491, certificate serial numbers are stored in a column 492, and dates and times of revocation are stored in a column 493. Here, when a pre-activation notification for the "PPV1Xlet. class" 2114 is accepted (Step S481), it is checked whether any of the X. 509 certificates included in the certificate chain 231 of the "ocap. certificate. 1" file 2119 is included in the database of revoked certificates (Step S483). If there any of the certificates applies, it is judged that the authentication is a failure and a notification is made about this (Step S486). Meanwhile, when there is no applicable certificate, a check is performed for the whole certificate chain (Step S484), and a notification is made judging that the authentication is successful (Step 485). Through the above processes, it is possible to solve the problem that a Java program that should not be activated is activated, by judging that the authentication of the file is a failure for a file system whose certificate was valid at verification time but which turned revoked by the CRL by the time the Java program was activated.

Note that in the first to fourth embodiments, when a pre-activation notification for a Java program is received, it is also possible to further perform verification to see if the tree structure of a file system is correct or not by use of "ocap. hashfile" placed in each directory.

Furthermore, there is only one intermediate certificate in a certificate chain for simplification purposes, but there may be a plurality of intermediate certificates. However, all intermediate certificates need to be in a chain relationship when authentication of its certificate chain is performed.

Moreover, the following processes have been described in order of mention, but the present invention is not limited to such order: check of presence/absence of tampering; authentication of a certificate chain; and check to see if the secondary storage unit includes a root certificate that are the same as the root certificate in the certificate chain.

Furthermore, as for the storage of a file system, the security manager 1205f may store it using the library 1201b of the OS. Also, the first to fourth embodiments are also applicable to the case where "application description file" is provided in the top-level directory "/" of a file system, and as its contents, only a part of the file system is indicated as files to be stored. Thus, no problem occurs if only files to be stored are handled.

Moreover, programs have been described above as storage targets, but data other than programs may also be storage targets, meaning that the first to fourth embodiments are also applicable to data.

Furthermore, there is a possibility that more than one "ocap. certificate. x" corresponds to "ocap. signaturefile. x", in which case the authentication of at least one of the "ocap. certificate. x" files is required to be successful.

Also, "ocap. certificate. x" has been presented as an example certificate chain, "ocap. hashfile" has been presented as an example file having a hash value, and "ocap. signaturefile. x" has been presented as an example file for checking if "ocap. hashfile" in a "/" directory has been tampered with or not, but the present invention is not limited to these file names.

Moreover, in the case of authentication failure, authentication may be performed again after re-downloading.

Furthermore, in the case of authentication failure, a stored program as well as a certificate chain, a signature file, hash files that have been used for authentication may be deleted in order to reserve enough capacity for storage area.

Figure 50:
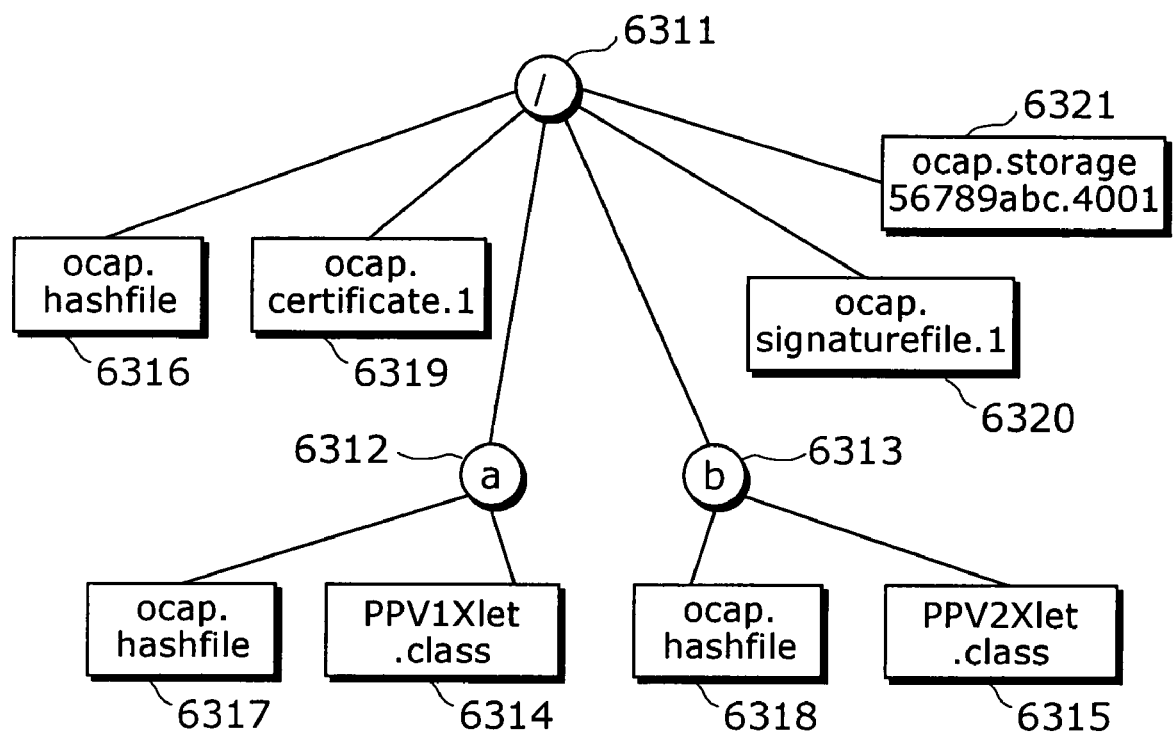
FIG. 50 is a diagram showing an example file system that includes files that are used to specify files to be stored according to the present invention.

Here, a description is given for the case where a file system that constitutes a program has a configuration shown in FIG. 50 and there is no description of files to be used for authentication as in the case of "application description file" shown in FIG. 51. 5011 to 5020 shown in FIG. 50 are equivalent to 2111 to 2120 shown in FIG. 21. 5021 denotes "application description file" that describes files to be stored. In "application description file" in FIG. 51, there is no description of "ocap. certificate. 1" 5019, "ocap. signaturefile. 1" 5020, and "ocap. hashfile" 5017 that are required for authentication. In this case, if files are stored just as shown in FIG. 51, files required to perform authentication will not be stored. Thus, authentication presented in the second, third, and fourth embodiments cannot be performed at the time of activation. When a stored program is to be activated, and files shown in FIG. 50, which shows files before such program gets stored, are ready for download, the stored files may be used as the files constituting the program and files used for authentication may be downloaded again for use of authentication.

However, there may be the case where files shown in FIG. 50, which shows files before the program is stored, cannot be downloaded. Therefore, files required for authentication may be stored for use of authentication to be performed at program activation time, even if they are not described in "application description file".

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

INDUSTRIAL APPLICABILITY

The authenticated program execution method according to the present invention, which is capable of guaranteeing the credibility of a program as well as improving responsiveness, is useful to temporarily improve the functionality of a digital television receiver as well as to add a function to it. Furthermore, the present invention is applicable not only to digital televisions but also to uses such as temporal improvement of the functionality of and temporal addition of a function to information devices controlled by software such as personal computers and mobile phones.

The invention claimed is:

1. An authenticated program execution method, comprising:

authenticating a program included in a transport stream and storing the authenticated program into a broadcast receiver according to information concerning storage of each data file of the program; and executing the authenticated stored program, wherein the authenticating and storing comprises executing authentication operations that include:

verifying whether two hash values are consistent, one hash value of the two hash values being calculated from each data file included in the program and an other hash value of the two hash values being stored in a hash file corresponding to said each data file;

verifying whether a certificate file included in the program is valid;

verifying whether a decrypted value and a hash value are consistent, the decrypted value being obtained by decrypting a signature value of a signature file included in the program using a public key of a leaf certificate included in the certificate file of the program, the hash value being calculated from a hash file located in a top directory of the program; and authenticating the program and storing each data file of the authenticated program according to the information concerning storage without executing the authenticated program, in the case where all of the following are satisfied: the two hash values are verified to be consistent; the certificate file is verified to be valid; and the decrypted value and the hash value are verified to be consistent, the executing the authenticated stored program comprises:

re-executing, when the stored program is executed, on the stored program, the verifying whether the certificate file included in the program is valid, among processes that include the verifying whether the two hash values are consistent, the verifying whether the certificate file included in the program is valid, and the verifying whether the decrypted value and the hash value are consistent, the processes having been performed on the stored program; and re-authenticating the stored program and executing the re-authenticated stored program only in the case where the certificate file included in the stored program is verified to be valid, and wherein the authenticating and storing the program includes executing all of the authentication operations without executing the program, and the executing the authenticated stored program includes executing at least one and less than all of the authentication operations.

2. The authenticated program execution method according to claim 1, wherein the executing the authenticated stored program includes executing only the one of the authentication operations of verifying whether the certificate file included in the program is valid.

3. An authenticated program execution apparatus, comprising:

an authenticator and storer that authenticates a program included in a transport stream and stores the authenticated program according to information concerning storage of each data file of the program; and an executor that executes the authenticated stored program, wherein the authenticator and storer comprises:

a first verifier that verifies whether two hash values are consistent, one hash value of the two hash values being calculated from each data file included in the program and an other hash value of the two hash values being stored in a hash file corresponding to said each data file;

a second verifier that verifies whether a certificate file included in the program is valid;

a third verifier that verifies whether a decrypted value and a hash value are consistent, the decrypted value being obtained by decrypting a signature value of a signature file included in the program using a public key of a leaf certificate included in the certificate file of the program, the hash value being calculated from a hash file located in a top directory of the program; and a second storer that authenticates the program and stores each data file of the authenticated program according to the information concerning storage without executing the authenticated program, in the case where all of the following are satisfied: the two hash values are verified to be consistent by the first verifier; the certificate file is verified to be valid by the second verifier; and the decrypted value and the hash value are verified to be consistent by the third verifier, the executor:

re-executes, when the stored program is executed, on the stored program, the verification of whether the certificate file included in the program is valid which is performed by the second verifier, among processes that include the verification of whether the two hash values are consistent which is performed by the first verifier, the verification of whether the certificate file including in the program is valid which is performed by the second verifier, and the verification of whether the decrypted value and the hash value are consistent which is performed by the third verifier, the processes having been performed on the stored program; and authenticates the stored program again and executes the authenticated stored program only in the case where the certificate file included in the stored program is verified to be valid, wherein the first verifier, the second verifier, the third verifier, and the second storer each perform their respective functions when the authenticator and storer authenticates and stores the program, and wherein at least one and less than all of the first verifier, the second verifier, the third verifier, and the second storer perform their respective functions when the executor executes the authenticated stored program.

4. The authenticated program execution apparatus according to claim 3, wherein only the second verifier performs its respective function when the executor executes the authenticated stored program.

5. A recording medium on which a program is recorded, the program causing a computer to execute:

authenticating a program included in a transport stream and storing the authenticated program into a broadcast receiver according to information concerning storage of each data file of the program; and executing the authenticated stored program, wherein the authenticating and storing comprises executing authentication operations that include:

verifying whether two hash values are consistent, one of the hash values being calculated from each data file included in the program and the other hash value being stored in a hash file corresponding to said each data file;

verifying whether a certificate file included in the program is valid;

verifying whether a decrypted value and a hash value are consistent, the decrypted value being obtained by decrypting a signature value of a signature file included in the program using a public key of a leaf certificate included in the certificate file of the program, and the hash value being calculated from a hash file located in a top directory of the program; and authenticating the program and storing each data file of the authenticated program according to the information concerning storage without executing the authenticated program, in the case where all of the following are satisfied: the two hash values are verified to be consistent; the certificate file is verified to be valid, and the decrypted value and the hash value are verified to be consistent, executing the authenticated stored program comprises:
re-executing, when the stored program is executed, on the stored program, the verifying whether the certificate file included in the program is valid, among processes that include the verifying whether the two hash values are consistent, the verifying whether the certificate file included in the program is valid, and the verifying whether the decrypted value and the hash value are consistent, the processes having been performed on the stored program; and re-authenticating the stored program and executing the re-authenticated stored program only in the case where the certificate file included in the stored program is verified to be valid, and wherein the authenticating and storing the program includes executing all of the authentication operations without executing the program and the executing the authenticated stored program includes executing at least one and less than all of the authentication operations.

6. The recording medium according to claim 5, wherein the executing the authenticated stored program includes executing only the one of the authentication operations of verifying whether the certificate file included in the program is valid.

* * * * *

UNITED STATES PATENT AND TRADEMARK OFFICE
CERTIFICATE OF CORRECTION

PATENT NO. : 7,698,562 B2 Page 1 of 1
APPLICATION NO. : 11/012335
DATED : April 13, 2010
INVENTOR(S) : Kusudo et al.

It is certified that error appears in the above-identified patent and that said Letters Patent is hereby corrected as shown below:

At Column 32, Line 31 (Claim 3, Line 42) of the printed patent, "including" should be -- included --.

Signed and Sealed this

Twelfth Day of October, 2010

David J. Kappos
*Director of the United States Patent and Trademark Office*